US006849717B1

(12) United States Patent
Sternberg et al.

(10) Patent No.: US 6,849,717 B1
(45) Date of Patent: Feb. 1, 2005

(54) POLYCYSTIC KIDNEY DISEASE GENE HOMOLOGS REQUIRED FOR MALE MATING BEHAVIOR IN NEMATODES AND ASSAYS BASED THEREON

(75) Inventors: Paul W. Sternberg, Pasadena, CA (US); Maureen M. Barr, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 712 days.

(21) Appl. No.: 09/655,160

(22) Filed: Sep. 5, 2000

Related U.S. Application Data

(62) Division of application No. 09/479,467, filed on Jan. 6, 2000, now abandoned.
(60) Provisional application No. 60/115,127, filed on Jan. 6, 1999.

(51) Int. Cl.$^7$ ............................................. C07K 14/435

(52) U.S. Cl. ..................................................... 530/350

(58) Field of Search ........................................ 530/350

(56) References Cited

U.S. PATENT DOCUMENTS

| | | |
|---|---|---|
| 4,568,639 A | 2/1986 | Lew ............................. 435/68 |
| 4,756,908 A | 7/1988 | Lew ............................. 424/88 |
| 5,196,333 A | 3/1993 | Chalfie et al. ............ 435/240.1 |
| 5,472,871 A | 12/1995 | Wood et al. .............. 435/252.3 |
| 5,559,026 A | 9/1996 | Price et al. ............... 435/254.2 |
| 5,741,668 A | 4/1998 | Ward et al. ................. 435/69.1 |
| 5,789,189 A | 8/1998 | Woo ............................. 435/30 |
| 5,840,540 A | 11/1998 | St. George-Hyslop et al. .......................... 435/69.1 |
| 5,891,628 A | 4/1999 | Reeders et al. ................. 435/6 |
| 5,929,207 A | 7/1999 | Horvitz et al. .............. 530/324 |
| 5,962,301 A | 10/1999 | Horvitz et al. .............. 435/226 |
| 5,972,882 A | 10/1999 | Gattone, II .................... 514/11 |
| 5,985,830 A | 11/1999 | Acott et al. .................... 514/12 |
| 5,986,054 A | 11/1999 | St. George-Hyslop et al. .. 530/350 |

FOREIGN PATENT DOCUMENTS

| | | |
|---|---|---|
| WO | 9534573 | 12/1995 |
| WO | 9638555 | 12/1996 |
| WO | 9937770 | 7/1999 |

OTHER PUBLICATIONS

Aroian et al., Mutations in the Caenorhabditis elegans let–23 EGFR–like gene define elements important for cell–type specificity and function, *The EMBO Journal* 13(2):360–366 (1994).

Aroian et al., The let–23 gene necessary for Caenorhabditis elegans vulval induction encodes a tyrosine kinase of the EGF receptor subfamily, *Nature* 348:393–699 (1990).

Aroian et al., Multiple Functions of let–23, a Caenorhabditis elegans Receptor Tyrosine Kinase Gene Required for Vulval Induction, *Genetics* 128:251–267 (1991).

Bargmann, Neurobiology of the Caenorhabditis elegans Genome, *Science* 282:2028–2033 (1998).

Barr et al., A polycystic kidney–disease gene homologue required for male mating behaviour in C. elegans, *Nature* 401:386–389 (1999).

Brenner, The Genetics of Caenorhabditis Elegans, *Genetics* 77:71–94 (1974).

Bronner–Fraser, M. and P.W. Sternberg, Pattern formation and development mechanisms: The cell biological basis of inductive signaling, *Curr. Opin. Genet. Dev.* 10:347–9 (2000).

Brundage et al., Mutations in a C. elegans $G_8\beta$ Gene Disrupt Movement, Egg Laying, and Viability, *Neuron* 16(5):999–1009 (1996).

Carraway et al., Mucin Structure and Function: Insights from Molecular Biology, *Trends in Glycoscience and Glycotechnology* 7(33):31–44 (1995).

Chalfie et al., Green Fluorescent Protein as a Marker for Gene Expression, *Science* 263:802–805 (1994).

Chamberlin et al., Characterization of Seven Genes Affecting Caenorhabditis elegans Hindgut Development, *Genetics* 153(2):731–742 (1999).

Chamberlin et al., The lin–3/let–23 pathway mediates inductive signalling during male spicule development in Caenorhabditis elegans, *Development* 120:2713–2721 (1994).

Chamberlin et al., The PAX gene egl–38 mediated developmental patterning in caenorhabditis elegans, *Developmetn* 124(20):3919–3928 (1997).

Chamberlin et al., Multiple cell interactions are required for fate specification during male spicule development in Caenorhabditis elegans, *Development* 118(2):297–324 (1993).

(List continued on next page.)

*Primary Examiner*—Robert A. Wax
(74) *Attorney, Agent, or Firm*—Gray Cary Ware & Freidenrich, LLP

(57) ABSTRACT

Nematodes, such as *Caenorhabditis elegans*, that express mutant and wild-type orthologs of human genes involved in polycystic kidney diseases (PKDs), are used to study the functions of the proteins encoded by the genes, to screen for other genes involved in the diseases, to identify mutations involved in the diseases, and to screen for drugs that affect PKD. Behaviors controlled by the action of the genes or gene products are identified and used in the assays. Hence an animal model is provided that permits study of the etiology of polycystic kidney disease and provides a tool to identify the genes involved in the disease pathway, and to identify compounds that may be used to treat or alter the disease progression, lessen its severity or ameliorate symptoms. The nematode genes that encode protein products, mutants of the genes, vectors that contain the genes and mutant genes and nematode strains that contain the vectors are also provided.

6 Claims, 7 Drawing Sheets

OTHER PUBLICATIONS

Chang et al., Reciprocal EGF signaling back to the uterus from the induced C. elegans vulva coordinates morphogenesis of epithelia, *Current Biology* 9(5):237–246 (1999).

Chang et al., C. elegans vulvua development as a model system to study the cancer biology of EGFR signaling, *Cancer and Metastatis Reviews* 18:203–13 (1999).

Chang et al., Caenorhabditis elegans SOS–1 is necessary for multiple RAS–mediated developmental signals, *The EMBO Journal* 19(13):3283–94 (2000).

Chen et al., Polycystin–L is a calcium–regulated cation channel permeable to calcium ions, *Nature* 401:383–386 (1999).

Clandinin et al., Inositol Trisphosphate Mediates a RAS–independent Response to LET–23 Receptor Tyrosine Kinase Activation in C. elegans, *Cell* 92(4):523–533 (1998).

Clandinin et al., Caenorhabditis elegans HOM–C Genes Regulate the Response of Vulval Precursor Cells to Inductive Signal, *Developmental Biology* 182(1):150–161 (1997).

Collet et al., Analysis of osm–6, a Gene That Affects Sensory Cilium Structure and Sensory Neuron Function in Caenorhabditis elegans, *Genetics* 148:187–200 (1998).

Daoust et al., Evidence for a Third Genetic Locus for Autosomal Dominant Polycystic Kidney Disease, *Genomics* 25:733–736 (1995).

Database Embl Nucleotide and Protein Sequences, Nov. 9, 1999, XP002140196 Hinxton, GB AC=AL132862. Caenorhabditis elegans cosmid Y73F8A. From nt 1605–9677.

Database Embl Nucleotide and Protein Sequences. Nov. 1, 1996, XP002140195 Hinxton, GB AC=Q21027. Similar to Glycoproteins. F59A6.3. Caenorhabditis elegans abstract.

Database Embl Nucleotide and Protein Sequences, Mar. 1, 1995, XP002140194 Hinxton, GB AC=Z48544, Caenorhabditis elegans cosmid ZK945. Polysystic kidney disease protein1. From nt 24444 to nt 25742.

Driscoll et al., Mechanotransduction, *C. elegans II*, pp. 645–677 (1997).

Ebert et al., A Moloney MLV–Rat Somatotropin Fusion Gene Produces Biologically Active Somatotroopin in a Transgenic Pig, *Molecular Endocrinology* 2:277–83 (1988).

Emmons et al., Mating, channels and kidney cysts, *Nature* 401:339–340 (1999).

Félix et al., Symmetry breakage in the development of one–armes gonads in nematodes, *Development* 122(7):2129–2142 (1996).

Félix et al., A gonad–dervied survival signal for vulval precursor cells in two nematode species, *Curr. Biol.* 8(5):287–290 (1998).

Félix et al., Evolution of Vulva Development in the Cephalobina (Nematoda)k, *Developmental Biology* 221:68–86 (2000).

Ferguson et al., A genetic pathway for the specification of the vulval cell lineages of Caenorhyabditis elegans, *Nature* 326:259–267 (1987).

Gabow et al. Polycyctic Kidney Disease, *Diseases of the Kidney* Schrier, R.W. and C.W. Gottschalk (eds.) 1993.

Gabow, Autosomal Dominant Polycystic Kidney Disease—More Than a Renal Disease, *American Journal of Kidney Diseases* 16(5):403–413 (1990).

Germino et al., The Gene for Autosomal Dominant Polycystic Kidney Disease Lies in a 750–kb CpG–Rich Region, *Genomics* 13:144–151 (1992).

Golden et al., The Roles of SH2/SH3 Domains in Nematode Development, *Bioessays* 14(7):481–484 (1992).

Hajdu–Cronin et al., Antagonism between $G_o$ α and $G_q$ α in Caenorhabditis elegans: the RGS protein EAT–16 is necessary for $G_o$ α signaling and regulates $G_q$ α activity, *Genes & Development* 13(14):1780–1793 (1999).

Hammer et al., Genetic Engineering of Mammalian Embryos, *J. Amin. Sci.* 63:269–78 (1986).

Han et al., C. elegans lin–45 raf gene participates in let–60 ras–stimulated vulval differentiation, *Nature* 363(6425):133–140 (1993).

Han et al., Analysis of dominant–negative mutations of the Caenorhabditis elegans let–60 ras gene, *Genes & Development* 5(12A):2188–2198 (1991).

Han et al., The let–60 Locus Controls the Swtich Between Vulval and Nonvulval Cell Fates in Caenorhabditis elegans, *Genetics* 126:899–913 (1990).

Herskowtiz, Functional inactivation of genes by dominant negative mutations, *Nature* 329:219–222 (1987).

Hill et al., The gene lin–3 encodes an inductive signal for vulval development in C. elegans, *Nature* 358(6386):470–476 (1992).

Hill et al., Cell fate patterning during C. elegans vulval development, *Development* pp. 9–18 (1993).

Himmelbauer et al., Human–Mouse Homologies in the Region of the Polycystic Kidney Disease Gene (PKD1), *Genomics* 13:35–38 (1992).

Hodgkin, Male Phenotypes and Mating Efficiency in Caenorhabditis elegans, *Genetics* 103:43–64 (1983).

Hodgkin, Sexual Dimorphism and Sex Determination,*The Nematode C. elegans*, pp. 243–279 (1988).

Hoffmann et al., Learning about cancer genes through invertebrate genetics, *Curr, Opin. Genet. Dev.* 2(1):45–52 (1992).

Hopper et al., ARK–1 inhibits EGFR Signaling in C. elegans, *Molecular Cell.* 6:66–75 (2000).

Horvitz et al., Multiple intercellular signalling systems control the development of the Caenorhabditis elegans vulva, *Nature* 351:535–541 (1991).

Houdebine et al., Production of pharmaceutical proteins from transgenic animals, *Journal of Biotechnology* 34:269–84 (1994).

Hsieh et al., The RING finger/B–box factor TAM–1 and a retinoblastoma–like protein LIN–35 modulate context–dependent gene silencing in Caenorhabditis elegans, *Genes & Development* 13(22):2958–70 (1999).

Huang et al., Genetic Dissection of Developmental Pathways, *Methods Cell Biol.* 48:97–122 (1995).

Huang et al., The lin–15 Locus Encodes Two Negative Regulators of Caenorhabditis elegans Vulval Development, *Molecular Biology of the Cell* 5:395–412 (1994).

Hudspeth, How the ear's works work, *Nature* 341:397–404 (1989).

Hughes et al., The polycyctic kidney disease 1 (PDK1) gene encodes a novel protein with multiple cell recognition domains, *Nature Genetics* 10:151–160 (1995).

Hughes et al., Identification of human homologue of the sea urchin receptor for egg jelly: a polycystic kidney disease–like protein, *Human Molecular Genetics* 8(3):543–549 (1999).

Jiang et al., An HMG1–like protein facilitates Wnt signaling in Caenorhabditis elegans, *Genes & Development* 13(7):877–889 (1999).

Jiang et al., Interactions of EGF, Wnt and HOM–C genes specify the P12 neuroectoblast fate in C. elegans, *Development* 125(12): 2337–2347 (1998).

Jiang et al., Socket Cells Mediate Spicule Morphogenesis in Caenorhabditis elegans Males, *Developmental Biology* 211(1):88–99 (1999).

Jongeward et al., sli–1, a Negative Regulator of let–23–Mediated Signaling in C. elegans, *Genetics* 139(4):1553–1566 (1995).

Kaplan et al., A dual mechanosensory and chemosensory neuron in Caenorhabditis elegans, *Proc. Natl. Acad. Sci. USA* 90:2227–2231 (1993).

Kappel et al., Regulating gene expression in transgenic animals, *Current Biology* 3:548–553 (1992).

Katz et al., Different Levels of the C. elegans Growth Factor LIN–3 Promote Distinct Vulval Precursor Fates, *Cell* 82(2):297–307 (1995).

Katz et al., A Point Mutation in the Extracellular Domain Activates LET–23, the Caenorhabditis elegans Epidermal Growth Factor Receptor HOmolong, *Mol. Cell. Biol.* 16(2):529–537 (1996).

Katz et al., A plethora of intercellular signals during Caenorhabditis elegans development, *Curr. Opin. Cell Biol.* 4(6):939–947 (1992).

Kayne et al., Ras pathways in Caenonrhabditis elegans, *Curr. Opin. Genet. Dev.* 5(1):38–43 (1995).

Kimberling et al., Autosomal Dominant Polycycstic Kidney Disease: Localization of the Second Gene to Chromosome 4q13–q23, *Genomics* 18:467–472 (1993).

Lee et al., unc–101, a gene required for many aspects of Caenorhabditis elegans development and behavior, encodes a clathrin–associated protein, *Genes & Development* 8:60–73 (1994).

Lesa et al, Positive and Negative Tissue–specific Signaling by a Nematode Epidermal Growth Factor Receptor, *Mol. Biol. Cell* 8(5):779–793 (1997).

Liu et al., Sensory Regulation of Male Mating Behavior in Caenorhabditis elegans, *Neuron* 14:79–89 (1995).

McDonald et al., Inherited Polycystic Kidney Disease in Children, *Seminars in Nephrology* 11(6):632–642 (1991).

Mendel et al., Participation of the Protein $G_o$ in Multiple Aspects of Behavior in C. elegans, *Science* 267(5204):1652–1655 (1995).

*Methods in Cell Biology* vol. 48: Caenorhabditis elegans: Modern Biological Analysis of an Organism, Epstein, H.F. and D.C. Skakes (eds.) Academic Press, Inc. 1995.

Mochizuki et al., PKD2, a Gene for Polycystic Kidney Disease That Encodes an Integral Membrane Protein, *Science* 272:1339–1342 (1996).

Montell et al., Molecular Characterization of the Drosophila trp Locus: A Putative Integral Membrane Protein Required for Phototransduction, *Neuron* 2:1313–1323 (1989).

Mori et al., The identification of a Caenorhabditis elegans homolog of $p34^{cdc2}$ kinase, *Mol. Gen. Genet.* 245:781–786 (1994).*

Mullins et al., Persepctices Series: Molecular Medicien in Genetically Engineered Animals, *J. Clin. Invest.*, 98(11):S37–S40 (1996).*

Newman et al., Coordinated morphogenesis of epithelia during development of the Caenorhabditis elegans uterine–vulval connection, *Proc. Natl. Acad. Sci. USA* 93(18):9329–9333 (1996).*

Newman et al., The Caenorhabditis elegans lin–12 gene mediates induction of ventral uterine specialziation by the anchor cell, *Development* 121(2):263–271 (1995).*

Newman et al., The lin–11 LIM domain transcription factor is necessary for morphogenesis of C. elegans uterine cells, *Development* 126(23):5319–26 (1999).*

Newman et al., Morphogenesis of the C. elegans hermaphordite uterus, *Development* , 122:3617–26 (1996).*

Newman et al., The Caenorhabditis elegans heterochronic gene lin–29 coordinates the vulval–uterine–epidermal connections, *Current Biol.* 10:1479–88 (2000).*

Normura et al., Identification of PKDL, a Novel Polycystic Kidney Disease 2–Like Gene Whose Murine Homologue Is Deleted in Mice with Kidney and Retinal Defects, *J . Biol. Chem.* 273(40):25967–25973 (1998).*

Perkins et al., Mutant Sensory Cilia in the Nematode Caenorhabditis elegans, *Developmental Biology* 117:456–487 (1986).*

Qian et al., PKD1 interacts with PKD2 through a probable coiled–coil domain, *Nature Genetics* 16:179–183 (1997).*

Reeders et al., A highly polymorphic DNA marker linked to adult polycystic kidney disease on chromosome 46, *Nature* 317:542–544 (1985).*

Sambrook et al. (1989) *Molecular Cloning: A Laboratory Manual*, 2nd ed. Cold Spring Harbor Laboratory Press, Cold Spring Harbor, NY.*

Schnabel et al., An Organ–Specific Differentiation Gene, pha–1, from Caenorhabditis elegans, *Science* 250:686–688 (1990).*

Scott et al., TRP, TRPL and trouble in photorecptor cells, *Current Opinion in Neurobiology* 8:383–388 (1998).*

Shim et al., Distinct and Redundant Functions of u1 Medium Chains of the AP–1 Clathrin–Associated Protein Complex in the Nematode Caenorhabditis elegans, *Molecular Biology* 11:2743–56 (2000).

Somlo et al., Fine Genetic Localization of the Gene for Autosomal Dominant Polycystic Kidney Disease (PKD1) with Respect to Physically Mapped Markers, *Genomics* 13:152–158 (1992).

Sommer et al., Apoptosis and change of competence limit the size of the vulva equivalnece group in pristtionchus pacificus: a genetic analysis, *Current Biology* 6(1):52–59 (1996).

Sommer et al., Evolution of Nematode Vulval Fate Patterning, *Developmental Biology* 173(2):396–407 (1996).

Sommer et al., Changes of Induction and Competence During the Evolution of Vulva Development in Nematodes, *Science* 265:114–118 (1994).

Sternberg et al., Molecular Genetics of Proto–oncogenes and Candidate Tumor Suppressors in Caenorhabditis elegans, *Cold Spring Harb. Symp. Quant. Biol.* 59:155–163 (1994).

Sternberg et al., Intercellular Signaling and Signal Transduction in C. elegans, *Annu. Rev. Genet.* 27:497–521 (1993).

Sternberg et al., LET–23–Mediated Signal Transduction During Caenorhabditis elegans Development, *Mol. Reprod. Dev.* 42(4):523–528 (1995).

Sternberg, Control of cell fates within equivalence groups in C. elegans, *TINS* 11(6):259–264 (1988).

Sternberg et al., Genetics of RAS signaling in C. elegans, *TIG* 14(11):466–472 (1998).

Sternberg et al., lin–17 Mutations of Caenorhabditis elegans Disrupt Certain Asymmetric Cell Divisions, *Developmental Biology* 130:67–73 (1988).

Sternberg et al., Role of a raf proto–oncogene during Caenorhabditis elegans vulval development, *Phil. Trans. R. Soc. Lond. B. Biol. Sci.* 340(1293):259–265 (1993).

Strojek et al., The Use of Transgenic Animal Techniques for Livestock Improvement, *Genetic Engineering: Principles and Methods*, 10:221–46 (1988).

Sulston et al., The Caenorhabditis elegans Male: Postembryonic Development of Nongonadal Structures, *Development Biology* 78:542–576 (1980).

The C. elegans Sequencing Consortium, Genome Sequence of the Nematode C. elegans: A Platform for Investigating Biology, *Science* 282:2012–2018 (1998).

Torres et al., New insights into polycystic kidney disease and its treatment, *Current Opinion in Nephorology and Hypertension* 7:159–169 (1998).

Tsiokaas et al., Homo– and heterodimeric interactions between the gene products of PKD1 and PKD2, *Proc. Natl. Acad. Sci. USA* 94:6965–6970 (1997).

Wall et al., Transgenic Livestock: Progress and Prospects for the Future, *Theriogenology*, 45:57–68 (1996).

Wang et al., Competence and Commitment of Caenorhabditis elegans Vulval Precursor Cells, *Developmental Biology* 212(1):12–24 (1999).

Wang et al., Patterning of the C. elegans 1 degree vulval lineage by RAS and Wnt pathways,*Development* 127:5047–58 (2000).

Ward et al., Electron Microscopial Reconstruction of the Anterior Sensory Anatomy of the Nematode Caenorhabditis elegans, *J. Comp. Neur.* 160:313–337 (1975).

Watson et al., The Fine Structure of Bacterial and Phage Genes, *Molecular Biology of the Gene, 4th Edition* p. 224 (1987).

White et al., The Structure of the Nervous System of the Nematode Caenorhabditis Elegans, *Phil. Trans. R. Soc. Lond. B* 314:1–67 (1986).

Wilson et al., 2.2 Mb of contiguous nucleotide sequence form chromosome III of C. elegans, *Nature* 368:32–8 (1994).

Yoon et al., Similarityu of sli–1, a Regulator of Vulval Development in C. elegans, to the Mammalian Proto–Oncogen c–cbl, *Science* 269(5227):102–1105 (1995).

Yoon et al., Requirements Multiple Domains of SLI–1, a Caenorhabditis elegans Homolgue of c–Cbl, and an Inhibitory Tyrosine in LET–23 in Regulating Vulvsl Differnetiation, *Molecular Biology of the Cell*, 11:4019–31 (2000).

Zerres et al., Mapping of the gene for autosomal recessive polycystic kidney disease (ARPKD) to chromosome 6p21–cen, *Nature Genetics* 7:429–432 (1994).

Zhen et al., The liprin protein SYD–2 regulates the differentiation of presynaptic termini in C. elegans, *Nature* 401:371–375 (1999).

Zwaal et al., Two Neuronal G Proteins are Involved in Chemosensation of the Caenorhabditis elegans Daure–Inducing Pheromone, *Genetics* 145(3):715–727 (1997).

\* cited by examiner

SEQUENCE LISTING

```
<160> NUMBER OF SEQ ID NOS: 16

<210> SEQ ID NO 1
<211> LENGTH: 12912
<212> TYPE: DNA
<213> ORGANISM: Homo sapiens PKD-1 gene
<220> FEATURE:
<221> NAME/KEY: CDS
<222> LOCATION: (1)..(12912)
<223> OTHER INFORMATION:

<400> SEQUENCE: 1 atg ccg ccc gcc gcg ccc gcc cgc ctg gcg ctg gcc ctg ggc ctg ggc         48
Met Pro Pro Ala Ala Pro Ala Arg Leu Ala Leu Ala Leu Gly Leu Gly
```

```
                                    -continued
1              5                  10                  15 ctg tgg ctc ggg gcg ctg gcg ggg ggg ccc ggg cgc ggc tgc ggg ccc     96
Leu Trp Leu Gly Ala Leu Ala Gly Gly Pro Gly Arg Gly Cys Gly Pro
             20                  25                  30 tgc gag ccc ccc tgc ctc tgc ggg cca gcg ccc ggc gcc gcc tgc cgc    144
Cys Glu Pro Pro Cys Leu Cys Gly Pro Ala Pro Gly Ala Ala Cys Arg
         35                  40                  45 gtc aac tgc tcg ggc cgc ggg ctg cgg acg ctc ggt ccc gcg ctg cgc    192
Val Asn Cys Ser Gly Arg Gly Leu Arg Thr Leu Gly Pro Ala Leu Arg
     50                  55                  60 atc ccc gcg gac gcc aca gag cta gac gtc tcc cac aac ctg ctc cgg    240
Ile Pro Ala Asp Ala Thr Glu Leu Asp Val Ser His Asn Leu Leu Arg
 65                  70                  75                  80 gcg ctg gac gtt ggg ctc ctg gcg aac ctc tcg gcg ctg gca gag ctg    288
Ala Leu Asp Val Gly Leu Leu Ala Asn Leu Ser Ala Leu Ala Glu Leu
                 85                  90                  95 gat ata agc aac aac aag att tct acg tta gaa gaa gga ata ttt gct    336
Asp Ile Ser Asn Asn Lys Ile Ser Thr Leu Glu Glu Gly Ile Phe Ala
                100                 105                 110 aat tta ttt aat tta agt gaa ata aac ctg agt ggg aac ccg ttt gag    384
Asn Leu Phe Asn Leu Ser Glu Ile Asn Leu Ser Gly Asn Pro Phe Glu
            115                 120                 125 tgt gac tgt ggc ctg gcg tgg ctg ccg caa tgg gcg gag gag cag cag    432
Cys Asp Cys Gly Leu Ala Trp Leu Pro Gln Trp Ala Glu Glu Gln Gln
        130                 135                 140 gtg cgg gtg gtg cag ccc gag gca gcc acg tgt gct ggg cct ggc tcc    480
Val Arg Val Val Gln Pro Glu Ala Ala Thr Cys Ala Gly Pro Gly Ser
145                 150                 155                 160 ctg gct ggc cag cct ctg ctt ggc atc ccc ttg ctg gac agt ggc tgt    528
Leu Ala Gly Gln Pro Leu Leu Gly Ile Pro Leu Leu Asp Ser Gly Cys
                165                 170                 175 ggt gag gag tat gtc gcc tgc ctc cct gac aac agc tca ggc acc gtg    576
Gly Glu Glu Tyr Val Ala Cys Leu Pro Asp Asn Ser Ser Gly Thr Val
            180                 185                 190 gca gca gtg tcc ttt tca gct gcc cac gaa ggc ctg ctt cag cca gag    624
Ala Ala Val Ser Phe Ser Ala Ala His Glu Gly Leu Leu Gln Pro Glu
        195                 200                 205 gcc tgc agc gcc ttc tgc ttc tcc acc ggc cag ggc ctc gca gcc ctc    672
Ala Cys Ser Ala Phe Cys Phe Ser Thr Gly Gln Gly Leu Ala Ala Leu
    210                 215                 220 tcg gag cag ggc tgg tgc ctg tgt ggg gcg gcc cag ccc tcc agt gcc    720
Ser Glu Gln Gly Trp Cys Leu Cys Gly Ala Ala Gln Pro Ser Ser Ala
225                 230                 235                 240 tcc ttt gcc tgc ctg tcc ctc tgc tcc ggg ccc ccg gca cct cct gcc    768
Ser Phe Ala Cys Leu Ser Leu Cys Ser Gly Pro Pro Ala Pro Pro Ala
                245                 250                 255 ccc acc tgt agg ggc ccc acc ctc ctc cag cac gtc ttc cct gcc tcc    816
Pro Thr Cys Arg Gly Pro Thr Leu Leu Gln His Val Phe Pro Ala Ser
            260                 265                 270 cca ggg gcc acc ctg gtg ggg ccc cac gga cct ctg gcc tct ggc cag    864
Pro Gly Ala Thr Leu Val Gly Pro His Gly Pro Leu Ala Ser Gly Gln
        275                 280                 285 cta gca gcc ttc cac atc gct gcc ccg ctc cct gtc act gac aca cgc    912
Leu Ala Ala Phe His Ile Ala Ala Pro Leu Pro Val Thr Asp Thr Arg
    290                 295                 300 tgg gac ttc gga gac ggc tcc gcc gag gtg gat gcc gct ggg ccg gct    960
Trp Asp Phe Gly Asp Gly Ser Ala Glu Val Asp Ala Ala Gly Pro Ala
305                 310                 315                 320 gcc tcg cat cgc tat gtg ctg cct ggg cgc tat cac gtg acg gcc gtg   1008
```

```
                                                      -continued

Ala Ser His Arg Tyr Val Leu Pro Gly Arg Tyr His Val Thr Ala Val
            325                 330                 335 ctg gcc ctg ggg gcc ggc tca gcc ctg ctg ggg aca gac gtg cag gtg     1056
Leu Ala Leu Gly Ala Gly Ser Ala Leu Leu Gly Thr Asp Val Gln Val
            340                 345                 350 gaa gcg gca cct gcc gcc ctg gag ctc gtg tgc ccg tcc tcg gtg cag     1104
Glu Ala Ala Pro Ala Ala Leu Glu Leu Val Cys Pro Ser Ser Val Gln
            355                 360                 365 agt gac gag agc ctc gac ctc agc atc cag aac cgc ggt ggt tca ggc     1152
Ser Asp Glu Ser Leu Asp Leu Ser Ile Gln Asn Arg Gly Gly Ser Gly
    370                 375                 380 ctg gag gcc gcc tac agc atc gtg gcc ctg ggc gag gag ccg gcc cga     1200
Leu Glu Ala Ala Tyr Ser Ile Val Ala Leu Gly Glu Glu Pro Ala Arg
385                 390                 395                 400 gcg gtg cac ccg ctc tgc ccc tcg gac acg gag atc ttc cct ggc aac     1248
Ala Val His Pro Leu Cys Pro Ser Asp Thr Glu Ile Phe Pro Gly Asn
                405                 410                 415 ggg cac tgc tac cgc ctg gtg gtg gag aag gcg gcc tgg ctg cag gcg     1296
Gly His Cys Tyr Arg Leu Val Val Glu Lys Ala Ala Trp Leu Gln Ala
                420                 425                 430 cag gag cag tgt cag gcc tgg gcc ggg gcc gcc ctg gca atg gtg gac     1344
Gln Glu Gln Cys Gln Ala Trp Ala Gly Ala Ala Leu Ala Met Val Asp
            435                 440                 445 agt ccc gcc gtg cag cgc ttc ctg gtc tcc cgg gtc acc agg agc cta     1392
Ser Pro Ala Val Gln Arg Phe Leu Val Ser Arg Val Thr Arg Ser Leu
    450                 455                 460 gac gtg tgg atc ggc ttc tcg act gtg cag ggg gtg gag gtg ggc cca     1440
Asp Val Trp Ile Gly Phe Ser Thr Val Gln Gly Val Glu Val Gly Pro
465                 470                 475                 480 gcg ccg cag ggc gag gcc ttc agc ctg gag agc tgc cag aac tgg ctg     1488
Ala Pro Gln Gly Glu Ala Phe Ser Leu Glu Ser Cys Gln Asn Trp Leu
                485                 490                 495 ccc ggg gag cca cac cca gcc aca gcc gag cac tgc gtc cgg ctc ggg     1536
Pro Gly Glu Pro His Pro Ala Thr Ala Glu His Cys Val Arg Leu Gly
                500                 505                 510 ccc acc ggg tgg tgt aac acc gac ctg tgc tca gcg ccg cac agc tac     1584
Pro Thr Gly Trp Cys Asn Thr Asp Leu Cys Ser Ala Pro His Ser Tyr
            515                 520                 525 gtc tgc gag ctg cag ccc gga ggc cca gtg cag gat gcc gag aac ctc     1632
Val Cys Glu Leu Gln Pro Gly Gly Pro Val Gln Asp Ala Glu Asn Leu
    530                 535                 540 ctc gtg gga gcg ccc agt ggg gac ctg cag gga ccc ctg acg cct ctg     1680
Leu Val Gly Ala Pro Ser Gly Asp Leu Gln Gly Pro Leu Thr Pro Leu
545                 550                 555                 560 gca cag cag gac ggc ctc tca gcc ccg cac gag ccc gtg gag gtc atg     1728
Ala Gln Gln Asp Gly Leu Ser Ala Pro His Glu Pro Val Glu Val Met
                565                 570                 575 gta ttc ccg ggc ctg cgt ctg agc cgt gaa gcc ttc ctc acc acg gcc     1776
Val Phe Pro Gly Leu Arg Leu Ser Arg Glu Ala Phe Leu Thr Thr Ala
                580                 585                 590 gaa ttt ggg acc cag gag ctc cgg cgg ccc gcc cag ctg cgg ctg cag     1824
Glu Phe Gly Thr Gln Glu Leu Arg Arg Pro Ala Gln Leu Arg Leu Gln
            595                 600                 605 gtg tac cgg ctc ctc agc aca gca ggg acc ccg gag aac ggc agc gag     1872
Val Tyr Arg Leu Leu Ser Thr Ala Gly Thr Pro Glu Asn Gly Ser Glu
    610                 615                 620 cct gag agc agg tcc ccg gac aac agg acc cag ctg gcc ccc gcg tgc     1920
Pro Glu Ser Arg Ser Pro Asp Asn Arg Thr Gln Leu Ala Pro Ala Cys
625                 630                 635                 640
```

-continued

| | | |
|---|---|---|
| atg cca ggg gga cgc tgg tgc cct gga gcc aac atc tgc ttg ccg ctg<br>Met Pro Gly Gly Arg Trp Cys Pro Gly Ala Asn Ile Cys Leu Pro Leu<br>645 650 655 | 1968 | |
| gac gcc tcc tgc cac ccc cag gcc tgc gcc aat ggc tgc acg tca ggg<br>Asp Ala Ser Cys His Pro Gln Ala Cys Ala Asn Gly Cys Thr Ser Gly<br>660 665 670 | 2016 | |
| cca ggc cta ccc ggg gcc ccc tat gcg cta tgg aga gag ttc ctc ttc<br>Pro Gly Leu Pro Gly Ala Pro Tyr Ala Leu Trp Arg Glu Phe Leu Phe<br>675 680 685 | 2064 | |
| tcc gtt ccc gcg ggg ccc ccc gcg cag tac tcg gtc acc ctc cac ggc<br>Ser Val Pro Ala Gly Pro Pro Ala Gln Tyr Ser Val Thr Leu His Gly<br>690 695 700 | 2112 | |
| cag gat gtc ctc atg ctc cct ggt gac ctc gtt ggc ttg cag cac gac<br>Gln Asp Val Leu Met Leu Pro Gly Asp Leu Val Gly Leu Gln His Asp<br>705 710 715 720 | 2160 | |
| gct ggc cct ggc gcc ctc ctg cac tgc tcg ccg gct ccc ggc cac cct<br>Ala Gly Pro Gly Ala Leu Leu His Cys Ser Pro Ala Pro Gly His Pro<br>725 730 735 | 2208 | |
| ggt ccc cgg gcc ccg tac ctc tcc gcc aac gcc tcg tca tgg ctg ccc<br>Gly Pro Arg Ala Pro Tyr Leu Ser Ala Asn Ala Ser Ser Trp Leu Pro<br>740 745 750 | 2256 | |
| cac ttg cca gcc cag ctg gag ggc act tgg ggc tgc cct gcc tgt gcc<br>His Leu Pro Ala Gln Leu Glu Gly Thr Trp Gly Cys Pro Ala Cys Ala<br>755 760 765 | 2304 | |
| ctg cgg ctg ctt gca caa cgg gaa cag ctc acc gtg ctg ctg ggc ttg<br>Leu Arg Leu Leu Ala Gln Arg Glu Gln Leu Thr Val Leu Leu Gly Leu<br>770 775 780 | 2352 | |
| agg ccc aac cct gga ctg cgg ctg cct ggg cgc tat gag gtc cgg gca<br>Arg Pro Asn Pro Gly Leu Arg Leu Pro Gly Arg Tyr Glu Val Arg Ala<br>785 790 795 800 | 2400 | |
| gag gtg ggc aat ggc gtg tcc agg cac aac ctc tcc tgc agc ttt gac<br>Glu Val Gly Asn Gly Val Ser Arg His Asn Leu Ser Cys Ser Phe Asp<br>805 810 815 | 2448 | |
| gtg gtc tcc cca gtg gct ggg ctg cgg gtc atc tac cct gcc ccc cgc<br>Val Val Ser Pro Val Ala Gly Leu Arg Val Ile Tyr Pro Ala Pro Arg<br>820 825 830 | 2496 | |
| gac ggc cgc ctc tac gtg ccc acc aac ggc tca gcc ttg gtg ctc cag<br>Asp Gly Arg Leu Tyr Val Pro Thr Asn Gly Ser Ala Leu Val Leu Gln<br>835 840 845 | 2544 | |
| gtg gac tct ggt gcc aac gcc acg gcc acg gct cgc tgg cct ggg ggc<br>Val Asp Ser Gly Ala Asn Ala Thr Ala Thr Ala Arg Trp Pro Gly Gly<br>850 855 860 | 2592 | |
| agt ctc agc gcc cgc ttt gag aat gtc tgc cct gcc ctg gtg gcc acc<br>Ser Leu Ser Ala Arg Phe Glu Asn Val Cys Pro Ala Leu Val Ala Thr<br>865 870 875 880 | 2640 | |
| ttc gtg ccc gcc tgc ccc tgg gag acc aac gat acc ctg ttc tca gtg<br>Phe Val Pro Ala Cys Pro Trp Glu Thr Asn Asp Thr Leu Phe Ser Val<br>885 890 895 | 2688 | |
| gta gca ctg ccg tgg ctc agt gag ggg gag cac gtg gtg gac gtg gtg<br>Val Ala Leu Pro Trp Leu Ser Glu Gly Glu His Val Val Asp Val Val<br>900 905 910 | 2736 | |
| gtg gaa aac agc gcc agc cgg gcc aac ctc agc ctg cgg gtg acg gcg<br>Val Glu Asn Ser Ala Ser Arg Ala Asn Leu Ser Leu Arg Val Thr Ala<br>915 920 925 | 2784 | |
| gag gag ccc atc tgt ggc ctc cgc gcc acg ccc agc ccc gag gcc cgt<br>Glu Glu Pro Ile Cys Gly Leu Arg Ala Thr Pro Ser Pro Glu Ala Arg<br>930 935 940 | 2832 | |
| gta ctg cag gga gtc cta gtg agg tac agc ccc gtg gtg gag gcc ggc<br>Val Leu Gln Gly Val Leu Val Arg Tyr Ser Pro Val Val Glu Ala Gly<br>945 950 955 960 | 2880 | |

-continued

| | |
|---|---|
| tcg gac atg gtc ttc cgg tgg acc atc aac gac aag cag tcc ctg acc<br>Ser Asp Met Val Phe Arg Trp Thr Ile Asn Asp Lys Gln Ser Leu Thr<br>                      965                     970                     975 | 2928 |
| ttc cag aac gtg gtc ttc aat gtc att tat cag agc gcg gcg gtc ttc<br>Phe Gln Asn Val Val Phe Asn Val Ile Tyr Gln Ser Ala Ala Val Phe<br>                      980                     985                     990 | 2976 |
| aag ctc tca ctg acg gcc tcc aac cac gtg agc aac gtc acc gtg aac<br>Lys Leu Ser Leu Thr Ala Ser Asn His Val Ser Asn Val Thr Val Asn<br>       995                    1000                  1005 | 3024 |
| tac aac gta acc gtg gag cgg atg aac agg atg cag ggt ctg cag<br>Tyr Asn Val Thr Val Glu Arg Met Asn Arg Met Gln Gly Leu Gln<br>  1010                   1015                  1020 | 3069 |
| gtc tcc aca gtg ccg gcc gtg ctg tcc ccc aat gcc acg cta gca<br>Val Ser Thr Val Pro Ala Val Leu Ser Pro Asn Ala Thr Leu Ala<br>  1025                   1030                  1035 | 3114 |
| ctg acg gcg ggc gtg ctg gtg gac tcg gcc gtg gag gtg gcc ttc<br>Leu Thr Ala Gly Val Leu Val Asp Ser Ala Val Glu Val Ala Phe<br>  1040                   1045                  1050 | 3159 |
| ctg tgg acc ttt ggg gat ggg gag cag gcc ctc cac cag ttc cag<br>Leu Trp Thr Phe Gly Asp Gly Glu Gln Ala Leu His Gln Phe Gln<br>  1055                   1060                  1065 | 3204 |
| cct ccg tac aac gag tcc ttc cca gtt cca gac ccc tcg gtg gcc<br>Pro Pro Tyr Asn Glu Ser Phe Pro Val Pro Asp Pro Ser Val Ala<br>  1070                   1075                  1080 | 3249 |
| cag gtg ctg gtg gag cac aat gtc acg cac acc tac gct gcc cca<br>Gln Val Leu Val Glu His Asn Val Thr His Thr Tyr Ala Ala Pro<br>  1085                   1090                  1095 | 3294 |
| ggt gag tac ctc ctg acc gtg ctg gca tct aat gcc ttc gag aac<br>Gly Glu Tyr Leu Leu Thr Val Leu Ala Ser Asn Ala Phe Glu Asn<br>  1100                   1105                  1110 | 3339 |
| ctg acg cag cag gtg cct gtg agc gtg cgc gcc tcc ctg ccc tcc<br>Leu Thr Gln Gln Val Pro Val Ser Val Arg Ala Ser Leu Pro Ser<br>  1115                   1120                  1125 | 3384 |
| gtg gct gtg ggt gtg agt gac ggc gtc ctg gtg gcc ggc cgg ccc<br>Val Ala Val Gly Val Ser Asp Gly Val Leu Val Ala Gly Arg Pro<br>  1130                   1135                  1140 | 3429 |
| gtc acc ttc tac ccg cac ccg ctg ccc tcg cct ggg ggt gtt ctt<br>Val Thr Phe Tyr Pro His Pro Leu Pro Ser Pro Gly Gly Val Leu<br>  1145                   1150                  1155 | 3474 |
| tac acg tgg gac ttc ggg gac ggc tcc cct gtc ctg acc cag agc<br>Tyr Thr Trp Asp Phe Gly Asp Gly Ser Pro Val Leu Thr Gln Ser<br>  1160                   1165                  1170 | 3519 |
| cag ccg gct gcc aac cac acc tat gcc tcg agg ggc acc tac cac<br>Gln Pro Ala Ala Asn His Thr Tyr Ala Ser Arg Gly Thr Tyr His<br>  1175                   1180                  1185 | 3564 |
| gtg cgc ctg gag gtc aac aac acg gtg agc ggt gcg gcg gcc cag<br>Val Arg Leu Glu Val Asn Asn Thr Val Ser Gly Ala Ala Ala Gln<br>  1190                   1195                  1200 | 3609 |
| gcg gat gtg cgc gtc ttt gag gag ctc cgc gga ctc agc gtg gac<br>Ala Asp Val Arg Val Phe Glu Glu Leu Arg Gly Leu Ser Val Asp<br>  1205                   1210                  1215 | 3654 |
| atg agc ctg gcc gtg gag cag ggc gcc ccc gtg gtg gtc agc gcc<br>Met Ser Leu Ala Val Glu Gln Gly Ala Pro Val Val Val Ser Ala<br>  1220                   1225                  1230 | 3699 |
| gcg gtg cag acg ggc gac aac atc acg tgg acc ttc gac atg ggg<br>Ala Val Gln Thr Gly Asp Asn Ile Thr Trp Thr Phe Asp Met Gly<br>  1235                   1240                  1245 | 3744 |
| gac ggc acc gtg ctg tcg ggc ccg gag gca aca gtg gag cat gtg<br>Asp Gly Thr Val Leu Ser Gly Pro Glu Ala Thr Val Glu His Val | 3789 |

-continued

|  | 1250 |  |  |  | 1255 |  |  |  | 1260 |  |  |  |  |  |
|---|---|---|---|---|---|---|---|---|---|---|---|---|---|---|
| tac | ctg | cgg | gca | cag | aac | tgc | aca | gtg | acc | gtg | ggt | gcg | ggc | agc | 3834 |
| Tyr | Leu | Arg | Ala | Gln | Asn | Cys | Thr | Val | Thr | Val | Gly | Ala | Gly | Ser | |
|  | 1265 |  |  |  | 1270 |  |  |  | 1275 |  |  |  |  |  |

| ccc | gcc | ggc | cac | ctg | gcc | cgg | agc | ctg | cac | gtg | ctg | gtc | ttc | gtg | 3879 |
| Pro | Ala | Gly | His | Leu | Ala | Arg | Ser | Leu | His | Val | Leu | Val | Phe | Val | |
|  | 1280 |  |  |  | 1285 |  |  |  | 1290 |  |  |  |  |  |

| ctg | gag | gtg | ctg | cgc | gtt | gaa | ccc | gcc | gcc | tgc | atc | ccc | acg | cag | 3924 |
| Leu | Glu | Val | Leu | Arg | Val | Glu | Pro | Ala | Ala | Cys | Ile | Pro | Thr | Gln | |
|  | 1295 |  |  |  | 1300 |  |  |  | 1305 |  |  |  |  |  |

| cct | gac | gcg | cgg | ctc | acg | gcc | tac | gtc | acc | ggg | aac | ccg | gcc | cac | 3969 |
| Pro | Asp | Ala | Arg | Leu | Thr | Ala | Tyr | Val | Thr | Gly | Asn | Pro | Ala | His | |
|  | 1310 |  |  |  | 1315 |  |  |  | 1320 |  |  |  |  |  |

| tac | ctc | ttc | gac | tgg | acc | ttc | ggg | gat | ggc | tcc | tcc | aac | acg | acc | 4014 |
| Tyr | Leu | Phe | Asp | Trp | Thr | Phe | Gly | Asp | Gly | Ser | Ser | Asn | Thr | Thr | |
|  | 1325 |  |  |  | 1330 |  |  |  | 1335 |  |  |  |  |  |

| gtg | cgg | ggg | tgc | ccg | acg | gtg | aca | cac | aac | ttc | acg | cgg | agc | ggc | 4059 |
| Val | Arg | Gly | Cys | Pro | Thr | Val | Thr | His | Asn | Phe | Thr | Arg | Ser | Gly | |
|  | 1340 |  |  |  | 1345 |  |  |  | 1350 |  |  |  |  |  |

| acg | ttc | ccc | ctg | gcg | ctg | gtg | ctg | tcc | agc | cgc | gtg | aac | agg | gcg | 4104 |
| Thr | Phe | Pro | Leu | Ala | Leu | Val | Leu | Ser | Ser | Arg | Val | Asn | Arg | Ala | |
|  | 1355 |  |  |  | 1360 |  |  |  | 1365 |  |  |  |  |  |

| cat | tac | ttc | acc | agc | atc | tgc | gtg | gag | cca | gag | gtg | ggc | aac | gtc | 4149 |
| His | Tyr | Phe | Thr | Ser | Ile | Cys | Val | Glu | Pro | Glu | Val | Gly | Asn | Val | |
|  | 1370 |  |  |  | 1375 |  |  |  | 1380 |  |  |  |  |  |

| acc | ctg | cag | cca | gag | agg | cag | ttt | gtg | cag | ctc | ggg | gac | gag | gcc | 4194 |
| Thr | Leu | Gln | Pro | Glu | Arg | Gln | Phe | Val | Gln | Leu | Gly | Asp | Glu | Ala | |
|  | 1385 |  |  |  | 1390 |  |  |  | 1395 |  |  |  |  |  |

| tgg | ctg | gtg | gca | tgt | gcc | tgg | ccc | ccg | ttc | ccc | tac | cgc | tac | acc | 4239 |
| Trp | Leu | Val | Ala | Cys | Ala | Trp | Pro | Pro | Phe | Pro | Tyr | Arg | Tyr | Thr | |
|  | 1400 |  |  |  | 1405 |  |  |  | 1410 |  |  |  |  |  |

| tgg | gac | ttt | ggc | acc | gag | gaa | gcc | gcc | ccc | acc | cgt | gcc | agg | ggc | 4284 |
| Trp | Asp | Phe | Gly | Thr | Glu | Glu | Ala | Ala | Pro | Thr | Arg | Ala | Arg | Gly | |
|  | 1415 |  |  |  | 1420 |  |  |  | 1425 |  |  |  |  |  |

| cct | gag | gtg | acg | ttc | atc | tac | cga | gac | cca | ggc | tcc | tat | ctt | gtg | 4329 |
| Pro | Glu | Val | Thr | Phe | Ile | Tyr | Arg | Asp | Pro | Gly | Ser | Tyr | Leu | Val | |
|  | 1430 |  |  |  | 1435 |  |  |  | 1440 |  |  |  |  |  |

| aca | gtc | acc | gcg | tcc | aac | aac | atc | tct | gct | gcc | aat | gac | tca | gcc | 4374 |
| Thr | Val | Thr | Ala | Ser | Asn | Asn | Ile | Ser | Ala | Ala | Asn | Asp | Ser | Ala | |
|  | 1445 |  |  |  | 1450 |  |  |  | 1455 |  |  |  |  |  |

| ctg | gtg | gag | gtg | cag | gag | ccc | gtg | ctg | gtc | acc | agc | atc | aag | gtc | 4419 |
| Leu | Val | Glu | Val | Gln | Glu | Pro | Val | Leu | Val | Thr | Ser | Ile | Lys | Val | |
|  | 1460 |  |  |  | 1465 |  |  |  | 1470 |  |  |  |  |  |

| aat | ggc | tcc | ctt | ggg | ctg | gag | ctg | cag | cag | ccg | tac | ctg | ttc | tct | 4464 |
| Asn | Gly | Ser | Leu | Gly | Leu | Glu | Leu | Gln | Gln | Pro | Tyr | Leu | Phe | Ser | |
|  | 1475 |  |  |  | 1480 |  |  |  | 1485 |  |  |  |  |  |

| gct | gtg | ggc | cgt | ggg | cgc | ccc | gcc | agc | tac | ctg | tgg | gat | ctg | ggg | 4509 |
| Ala | Val | Gly | Arg | Gly | Arg | Pro | Ala | Ser | Tyr | Leu | Trp | Asp | Leu | Gly | |
|  | 1490 |  |  |  | 1495 |  |  |  | 1500 |  |  |  |  |  |

| gac | ggt | ggg | tgg | ctc | gag | ggt | ccg | gag | gtc | acc | cac | gct | tac | aac | 4554 |
| Asp | Gly | Gly | Trp | Leu | Glu | Gly | Pro | Glu | Val | Thr | His | Ala | Tyr | Asn | |
|  | 1505 |  |  |  | 1510 |  |  |  | 1515 |  |  |  |  |  |

| agc | aca | ggt | gac | ttc | acc | gtt | agg | gtg | gcc | ggc | tgg | aat | gag | gtg | 4599 |
| Ser | Thr | Gly | Asp | Phe | Thr | Val | Arg | Val | Ala | Gly | Trp | Asn | Glu | Val | |
|  | 1520 |  |  |  | 1525 |  |  |  | 1530 |  |  |  |  |  |

| agc | cgc | agc | gag | gcc | tgg | ctc | aat | gtg | acg | gtg | aag | cgg | cgc | gtg | 4644 |
| Ser | Arg | Ser | Glu | Ala | Trp | Leu | Asn | Val | Thr | Val | Lys | Arg | Arg | Val | |
|  | 1535 |  |  |  | 1540 |  |  |  | 1545 |  |  |  |  |  |

| cgg | ggg | ctc | gtc | gtc | aat | gca | agc | cgc | acg | gtg | gtg | ccc | ctg | aat | 4689 |

```
                                                                    -continued Arg Gly Leu Val Val Asn Ala Ser Arg Thr Val Val Pro Leu Asn
    1550              1555              1560 ggg agc gtg agc ttc agc acg tcg ctg gag gcc ggc agt gat gtg    4734
Gly Ser Val Ser Phe Ser Thr Ser Leu Glu Ala Gly Ser Asp Val
    1565              1570              1575 cgc tat tcc tgg gtg ctc tgt gac cgc tgc acg ccc atc cct ggg    4779
Arg Tyr Ser Trp Val Leu Cys Asp Arg Cys Thr Pro Ile Pro Gly
    1580              1585              1590 ggt cct acc atc tct tac acc ttc cgc tcc gtg ggc acc ttc aat    4824
Gly Pro Thr Ile Ser Tyr Thr Phe Arg Ser Val Gly Thr Phe Asn
    1595              1600              1605 atc atc gtc acg gct gag aac gag gtg ggc tcc gcc cag gac agc    4869
Ile Ile Val Thr Ala Glu Asn Glu Val Gly Ser Ala Gln Asp Ser
    1610              1615              1620 atc ttc gtc tat gtc ctg cag ctc ata gag ggg ctg cag gtg gtg    4914
Ile Phe Val Tyr Val Leu Gln Leu Ile Glu Gly Leu Gln Val Val
    1625              1630              1635 ggc ggt ggc cgc tac ttc ccc acc aac cac acg gta cag ctg cag    4959
Gly Gly Gly Arg Tyr Phe Pro Thr Asn His Thr Val Gln Leu Gln
    1640              1645              1650 gcc gtg gtt agg gat ggc acc aac gtc tcc tac agc tgg act gcc    5004
Ala Val Val Arg Asp Gly Thr Asn Val Ser Tyr Ser Trp Thr Ala
    1655              1660              1665 tgg agg gac agg ggc ccg gcc ctg gcc ggc agc ggc aaa ggc ttc    5049
Trp Arg Asp Arg Gly Pro Ala Leu Ala Gly Ser Gly Lys Gly Phe
    1670              1675              1680 tcg ctc acc gtg ctc gag gcc ggc acc tac cat gtg cag ctg cgg    5094
Ser Leu Thr Val Leu Glu Ala Gly Thr Tyr His Val Gln Leu Arg
    1685              1690              1695 gcc acc aac atg ctg ggc agc gcc tgg gcc gac tgc acc atg gac    5139
Ala Thr Asn Met Leu Gly Ser Ala Trp Ala Asp Cys Thr Met Asp
    1700              1705              1710 ttc gtg gag cct gtg ggg tgg ctg atg gtg gcc gcc tcc ccg aac    5184
Phe Val Glu Pro Val Gly Trp Leu Met Val Ala Ala Ser Pro Asn
    1715              1720              1725 cca gct gcc gtc aac aca agc gtc acc ctc agt gcc gag ctg gct    5229
Pro Ala Ala Val Asn Thr Ser Val Thr Leu Ser Ala Glu Leu Ala
    1730              1735              1740 ggt ggc agt ggt gtc gta tac act tgg tcc ttg gag gag ggg ctg    5274
Gly Gly Ser Gly Val Val Tyr Thr Trp Ser Leu Glu Glu Gly Leu
    1745              1750              1755 agc tgg gag acc tcc gag cca ttt acc acc cat agc ttc ccc aca    5319
Ser Trp Glu Thr Ser Glu Pro Phe Thr Thr His Ser Phe Pro Thr
    1760              1765              1770 ccc ggc ctg cac ttg gtc acc atg acg gca ggg aac ccg ctg ggc    5364
Pro Gly Leu His Leu Val Thr Met Thr Ala Gly Asn Pro Leu Gly
    1775              1780              1785 tca gcc aac gcc acc gtg gaa gtg gat gtg cag gtg cct gtg agt    5409
Ser Ala Asn Ala Thr Val Glu Val Asp Val Gln Val Pro Val Ser
    1790              1795              1800 ggc ctc agc atc agg gcc agc gag ccc gga ggc agc ttc gtg gcg    5454
Gly Leu Ser Ile Arg Ala Ser Glu Pro Gly Gly Ser Phe Val Ala
    1805              1810              1815 gcc ggg tcc tct gtg ccc ttt tgg ggg cag ctg gcc acg ggc acc    5499
Ala Gly Ser Ser Val Pro Phe Trp Gly Gln Leu Ala Thr Gly Thr
    1820              1825              1830 aat gtg agc tgg tgc tgg gct gtg ccc ggc ggc agc agc aag cgt    5544
Asn Val Ser Trp Cys Trp Ala Val Pro Gly Gly Ser Ser Lys Arg
    1835              1840              1845
```

```
                                              -continued ggc cct cat gtc acc atg gtc ttc ccg gat gct ggc acc ttc tcc          5589
Gly Pro His Val Thr Met Val Phe Pro Asp Ala Gly Thr Phe Ser
    1850            1855                1860 atc cgg ctc aat gcc tcc aac gca gtc agc tgg gtc tca gcc acg          5634
Ile Arg Leu Asn Ala Ser Asn Ala Val Ser Trp Val Ser Ala Thr
1865                1870                1875 tac aac ctc acg gcg gag gag ccc atc gtg ggc ctg gtg ctg tgg          5679
Tyr Asn Leu Thr Ala Glu Glu Pro Ile Val Gly Leu Val Leu Trp
        1880                1885                1890 gcc agc agc aag gtg gtg gcg ccc ggg cag ctg gtc cat ttt cag          5724
Ala Ser Ser Lys Val Val Ala Pro Gly Gln Leu Val His Phe Gln
    1895                1900                1905 atc ctg ctg gct gcc ggc tca gct gtc acc ttc cgc cta cag gtc          5769
Ile Leu Leu Ala Ala Gly Ser Ala Val Thr Phe Arg Leu Gln Val
1910                1915                1920 ggc ggg gcc aac ccc gag gtg ctc ccc ggg ccc cgt ttc tcc cac          5814
Gly Gly Ala Asn Pro Glu Val Leu Pro Gly Pro Arg Phe Ser His
        1925                1930                1935 agc ttc ccc cgc gtc gga gac cac gtg gtg agc gtg cgg ggc aaa          5859
Ser Phe Pro Arg Val Gly Asp His Val Val Ser Val Arg Gly Lys
    1940                1945                1950 aac cac gtg agc tgg gcc cag gcg cag gtg cgc atc gtg gtg ctg          5904
Asn His Val Ser Trp Ala Gln Ala Gln Val Arg Ile Val Val Leu
1955                1960                1965 gag gcc gtg agt ggg ctg cag gtg ccc aac tgc tgc gag cct ggc          5949
Glu Ala Val Ser Gly Leu Gln Val Pro Asn Cys Cys Glu Pro Gly
        1970                1975                1980 atc gcc acg ggc act gag agg aac ttc aca gcc cgc gtg cag cgc          5994
Ile Ala Thr Gly Thr Glu Arg Asn Phe Thr Ala Arg Val Gln Arg
    1985                1990                1995 ggc tct cgg gtc gcc tac gcc tgg tac ttc tcg ctg cag aag gtc          6039
Gly Ser Arg Val Ala Tyr Ala Trp Tyr Phe Ser Leu Gln Lys Val
2000                2005                2010 cag ggc gac tcg ctg gtc atc ctg tcg ggc cgc gac gtc acc tac          6084
Gln Gly Asp Ser Leu Val Ile Leu Ser Gly Arg Asp Val Thr Tyr
        2015                2020                2025 acg ccc gtg gcc gcg ggg ctg ttg gag atc cag gtg cgc gcc ttc          6129
Thr Pro Val Ala Ala Gly Leu Leu Glu Ile Gln Val Arg Ala Phe
    2030                2035                2040 aac gcc ctg ggc agt gag aac cgc acg ctg gtg ctg gag gtt cag          6174
Asn Ala Leu Gly Ser Glu Asn Arg Thr Leu Val Leu Glu Val Gln
2045                2050                2055 gac gcc gtc cag tat gtg gcc ctg cag agc ggc ccc tgc ttc acc          6219
Asp Ala Val Gln Tyr Val Ala Leu Gln Ser Gly Pro Cys Phe Thr
        2060                2065                2070 aac cgc tcg gcg cag ttt gag gcc gcc acc agc ccc agc ccc cgg          6264
Asn Arg Ser Ala Gln Phe Glu Ala Ala Thr Ser Pro Ser Pro Arg
    2075                2080                2085 cgt gtg gcc tac cac tgg gac ttt ggg gat ggg tcg cca ggg cag          6309
Arg Val Ala Tyr His Trp Asp Phe Gly Asp Gly Ser Pro Gly Gln
2090                2095                2100 gac aca gat gag ccc agg gcc gag cac tcc tac ctg agg cct ggg          6354
Asp Thr Asp Glu Pro Arg Ala Glu His Ser Tyr Leu Arg Pro Gly
        2105                2110                2115 gac tac cgc gtg cag gtg aac gcc tcc aac ctg gtg agc ttc ttc          6399
Asp Tyr Arg Val Gln Val Asn Ala Ser Asn Leu Val Ser Phe Phe
    2120                2125                2130 gtg gcg cag gcc acg gtg acc gtc cag gtg ctg gcc tgc cgg gag          6444
Val Ala Gln Ala Thr Val Thr Val Gln Val Leu Ala Cys Arg Glu
2135                2140                2145
```

-continued

| | | |
|---|---|---|
| ccg gag gtg gac gtg gtc ctg ccc ctg cag gtg ctg atg cgg cga<br>Pro Glu Val Asp Val Val Leu Pro Leu Gln Val Leu Met Arg Arg<br>2150                           2155                         2160 | | 6489 |
| tca cag cgc aac tac ttg gag gcc cac gtt gac ctg cgc gac tgc<br>Ser Gln Arg Asn Tyr Leu Glu Ala His Val Asp Leu Arg Asp Cys<br>2165                           2170                         2175 | | 6534 |
| gtc acc tac cag act gag tac cgc tgg gag gtg tat cgc acc gcc<br>Val Thr Tyr Gln Thr Glu Tyr Arg Trp Glu Val Tyr Arg Thr Ala<br>2180                           2185                         2190 | | 6579 |
| agc tgc cag cgg ccg ggg cgc cca gcg cgt gtg gcc ctg ccc ggc<br>Ser Cys Gln Arg Pro Gly Arg Pro Ala Arg Val Ala Leu Pro Gly<br>2195                           2200                         2205 | | 6624 |
| gtg gac gtg agc cgg cct cgg ctg gtg ctg ccg cgg ctg gcg ctg<br>Val Asp Val Ser Arg Pro Arg Leu Val Leu Pro Arg Leu Ala Leu<br>2210                           2215                         2220 | | 6669 |
| cct gtg ggg cac tac tgc ttt gtg ttt gtc gtg tca ttt ggg gac<br>Pro Val Gly His Tyr Cys Phe Val Phe Val Val Ser Phe Gly Asp<br>2225                           2230                         2235 | | 6714 |
| acg cca ctg aca cag agc atc cag gcc aat gtg acg gtg gcc ccc<br>Thr Pro Leu Thr Gln Ser Ile Gln Ala Asn Val Thr Val Ala Pro<br>2240                           2245                         2250 | | 6759 |
| gag cgc ctg gtg ccc atc att gag ggt ggc tca tac cgc gtg tgg<br>Glu Arg Leu Val Pro Ile Ile Glu Gly Gly Ser Tyr Arg Val Trp<br>2255                           2260                         2265 | | 6804 |
| tca gac aca cgg gac ctg gtg ctg gat ggg agc gag tcc tac gac<br>Ser Asp Thr Arg Asp Leu Val Leu Asp Gly Ser Glu Ser Tyr Asp<br>2270                           2275                         2280 | | 6849 |
| ccc aac ctg gag gac ggc gac cag acg ccg ctc agt ttc cac tgg<br>Pro Asn Leu Glu Asp Gly Asp Gln Thr Pro Leu Ser Phe His Trp<br>2285                           2290                         2295 | | 6894 |
| gcc tgt gtg gct tcg aca cag agg gag gct ggc ggg tgt gcg ctg<br>Ala Cys Val Ala Ser Thr Gln Arg Glu Ala Gly Gly Cys Ala Leu<br>2300                           2305                         2310 | | 6939 |
| aac ttt ggg ccc cgc ggg agc agc acg gtc acc att cca cgg gag<br>Asn Phe Gly Pro Arg Gly Ser Ser Thr Val Thr Ile Pro Arg Glu<br>2315                           2320                         2325 | | 6984 |
| cgg ctg gcg gct ggc gtg gag tac acc ttc agc ctg acc gtg tgg<br>Arg Leu Ala Ala Gly Val Glu Tyr Thr Phe Ser Leu Thr Val Trp<br>2330                           2335                         2340 | | 7029 |
| aag gcc ggc cgc aag gag gag gcc acc aac cag acg gtg ctg atc<br>Lys Ala Gly Arg Lys Glu Glu Ala Thr Asn Gln Thr Val Leu Ile<br>2345                           2350                         2355 | | 7074 |
| cgg agt ggc cgg gtg ccc att gtg tcc ttg gag tgt gtg tcc tgc<br>Arg Ser Gly Arg Val Pro Ile Val Ser Leu Glu Cys Val Ser Cys<br>2360                           2365                         2370 | | 7119 |
| aag gca cag gcc gtg tac gaa gtg agc cgc agc tcc tac gtg tac<br>Lys Ala Gln Ala Val Tyr Glu Val Ser Arg Ser Ser Tyr Val Tyr<br>2375                           2380                         2385 | | 7164 |
| ttg gag ggc cgc tgc ctc aat tgc agc agc ggc tcc aag cga ggg<br>Leu Glu Gly Arg Cys Leu Asn Cys Ser Ser Gly Ser Lys Arg Gly<br>2390                           2395                         2400 | | 7209 |
| cgg tgg gct gca cgt acg ttc agc aac aag acg ctg gtg ctg gat<br>Arg Trp Ala Ala Arg Thr Phe Ser Asn Lys Thr Leu Val Leu Asp<br>2405                           2410                         2415 | | 7254 |
| gag acc acc aca tcc acg ggc agt gca ggc atg cga ctg gtg ctg<br>Glu Thr Thr Thr Ser Thr Gly Ser Ala Gly Met Arg Leu Val Leu<br>2420                           2425                         2430 | | 7299 |
| cgg cgg ggc gtg ctg cgg gac ggc gag gga tac acc ttc acg ctc<br>Arg Arg Gly Val Leu Arg Asp Gly Glu Gly Tyr Thr Phe Thr Leu | | 7344 |

|   |   |   |   |   |   |   |   |   |   |   |   |   |   |   |   |
|---|---|---|---|---|---|---|---|---|---|---|---|---|---|---|---|
| | 2435 | | | | | 2440 | | | | | 2445 | | | | |
| acg | gtg | ctg | ggc | cgc | tct | ggc | gag | gag | gag | ggc | tgc | gcc | tcc | atc | 7389 |
| Thr | Val | Leu | Gly | Arg | Ser | Gly | Glu | Glu | Glu | Gly | Cys | Ala | Ser | Ile | |
| | 2450 | | | | | 2455 | | | | | 2460 | | | | |
| cgc | ctg | tcc | ccc | aac | cgc | ccg | ccg | ctg | ggg | ggc | tct | tgc | cgc | ctc | 7434 |
| Arg | Leu | Ser | Pro | Asn | Arg | Pro | Pro | Leu | Gly | Gly | Ser | Cys | Arg | Leu | |
| | 2465 | | | | | 2470 | | | | | 2475 | | | | |
| ttc | cca | ctg | ggc | gct | gtg | cac | gcc | ctc | acc | acc | aag | gtg | cac | ttc | 7479 |
| Phe | Pro | Leu | Gly | Ala | Val | His | Ala | Leu | Thr | Thr | Lys | Val | His | Phe | |
| | 2480 | | | | | 2485 | | | | | 2490 | | | | |
| gaa | tgc | acg | ggc | tgg | cat | gac | gcg | gag | gat | gct | ggc | gcc | ccg | ctg | 7524 |
| Glu | Cys | Thr | Gly | Trp | His | Asp | Ala | Glu | Asp | Ala | Gly | Ala | Pro | Leu | |
| | 2495 | | | | | 2500 | | | | | 2505 | | | | |
| gtg | tac | gcc | ctg | ctg | ctg | cgg | cgc | tgt | cgc | cag | ggc | cac | tgc | gag | 7569 |
| Val | Tyr | Ala | Leu | Leu | Leu | Arg | Arg | Cys | Arg | Gln | Gly | His | Cys | Glu | |
| | 2510 | | | | | 2515 | | | | | 2520 | | | | |
| gag | ttc | tgt | gtc | tac | aag | ggc | agc | ctc | tcc | agc | tac | gga | gcc | gtg | 7614 |
| Glu | Phe | Cys | Val | Tyr | Lys | Gly | Ser | Leu | Ser | Ser | Tyr | Gly | Ala | Val | |
| | 2525 | | | | | 2530 | | | | | 2535 | | | | |
| ctg | ccc | ccg | ggt | ttc | agg | cca | cac | ttc | gag | gtg | ggc | ctg | gcc | gtg | 7659 |
| Leu | Pro | Pro | Gly | Phe | Arg | Pro | His | Phe | Glu | Val | Gly | Leu | Ala | Val | |
| | 2540 | | | | | 2545 | | | | | 2550 | | | | |
| gtg | gtg | cag | gac | cag | ctg | gga | gcc | gct | gtg | gtc | gcc | ctc | aac | agg | 7704 |
| Val | Val | Gln | Asp | Gln | Leu | Gly | Ala | Ala | Val | Val | Ala | Leu | Asn | Arg | |
| | 2555 | | | | | 2560 | | | | | 2565 | | | | |
| tct | ttg | gcc | atc | acc | ctc | cca | gag | ccc | aac | ggc | agc | gca | acg | ggg | 7749 |
| Ser | Leu | Ala | Ile | Thr | Leu | Pro | Glu | Pro | Asn | Gly | Ser | Ala | Thr | Gly | |
| | 2570 | | | | | 2575 | | | | | 2580 | | | | |
| ctc | aca | gtc | tgg | ctg | cac | ggg | ctc | acc | gct | agt | gtg | ctc | cca | ggg | 7794 |
| Leu | Thr | Val | Trp | Leu | His | Gly | Leu | Thr | Ala | Ser | Val | Leu | Pro | Gly | |
| | 2585 | | | | | 2590 | | | | | 2595 | | | | |
| ctg | ctg | cgg | cag | gcc | gat | ccc | cag | cac | gtc | atc | gag | tac | tcg | ttg | 7839 |
| Leu | Leu | Arg | Gln | Ala | Asp | Pro | Gln | His | Val | Ile | Glu | Tyr | Ser | Leu | |
| | 2600 | | | | | 2605 | | | | | 2610 | | | | |
| gcc | ctg | gtc | acc | gtg | ctg | aac | gag | tac | gag | cgg | gcc | ctg | gac | gtg | 7884 |
| Ala | Leu | Val | Thr | Val | Leu | Asn | Glu | Tyr | Glu | Arg | Ala | Leu | Asp | Val | |
| | 2615 | | | | | 2620 | | | | | 2625 | | | | |
| gcg | gca | gag | ccc | aag | cac | gag | cgg | cag | cac | cga | gcc | cag | ata | cgc | 7929 |
| Ala | Ala | Glu | Pro | Lys | His | Glu | Arg | Gln | His | Arg | Ala | Gln | Ile | Arg | |
| | 2630 | | | | | 2635 | | | | | 2640 | | | | |
| aag | aac | atc | acg | gag | act | ctg | gtg | tcc | ctg | agg | gtc | cac | act | gtg | 7974 |
| Lys | Asn | Ile | Thr | Glu | Thr | Leu | Val | Ser | Leu | Arg | Val | His | Thr | Val | |
| | 2645 | | | | | 2650 | | | | | 2655 | | | | |
| gat | gac | atc | cag | cag | atc | gct | gct | gcg | ctg | gcc | cag | tgc | atg | ggg | 8019 |
| Asp | Asp | Ile | Gln | Gln | Ile | Ala | Ala | Ala | Leu | Ala | Gln | Cys | Met | Gly | |
| | 2660 | | | | | 2665 | | | | | 2670 | | | | |
| ccc | agc | agg | gag | ctc | gta | tgc | cgc | tcg | tgc | ctg | aag | cag | acg | ctg | 8064 |
| Pro | Ser | Arg | Glu | Leu | Val | Cys | Arg | Ser | Cys | Leu | Lys | Gln | Thr | Leu | |
| | 2675 | | | | | 2680 | | | | | 2685 | | | | |
| cac | aag | ctg | gag | gcc | atg | atg | ctc | atc | ctg | cag | gca | gag | acc | acc | 8109 |
| His | Lys | Leu | Glu | Ala | Met | Met | Leu | Ile | Leu | Gln | Ala | Glu | Thr | Thr | |
| | 2690 | | | | | 2695 | | | | | 2700 | | | | |
| gcg | ggc | acc | gtg | acg | ccc | acc | gcc | atc | gga | gac | agc | atc | ctc | aac | 8154 |
| Ala | Gly | Thr | Val | Thr | Pro | Thr | Ala | Ile | Gly | Asp | Ser | Ile | Leu | Asn | |
| | 2705 | | | | | 2710 | | | | | 2715 | | | | |
| atc | aca | gga | gac | ctc | atc | cac | ctg | gcc | agc | tcg | gac | gtg | cgg | gca | 8199 |
| Ile | Thr | Gly | Asp | Leu | Ile | His | Leu | Ala | Ser | Ser | Asp | Val | Arg | Ala | |
| | 2720 | | | | | 2725 | | | | | 2730 | | | | |
| cca | cag | ccc | tca | gag | ctg | gga | gcc | gag | tca | cca | tct | cgg | atg | gtg | 8244 |

```
                                                                -continued

Pro Gln Pro Ser Glu Leu Gly Ala Glu Ser Pro Ser Arg Met Val
    2735            2740                2745 gcg tcc cag gcc tac aac ctg acc tct gcc ctc atg cgc atc ctc      8289
Ala Ser Gln Ala Tyr Asn Leu Thr Ser Ala Leu Met Arg Ile Leu
2750            2755                2760 atg cgc tcc cgc gtg ctc aac gag gag ccc ctg acg ctg gcg ggc      8334
Met Arg Ser Arg Val Leu Asn Glu Glu Pro Leu Thr Leu Ala Gly
        2765            2770                2775 gag gag atc gtg gcc cag ggc aag cgc tcg gac ccg cgg agc ctg      8379
Glu Glu Ile Val Ala Gln Gly Lys Arg Ser Asp Pro Arg Ser Leu
2780            2785                2790 ctg tgc tat ggc ggc gcc cca ggg cct ggc tgc cac ttc tcc atc      8424
Leu Cys Tyr Gly Gly Ala Pro Gly Pro Gly Cys His Phe Ser Ile
        2795            2800                2805 ccc gag gct ttc agc ggg gcc ctg gcc aac ctc agt gac gtg gtg      8469
Pro Glu Ala Phe Ser Gly Ala Leu Ala Asn Leu Ser Asp Val Val
2810            2815                2820 cag ctc atc ttt ctg gtg gac tcc aat ccc ttt ccc ttt ggc tat      8514
Gln Leu Ile Phe Leu Val Asp Ser Asn Pro Phe Pro Phe Gly Tyr
        2825            2830                2835 atc agc aac tac acc gtc tcc acc aag gtg gcc tcg atg gca ttc      8559
Ile Ser Asn Tyr Thr Val Ser Thr Lys Val Ala Ser Met Ala Phe
2840            2845                2850 cag aca cag gcc ggc gcc cag atc ccc atc gag cgg ctg gcc tca      8604
Gln Thr Gln Ala Gly Ala Gln Ile Pro Ile Glu Arg Leu Ala Ser
        2855            2860                2865 gag cgc gcc atc acc gtg aag gtg ccc aac aac tcg gac tgg gct      8649
Glu Arg Ala Ile Thr Val Lys Val Pro Asn Asn Ser Asp Trp Ala
2870            2875                2880 gcc cgg ggc cac cgc agc tcc gcc aac tcc gcc aac tcc gtt gtg      8694
Ala Arg Gly His Arg Ser Ser Ala Asn Ser Ala Asn Ser Val Val
        2885            2890                2895 gtc cag ccc cag gcc tcc gtc ggt gct gtg gtc acc ctg gac agc      8739
Val Gln Pro Gln Ala Ser Val Gly Ala Val Val Thr Leu Asp Ser
2900            2905                2910 agc aac cct gcg gcc ggg ctg cat ctg cag ctc aac tat acg ctg      8784
Ser Asn Pro Ala Ala Gly Leu His Leu Gln Leu Asn Tyr Thr Leu
        2915            2920                2925 ctg gac ggc cac tac ctg tct gag gaa cct gag ccc tac ctg gca      8829
Leu Asp Gly His Tyr Leu Ser Glu Glu Pro Glu Pro Tyr Leu Ala
2930            2935                2940 gtc tac cta cac tcg gag ccc cgg ccc aat gag cac aac tgc tcg      8874
Val Tyr Leu His Ser Glu Pro Arg Pro Asn Glu His Asn Cys Ser
        2945            2950                2955 gct agc agg agg atc cgc cca gag tca ctc cag ggt gct gac cac      8919
Ala Ser Arg Arg Ile Arg Pro Glu Ser Leu Gln Gly Ala Asp His
2960            2965                2970 cgg ccc tac acc ttc ttc att tcc ccg ggg agc aga gac cca gcg      8964
Arg Pro Tyr Thr Phe Phe Ile Ser Pro Gly Ser Arg Asp Pro Ala
        2975            2980                2985 ggg agt tac cat ctg aac ctc tcc agc cac ttc cgc tgg tcg gcg      9009
Gly Ser Tyr His Leu Asn Leu Ser Ser His Phe Arg Trp Ser Ala
2990            2995                3000 ctg cag gtg tcc gtg ggc ctg tac acg tcc ctg tgc cag tac ttc      9054
Leu Gln Val Ser Val Gly Leu Tyr Thr Ser Leu Cys Gln Tyr Phe
        3005            3010                3015 agc gag gag gac atg gtg tgg cgg aca gag ggg ctg ctg ccc ctg      9099
Ser Glu Glu Asp Met Val Trp Arg Thr Glu Gly Leu Leu Pro Leu
3020            3025                3030
```

-continued

| | | | | | | | | | | | | | | |
|---|---|---|---|---|---|---|---|---|---|---|---|---|---|---|
| gag | gag | acc | tcg | ccc | cgc | cag | gcc | gtc | tgc | ctc | acc | cgc | cac | ctc | 9144 |
| Glu | Glu | Thr | Ser | Pro | Arg | Gln | Ala | Val | Cys | Leu | Thr | Arg | His | Leu | |
| | 3035 | | | | 3040 | | | | | 3045 | | | | | |

| acc | gcc | ttc | ggc | gcc | agc | ctc | ttc | gtg | ccc | cca | agc | cat | gtc | cgc | 9189 |
| Thr | Ala | Phe | Gly | Ala | Ser | Leu | Phe | Val | Pro | Pro | Ser | His | Val | Arg | |
| 3050 | | | | | 3055 | | | | | 3060 | | | | | |

| ttt | gtg | ttt | cct | gag | ccg | aca | gcg | gat | gta | aac | tac | atc | gtc | atg | 9234 |
| Phe | Val | Phe | Pro | Glu | Pro | Thr | Ala | Asp | Val | Asn | Tyr | Ile | Val | Met | |
| 3065 | | | | | 3070 | | | | | 3075 | | | | | |

| ctg | aca | tgt | gct | gtg | tgc | ctg | gtg | acc | tac | atg | gtc | atg | gcc | gcc | 9279 |
| Leu | Thr | Cys | Ala | Val | Cys | Leu | Val | Thr | Tyr | Met | Val | Met | Ala | Ala | |
| | 3080 | | | | 3085 | | | | | 3090 | | | | | |

| atc | ctg | cac | aag | ctg | gac | cag | ttg | gat | gcc | agc | cgg | ggc | cgc | gcc | 9324 |
| Ile | Leu | His | Lys | Leu | Asp | Gln | Leu | Asp | Ala | Ser | Arg | Gly | Arg | Ala | |
| 3095 | | | | | 3100 | | | | | 3105 | | | | | |

| atc | cct | ttc | tgt | ggg | cag | cgg | ggc | cgc | ttc | aag | tac | gag | atc | ctc | 9369 |
| Ile | Pro | Phe | Cys | Gly | Gln | Arg | Gly | Arg | Phe | Lys | Tyr | Glu | Ile | Leu | |
| 3110 | | | | | 3115 | | | | | 3120 | | | | | |

| gtc | aag | aca | ggc | tgg | ggc | cgg | ggc | tca | ggt | acc | acg | gcc | cac | gtg | 9414 |
| Val | Lys | Thr | Gly | Trp | Gly | Arg | Gly | Ser | Gly | Thr | Thr | Ala | His | Val | |
| 3125 | | | | | 3130 | | | | | 3135 | | | | | |

| ggc | atc | atg | ctg | tat | ggg | gtg | gac | agc | cgg | agc | ggc | cac | cgg | cac | 9459 |
| Gly | Ile | Met | Leu | Tyr | Gly | Val | Asp | Ser | Arg | Ser | Gly | His | Arg | His | |
| 3140 | | | | | 3145 | | | | | 3150 | | | | | |

| ctg | gac | ggc | gac | aga | gcc | ttc | cac | cgc | aac | agc | ctg | gac | atc | ttc | 9504 |
| Leu | Asp | Gly | Asp | Arg | Ala | Phe | His | Arg | Asn | Ser | Leu | Asp | Ile | Phe | |
| 3155 | | | | | 3160 | | | | | 3165 | | | | | |

| cgg | atc | gcc | acc | ccg | cac | agc | ctg | ggt | agc | gtg | tgg | aag | atc | cga | 9549 |
| Arg | Ile | Ala | Thr | Pro | His | Ser | Leu | Gly | Ser | Val | Trp | Lys | Ile | Arg | |
| 3170 | | | | | 3175 | | | | | 3180 | | | | | |

| gtg | tgg | cac | gac | aac | aaa | ggg | ctc | agc | cct | gcc | tgg | ttc | ctg | cag | 9594 |
| Val | Trp | His | Asp | Asn | Lys | Gly | Leu | Ser | Pro | Ala | Trp | Phe | Leu | Gln | |
| 3185 | | | | | 3190 | | | | | 3195 | | | | | |

| cac | gtc | atc | gtc | agg | gac | ctg | cag | acg | gca | cgc | agc | gcc | ttc | ttc | 9639 |
| His | Val | Ile | Val | Arg | Asp | Leu | Gln | Thr | Ala | Arg | Ser | Ala | Phe | Phe | |
| 3200 | | | | | 3205 | | | | | 3210 | | | | | |

| ctg | gtc | aat | gac | tgg | ctt | tcg | gtg | gag | acg | gag | gcc | aac | ggg | ggc | 9684 |
| Leu | Val | Asn | Asp | Trp | Leu | Ser | Val | Glu | Thr | Glu | Ala | Asn | Gly | Gly | |
| 3215 | | | | | 3220 | | | | | 3225 | | | | | |

| ctg | gtg | gag | aag | gag | gtg | ctg | gcc | gcg | agc | gac | gca | gcc | ctt | ttg | 9729 |
| Leu | Val | Glu | Lys | Glu | Val | Leu | Ala | Ala | Ser | Asp | Ala | Ala | Leu | Leu | |
| 3230 | | | | | 3235 | | | | | 3240 | | | | | |

| cgc | ttc | cgg | cgc | ctg | ctg | gtg | gct | gag | ctg | cag | cgt | ggc | ttc | ttt | 9774 |
| Arg | Phe | Arg | Arg | Leu | Leu | Val | Ala | Glu | Leu | Gln | Arg | Gly | Phe | Phe | |
| 3245 | | | | | 3250 | | | | | 3255 | | | | | |

| gac | aag | cac | atc | tgg | ctc | tcc | ata | tgg | gac | cgg | ccg | cct | cgt | agc | 9819 |
| Asp | Lys | His | Ile | Trp | Leu | Ser | Ile | Trp | Asp | Arg | Pro | Pro | Arg | Ser | |
| 3260 | | | | | 3265 | | | | | 3270 | | | | | |

| cgt | ttc | act | cgc | atc | cag | agg | gcc | acc | tgc | tgc | gtt | ctc | ctc | atc | 9864 |
| Arg | Phe | Thr | Arg | Ile | Gln | Arg | Ala | Thr | Cys | Cys | Val | Leu | Leu | Ile | |
| 3275 | | | | | 3280 | | | | | 3285 | | | | | |

| tgc | ctc | ttc | ctg | ggc | gcc | aac | gcc | gtg | tgg | tac | ggg | gct | gtt | ggc | 9909 |
| Cys | Leu | Phe | Leu | Gly | Ala | Asn | Ala | Val | Trp | Tyr | Gly | Ala | Val | Gly | |
| 3290 | | | | | 3295 | | | | | 3300 | | | | | |

| gac | tct | gcc | tac | agc | acg | ggg | cat | gtg | tcc | agg | ctg | agc | ccg | ctg | 9954 |
| Asp | Ser | Ala | Tyr | Ser | Thr | Gly | His | Val | Ser | Arg | Leu | Ser | Pro | Leu | |
| 3305 | | | | | 3310 | | | | | 3315 | | | | | |

| agc | gtc | gac | aca | gtc | gct | gtt | ggc | ctg | gtg | tcc | agc | gtg | gtt | gtc | 9999 |
| Ser | Val | Asp | Thr | Val | Ala | Val | Gly | Leu | Val | Ser | Ser | Val | Val | Val | |
| 3320 | | | | | 3325 | | | | | 3330 | | | | | |

-continued

| | | | | | | | | | | | | | | | |
|---|---|---|---|---|---|---|---|---|---|---|---|---|---|---|---|
| tat | ccc | gtc | tac | ctg | gcc | atc | ctt | ttt | ctc | ttc | cgg | atg | tcc | cgg | 10044 |
| Tyr | Pro | Val | Tyr | Leu | Ala | Ile | Leu | Phe | Leu | Phe | Arg | Met | Ser | Arg | |
| | 3335 | | | | 3340 | | | | | 3345 | | | | | |

| | | | | | | | | | | | | | | | |
|---|---|---|---|---|---|---|---|---|---|---|---|---|---|---|---|
| agc | aag | gtg | gct | ggg | agc | ccg | agc | ccc | aca | cct | gcc | ggg | cag | cag | 10089 |
| Ser | Lys | Val | Ala | Gly | Ser | Pro | Ser | Pro | Thr | Pro | Ala | Gly | Gln | Gln | |
| 3350 | | | | | 3355 | | | | | 3360 | | | | | |

| | | | | | | | | | | | | | | | |
|---|---|---|---|---|---|---|---|---|---|---|---|---|---|---|---|
| gtg | ctg | gac | atc | gac | agc | tgc | ctg | gac | tcg | tcc | gtg | ctg | gac | agc | 10134 |
| Val | Leu | Asp | Ile | Asp | Ser | Cys | Leu | Asp | Ser | Ser | Val | Leu | Asp | Ser | |
| 3365 | | | | | 3370 | | | | | 3375 | | | | | |

| | | | | | | | | | | | | | | | |
|---|---|---|---|---|---|---|---|---|---|---|---|---|---|---|---|
| tcc | ttc | ctc | acg | ttc | tca | ggc | ctc | cac | gct | gag | cag | gcc | ttt | gtt | 10179 |
| Ser | Phe | Leu | Thr | Phe | Ser | Gly | Leu | His | Ala | Glu | Gln | Ala | Phe | Val | |
| 3380 | | | | | 3385 | | | | | 3390 | | | | | |

| | | | | | | | | | | | | | | | |
|---|---|---|---|---|---|---|---|---|---|---|---|---|---|---|---|
| gga | cag | atg | aag | agt | gac | ttg | ttt | ctg | gat | gat | tct | aag | agt | ctg | 10224 |
| Gly | Gln | Met | Lys | Ser | Asp | Leu | Phe | Leu | Asp | Asp | Ser | Lys | Ser | Leu | |
| 3395 | | | | | 3400 | | | | | 3405 | | | | | |

| | | | | | | | | | | | | | | | |
|---|---|---|---|---|---|---|---|---|---|---|---|---|---|---|---|
| gtg | tgc | tgg | ccc | tcc | ggc | gag | gga | acg | ctc | agt | tgg | ccg | gac | ctg | 10269 |
| Val | Cys | Trp | Pro | Ser | Gly | Glu | Gly | Thr | Leu | Ser | Trp | Pro | Asp | Leu | |
| 3410 | | | | | 3415 | | | | | 3420 | | | | | |

| | | | | | | | | | | | | | | | |
|---|---|---|---|---|---|---|---|---|---|---|---|---|---|---|---|
| ctc | agt | gac | ccg | tcc | att | gtg | ggt | agc | aat | ctg | cgg | cag | ctg | gca | 10314 |
| Leu | Ser | Asp | Pro | Ser | Ile | Val | Gly | Ser | Asn | Leu | Arg | Gln | Leu | Ala | |
| 3425 | | | | | 3430 | | | | | 3435 | | | | | |

| | | | | | | | | | | | | | | | |
|---|---|---|---|---|---|---|---|---|---|---|---|---|---|---|---|
| cgg | ggc | cag | gcg | ggc | cat | ggg | ctg | ggc | cca | gag | gag | gac | ggc | ttc | 10359 |
| Arg | Gly | Gln | Ala | Gly | His | Gly | Leu | Gly | Pro | Glu | Glu | Asp | Gly | Phe | |
| 3440 | | | | | 3445 | | | | | 3450 | | | | | |

| | | | | | | | | | | | | | | | |
|---|---|---|---|---|---|---|---|---|---|---|---|---|---|---|---|
| tcc | ctg | gcc | agc | ccc | tac | tcg | cct | gcc | aaa | tcc | ttc | tca | gca | tca | 10404 |
| Ser | Leu | Ala | Ser | Pro | Tyr | Ser | Pro | Ala | Lys | Ser | Phe | Ser | Ala | Ser | |
| 3455 | | | | | 3460 | | | | | 3465 | | | | | |

| | | | | | | | | | | | | | | | |
|---|---|---|---|---|---|---|---|---|---|---|---|---|---|---|---|
| gat | gaa | gac | ctg | atc | cag | cag | gtc | ctt | gcc | gag | ggg | gtc | agc | agc | 10449 |
| Asp | Glu | Asp | Leu | Ile | Gln | Gln | Val | Leu | Ala | Glu | Gly | Val | Ser | Ser | |
| 3470 | | | | | 3475 | | | | | 3480 | | | | | |

| | | | | | | | | | | | | | | | |
|---|---|---|---|---|---|---|---|---|---|---|---|---|---|---|---|
| cca | gcc | cct | acc | caa | gac | acc | cac | atg | gaa | acg | gac | ctg | ctc | agc | 10494 |
| Pro | Ala | Pro | Thr | Gln | Asp | Thr | His | Met | Glu | Thr | Asp | Leu | Leu | Ser | |
| 3485 | | | | | 3490 | | | | | 3495 | | | | | |

| | | | | | | | | | | | | | | | |
|---|---|---|---|---|---|---|---|---|---|---|---|---|---|---|---|
| agc | ctg | tcc | agc | act | cct | ggg | gag | aag | aca | gag | acg | ctg | gcg | ctg | 10539 |
| Ser | Leu | Ser | Ser | Thr | Pro | Gly | Glu | Lys | Thr | Glu | Thr | Leu | Ala | Leu | |
| 3500 | | | | | 3505 | | | | | 3510 | | | | | |

| | | | | | | | | | | | | | | | |
|---|---|---|---|---|---|---|---|---|---|---|---|---|---|---|---|
| cag | agg | ctg | ggg | gag | ctg | ggg | cca | ccc | agc | cca | ggc | ctg | aac | tgg | 10584 |
| Gln | Arg | Leu | Gly | Glu | Leu | Gly | Pro | Pro | Ser | Pro | Gly | Leu | Asn | Trp | |
| 3515 | | | | | 3520 | | | | | 3525 | | | | | |

| | | | | | | | | | | | | | | | |
|---|---|---|---|---|---|---|---|---|---|---|---|---|---|---|---|
| gaa | cag | ccc | cag | gca | gcg | agg | ctg | tcc | agg | aca | gga | ctg | gtg | gag | 10629 |
| Glu | Gln | Pro | Gln | Ala | Ala | Arg | Leu | Ser | Arg | Thr | Gly | Leu | Val | Glu | |
| 3530 | | | | | 3535 | | | | | 3540 | | | | | |

| | | | | | | | | | | | | | | | |
|---|---|---|---|---|---|---|---|---|---|---|---|---|---|---|---|
| ggt | ctg | cgg | aag | cgc | ctg | ctg | ccg | gcc | tgg | tgt | gcc | tcc | ctg | gcc | 10674 |
| Gly | Leu | Arg | Lys | Arg | Leu | Leu | Pro | Ala | Trp | Cys | Ala | Ser | Leu | Ala | |
| 3545 | | | | | 3550 | | | | | 3555 | | | | | |

| | | | | | | | | | | | | | | | |
|---|---|---|---|---|---|---|---|---|---|---|---|---|---|---|---|
| cac | ggg | ctc | agc | ctg | ctc | ctg | gtg | gct | gtg | gct | gtg | gct | gtc | tca | 10719 |
| His | Gly | Leu | Ser | Leu | Leu | Leu | Val | Ala | Val | Ala | Val | Ala | Val | Ser | |
| 3560 | | | | | 3565 | | | | | 3570 | | | | | |

| | | | | | | | | | | | | | | | |
|---|---|---|---|---|---|---|---|---|---|---|---|---|---|---|---|
| ggg | tgg | gtg | ggt | gcg | agc | ttc | ccc | ccg | ggc | gtg | agt | gtt | gcg | tgg | 10764 |
| Gly | Trp | Val | Gly | Ala | Ser | Phe | Pro | Pro | Gly | Val | Ser | Val | Ala | Trp | |
| 3575 | | | | | 3580 | | | | | 3585 | | | | | |

| | | | | | | | | | | | | | | | |
|---|---|---|---|---|---|---|---|---|---|---|---|---|---|---|---|
| ctc | ctg | tcc | agc | agc | gcc | agc | ttc | ctg | gcc | tca | ttc | ctc | ggc | tgg | 10809 |
| Leu | Leu | Ser | Ser | Ser | Ala | Ser | Phe | Leu | Ala | Ser | Phe | Leu | Gly | Trp | |
| 3590 | | | | | 3595 | | | | | 3600 | | | | | |

| | | | | | | | | | | | | | | | |
|---|---|---|---|---|---|---|---|---|---|---|---|---|---|---|---|
| gag | cca | ctg | aag | gtc | ttg | ctg | gaa | gcc | ctg | tac | ttc | tca | ctg | gtg | 10854 |
| Glu | Pro | Leu | Lys | Val | Leu | Leu | Glu | Ala | Leu | Tyr | Phe | Ser | Leu | Val | |
| 3605 | | | | | 3610 | | | | | 3615 | | | | | |

| | | | | | | | | | | | | | | | |
|---|---|---|---|---|---|---|---|---|---|---|---|---|---|---|---|
| gcc | aag | cgg | ctg | cac | ccg | gat | gaa | gat | gac | acc | ctg | gta | gag | agc | 10899 |
| Ala | Lys | Arg | Leu | His | Pro | Asp | Glu | Asp | Asp | Thr | Leu | Val | Glu | Ser | |

-continued

| | | | | | | | | | | | | | | |
|---|---|---|---|---|---|---|---|---|---|---|---|---|---|---|
| ccg | gct | gtg | acg | cct | gtg | agc | gca | cgt | gtg | ccc | cgc | gta | cgg | cca | 10944 |
| Pro | Ala | Val | Thr | Pro | Val | Ser | Ala | Arg | Val | Pro | Arg | Val | Arg | Pro | |
| 3635 | | | | 3640 | | | | | 3645 | | | | | | |

| | | | | | | | | | | | | | | | |
|---|---|---|---|---|---|---|---|---|---|---|---|---|---|---|---|
| ccc | cac | ggc | ttt | gca | ctc | ttc | ctg | gcc | aag | gaa | gaa | gcc | cgc | aag | 10989 |
| Pro | His | Gly | Phe | Ala | Leu | Phe | Leu | Ala | Lys | Glu | Glu | Ala | Arg | Lys | |
| 3650 | | | | 3655 | | | | | 3660 | | | | | | |

| | | | | | | | | | | | | | | | |
|---|---|---|---|---|---|---|---|---|---|---|---|---|---|---|---|
| gtc | aag | agg | cta | cat | ggc | atg | ctg | cgg | agc | ctc | ctg | gtg | tac | atg | 11034 |
| Val | Lys | Arg | Leu | His | Gly | Met | Leu | Arg | Ser | Leu | Leu | Val | Tyr | Met | |
| 3665 | | | | 3670 | | | | | 3675 | | | | | | |

| | | | | | | | | | | | | | | | |
|---|---|---|---|---|---|---|---|---|---|---|---|---|---|---|---|
| ctt | ttt | ctg | ctg | gtg | acc | ctg | ctg | gcc | agc | tat | ggg | gat | gcc | tca | 11079 |
| Leu | Phe | Leu | Leu | Val | Thr | Leu | Leu | Ala | Ser | Tyr | Gly | Asp | Ala | Ser | |
| 3680 | | | | 3685 | | | | | 3690 | | | | | | |

| | | | | | | | | | | | | | | | |
|---|---|---|---|---|---|---|---|---|---|---|---|---|---|---|---|
| tgc | cat | ggg | cac | gcc | tac | cgt | ctg | caa | agc | gcc | atc | aag | cag | gag | 11124 |
| Cys | His | Gly | His | Ala | Tyr | Arg | Leu | Gln | Ser | Ala | Ile | Lys | Gln | Glu | |
| 3695 | | | | 3700 | | | | | 3705 | | | | | | |

| | | | | | | | | | | | | | | | |
|---|---|---|---|---|---|---|---|---|---|---|---|---|---|---|---|
| ctg | cac | agc | cgg | gcc | ttc | ctg | gcc | atc | acg | cgg | tct | gag | gag | ctc | 11169 |
| Leu | His | Ser | Arg | Ala | Phe | Leu | Ala | Ile | Thr | Arg | Ser | Glu | Glu | Leu | |
| 3710 | | | | 3715 | | | | | 3720 | | | | | | |

| | | | | | | | | | | | | | | | |
|---|---|---|---|---|---|---|---|---|---|---|---|---|---|---|---|
| tgg | cca | tgg | atg | gcc | cac | gtg | ctg | ctg | ccc | tac | gtc | cac | ggg | aac | 11214 |
| Trp | Pro | Trp | Met | Ala | His | Val | Leu | Leu | Pro | Tyr | Val | His | Gly | Asn | |
| 3725 | | | | 3730 | | | | | 3735 | | | | | | |

| | | | | | | | | | | | | | | | |
|---|---|---|---|---|---|---|---|---|---|---|---|---|---|---|---|
| cag | tcc | agc | cca | gag | ctg | ggg | ccc | cca | cgg | ctg | cgg | cag | gtg | cgg | 11259 |
| Gln | Ser | Ser | Pro | Glu | Leu | Gly | Pro | Pro | Arg | Leu | Arg | Gln | Val | Arg | |
| 3740 | | | | 3745 | | | | | 3750 | | | | | | |

| | | | | | | | | | | | | | | | |
|---|---|---|---|---|---|---|---|---|---|---|---|---|---|---|---|
| ctg | cag | gaa | gca | ctc | tac | cca | gac | cct | ccc | ggc | ccc | agg | gtc | cac | 11304 |
| Leu | Gln | Glu | Ala | Leu | Tyr | Pro | Asp | Pro | Pro | Gly | Pro | Arg | Val | His | |
| 3755 | | | | 3760 | | | | | 3765 | | | | | | |

| | | | | | | | | | | | | | | | |
|---|---|---|---|---|---|---|---|---|---|---|---|---|---|---|---|
| acg | tgc | tcg | gcc | gca | gga | ggc | ttc | agc | acc | agc | gat | tac | gac | gtt | 11349 |
| Thr | Cys | Ser | Ala | Ala | Gly | Gly | Phe | Ser | Thr | Ser | Asp | Tyr | Asp | Val | |
| 3770 | | | | 3775 | | | | | 3780 | | | | | | |

| | | | | | | | | | | | | | | | |
|---|---|---|---|---|---|---|---|---|---|---|---|---|---|---|---|
| ggc | tgg | gag | agt | cct | cac | aat | ggc | tcg | ggg | acg | tgg | gcc | tat | tca | 11394 |
| Gly | Trp | Glu | Ser | Pro | His | Asn | Gly | Ser | Gly | Thr | Trp | Ala | Tyr | Ser | |
| 3785 | | | | 3790 | | | | | 3795 | | | | | | |

| | | | | | | | | | | | | | | | |
|---|---|---|---|---|---|---|---|---|---|---|---|---|---|---|---|
| gcg | ccg | gat | ctg | ctg | ggg | gca | tgg | tcc | tgg | ggc | tcc | tgt | gcc | gtg | 11439 |
| Ala | Pro | Asp | Leu | Leu | Gly | Ala | Trp | Ser | Trp | Gly | Ser | Cys | Ala | Val | |
| 3800 | | | | 3805 | | | | | 3810 | | | | | | |

| | | | | | | | | | | | | | | | |
|---|---|---|---|---|---|---|---|---|---|---|---|---|---|---|---|
| tat | gac | agc | ggg | ggc | tac | gtg | cag | gag | ctg | ggc | ctg | agc | ctg | gag | 11484 |
| Tyr | Asp | Ser | Gly | Gly | Tyr | Val | Gln | Glu | Leu | Gly | Leu | Ser | Leu | Glu | |
| 3815 | | | | 3820 | | | | | 3825 | | | | | | |

| | | | | | | | | | | | | | | | |
|---|---|---|---|---|---|---|---|---|---|---|---|---|---|---|---|
| gag | agc | cgc | gac | cgg | ctg | cgc | ttc | ctg | cag | ctg | cac | aac | tgg | ctg | 11529 |
| Glu | Ser | Arg | Asp | Arg | Leu | Arg | Phe | Leu | Gln | Leu | His | Asn | Trp | Leu | |
| 3830 | | | | 3835 | | | | | 3840 | | | | | | |

| | | | | | | | | | | | | | | | |
|---|---|---|---|---|---|---|---|---|---|---|---|---|---|---|---|
| gac | aac | agg | agc | cgc | gct | gtg | ttc | ctg | gag | ctc | acg | cgc | tac | agc | 11574 |
| Asp | Asn | Arg | Ser | Arg | Ala | Val | Phe | Leu | Glu | Leu | Thr | Arg | Tyr | Ser | |
| 3845 | | | | 3850 | | | | | 3855 | | | | | | |

| | | | | | | | | | | | | | | | |
|---|---|---|---|---|---|---|---|---|---|---|---|---|---|---|---|
| ccg | gcc | gtg | ggg | ctg | cac | gcc | gcc | gtc | acg | ctg | cgc | ctc | gag | ttc | 11619 |
| Pro | Ala | Val | Gly | Leu | His | Ala | Ala | Val | Thr | Leu | Arg | Leu | Glu | Phe | |
| 3860 | | | | 3865 | | | | | 3870 | | | | | | |

| | | | | | | | | | | | | | | | |
|---|---|---|---|---|---|---|---|---|---|---|---|---|---|---|---|
| ccg | gcg | gcc | ggc | cgc | gcc | ctg | gcc | gcc | ctc | agc | gtc | cgc | ccc | ttt | 11664 |
| Pro | Ala | Ala | Gly | Arg | Ala | Leu | Ala | Ala | Leu | Ser | Val | Arg | Pro | Phe | |
| 3875 | | | | 3880 | | | | | 3885 | | | | | | |

| | | | | | | | | | | | | | | | |
|---|---|---|---|---|---|---|---|---|---|---|---|---|---|---|---|
| gcg | ctg | cgc | cgc | ctc | agc | gcg | ggc | ctc | tcg | ctg | cct | ctg | ctc | acc | 11709 |
| Ala | Leu | Arg | Arg | Leu | Ser | Ala | Gly | Leu | Ser | Leu | Pro | Leu | Leu | Thr | |
| 3890 | | | | 3895 | | | | | 3900 | | | | | | |

| | | | | | | | | | | | | | | | |
|---|---|---|---|---|---|---|---|---|---|---|---|---|---|---|---|
| tcg | gtg | tgc | ctg | ctg | ctg | ttc | gcc | gtg | cac | ttc | gcc | gtg | gcc | gag | 11754 |
| Ser | Val | Cys | Leu | Leu | Leu | Phe | Ala | Val | His | Phe | Ala | Val | Ala | Glu | |
| 3905 | | | | 3910 | | | | | 3915 | | | | | | |

| | | | | | | | | | | | | | |
|---|---|---|---|---|---|---|---|---|---|---|---|---|---|
| gcc | cgt | act | tgg | cac | agg | gaa | ggg | cgc | tgg | cgc | gtg | ctg | cgg | ctc | 11799 |

| | | | | | | | | | | | | |
|---|---|---|---|---|---|---|---|---|---|---|---|---|
| Ala | Arg | Thr | Trp | His | Arg | Glu | Gly | Arg | Trp | Arg | Val | Leu Arg Leu |
| | 3920 | | | | 3925 | | | | 3930 | | | |

| gga | gcc | tgg | gcg | cgg | tgg | ctg | ctg | gtg | gcg | ctg | acg | gcg | gcc | acg | 11844 |
|---|---|---|---|---|---|---|---|---|---|---|---|---|---|---|---|
| Gly | Ala | Trp | Ala | Arg | Trp | Leu | Leu | Val | Ala | Leu | Thr | Ala | Ala | Thr | |
| | 3935 | | | | 3940 | | | | 3945 | | | | | | |

| gca | ctg | gta | cgc | ctc | gcc | cag | ctg | ggt | gcc | gct | gac | cgc | cag | tgg | 11889 |
|---|---|---|---|---|---|---|---|---|---|---|---|---|---|---|---|
| Ala | Leu | Val | Arg | Leu | Ala | Gln | Leu | Gly | Ala | Ala | Asp | Arg | Gln | Trp | |
| | 3950 | | | | 3955 | | | | 3960 | | | | | | |

| acc | cgt | ttc | gtg | cgc | ggc | cgc | ccg | cgc | cgc | ttc | act | agc | ttc | gac | 11934 |
|---|---|---|---|---|---|---|---|---|---|---|---|---|---|---|---|
| Thr | Arg | Phe | Val | Arg | Gly | Arg | Pro | Arg | Arg | Phe | Thr | Ser | Phe | Asp | |
| | 3965 | | | | 3970 | | | | 3975 | | | | | | |

| cag | gtg | gcg | cac | gtg | agc | tcc | gca | gcc | cgt | ggc | ctg | gcg | gcc | tcg | 11979 |
|---|---|---|---|---|---|---|---|---|---|---|---|---|---|---|---|
| Gln | Val | Ala | His | Val | Ser | Ser | Ala | Ala | Arg | Gly | Leu | Ala | Ala | Ser | |
| | 3980 | | | | 3985 | | | | 3990 | | | | | | |

| ctg | ctc | ttc | ctg | ctt | ttg | gtc | aag | gct | gcc | cag | cac | gta | cgc | ttc | 12024 |
|---|---|---|---|---|---|---|---|---|---|---|---|---|---|---|---|
| Leu | Leu | Phe | Leu | Leu | Leu | Val | Lys | Ala | Ala | Gln | His | Val | Arg | Phe | |
| | 3995 | | | | 4000 | | | | 4005 | | | | | | |

| gtg | cgc | cag | tgg | tcc | gtc | ttt | ggc | aag | aca | tta | tgc | cga | gct | ctg | 12069 |
|---|---|---|---|---|---|---|---|---|---|---|---|---|---|---|---|
| Val | Arg | Gln | Trp | Ser | Val | Phe | Gly | Lys | Thr | Leu | Cys | Arg | Ala | Leu | |
| | 4010 | | | | 4015 | | | | 4020 | | | | | | |

| cca | gag | ctc | ctg | ggg | gtc | acc | ttg | ggc | ctg | gtg | gtg | ctc | ggg | gta | 12114 |
|---|---|---|---|---|---|---|---|---|---|---|---|---|---|---|---|
| Pro | Glu | Leu | Leu | Gly | Val | Thr | Leu | Gly | Leu | Val | Val | Leu | Gly | Val | |
| | 4025 | | | | 4030 | | | | 4035 | | | | | | |

| gcc | tac | gcc | cag | ctg | gcc | atc | ctg | ctc | gtg | tct | tcc | tgt | gtg | gac | 12159 |
|---|---|---|---|---|---|---|---|---|---|---|---|---|---|---|---|
| Ala | Tyr | Ala | Gln | Leu | Ala | Ile | Leu | Leu | Val | Ser | Ser | Cys | Val | Asp | |
| | 4040 | | | | 4045 | | | | 4050 | | | | | | |

| tcc | ctc | tgg | agc | gtg | gcc | cag | gcc | ctg | ttg | gtg | ctg | tgc | cct | ggg | 12204 |
|---|---|---|---|---|---|---|---|---|---|---|---|---|---|---|---|
| Ser | Leu | Trp | Ser | Val | Ala | Gln | Ala | Leu | Leu | Val | Leu | Cys | Pro | Gly | |
| | 4055 | | | | 4060 | | | | 4065 | | | | | | |

| act | ggg | ctc | tct | acc | ctg | tgt | cct | gcc | gag | tcc | tgg | cac | ctg | tca | 12249 |
|---|---|---|---|---|---|---|---|---|---|---|---|---|---|---|---|
| Thr | Gly | Leu | Ser | Thr | Leu | Cys | Pro | Ala | Glu | Ser | Trp | His | Leu | Ser | |
| | 4070 | | | | 4075 | | | | 4080 | | | | | | |

| ccc | ctg | ctg | tgt | gtg | ggg | ctc | tgg | gca | ctg | cgg | ctg | tgg | ggc | gcc | 12294 |
|---|---|---|---|---|---|---|---|---|---|---|---|---|---|---|---|
| Pro | Leu | Leu | Cys | Val | Gly | Leu | Trp | Ala | Leu | Arg | Leu | Trp | Gly | Ala | |
| | 4085 | | | | 4090 | | | | 4095 | | | | | | |

| cta | cgg | ctg | ggg | gct | gtt | att | ctc | cgc | tgg | cgc | tac | cac | gcc | ttg | 12339 |
|---|---|---|---|---|---|---|---|---|---|---|---|---|---|---|---|
| Leu | Arg | Leu | Gly | Ala | Val | Ile | Leu | Arg | Trp | Arg | Tyr | His | Ala | Leu | |
| | 4100 | | | | 4105 | | | | 4110 | | | | | | |

| cgt | gga | gag | ctg | tac | cgg | ccg | gcc | tgg | gag | ccc | cag | gac | tac | gag | 12384 |
|---|---|---|---|---|---|---|---|---|---|---|---|---|---|---|---|
| Arg | Gly | Glu | Leu | Tyr | Arg | Pro | Ala | Trp | Glu | Pro | Gln | Asp | Tyr | Glu | |
| | 4115 | | | | 4120 | | | | 4125 | | | | | | |

| atg | gtg | gag | ttg | ttc | ctg | cgc | agg | ctg | cgc | ctc | tgg | atg | ggc | ctc | 12429 |
|---|---|---|---|---|---|---|---|---|---|---|---|---|---|---|---|
| Met | Val | Glu | Leu | Phe | Leu | Arg | Arg | Leu | Arg | Leu | Trp | Met | Gly | Leu | |
| | 4130 | | | | 4135 | | | | 4140 | | | | | | |

| agc | aag | gtc | aag | gag | ttc | cgc | cac | aaa | gtc | cgc | ttt | gaa | ggg | atg | 12474 |
|---|---|---|---|---|---|---|---|---|---|---|---|---|---|---|---|
| Ser | Lys | Val | Lys | Glu | Phe | Arg | His | Lys | Val | Arg | Phe | Glu | Gly | Met | |
| | 4145 | | | | 4150 | | | | 4155 | | | | | | |

| gag | ccg | ctg | ccc | tct | cgc | tcc | tcc | agg | ggc | tcc | aag | gta | tcc | ccg | 12519 |
|---|---|---|---|---|---|---|---|---|---|---|---|---|---|---|---|
| Glu | Pro | Leu | Pro | Ser | Arg | Ser | Ser | Arg | Gly | Ser | Lys | Val | Ser | Pro | |
| | 4160 | | | | 4165 | | | | 4170 | | | | | | |

| gat | gtg | ccc | cca | ccc | agc | gct | ggc | tcc | gat | gcc | tcg | cac | ccc | tcc | 12564 |
|---|---|---|---|---|---|---|---|---|---|---|---|---|---|---|---|
| Asp | Val | Pro | Pro | Pro | Ser | Ala | Gly | Ser | Asp | Ala | Ser | His | Pro | Ser | |
| | 4175 | | | | 4180 | | | | 4185 | | | | | | |

| acc | tcc | tcc | agc | cag | ctg | gat | ggg | ctg | agc | gtg | agc | ctg | ggc | cgg | 12609 |
|---|---|---|---|---|---|---|---|---|---|---|---|---|---|---|---|
| Thr | Ser | Ser | Ser | Gln | Leu | Asp | Gly | Leu | Ser | Val | Ser | Leu | Gly | Arg | |
| | 4190 | | | | 4195 | | | | 4200 | | | | | | |

| ctg | ggg | aca | agg | tgt | gag | cct | gag | ccc | tcc | cgc | ctc | caa | gcc | gtg | 12654 |
|---|---|---|---|---|---|---|---|---|---|---|---|---|---|---|---|
| Leu | Gly | Thr | Arg | Cys | Glu | Pro | Glu | Pro | Ser | Arg | Leu | Gln | Ala | Val | |
| | 4205 | | | | 4210 | | | | 4215 | | | | | | |

-continued

| | | | | | | | | | | | | | | |
|---|---|---|---|---|---|---|---|---|---|---|---|---|---|---|
| ttc | gag | gcc | ctg | ctc | acc | cag | ttt | gac | cga | ctc | aac | cag | gcc | aca | 12699 |
| Phe | Glu | Ala | Leu | Leu | Thr | Gln | Phe | Asp | Arg | Leu | Asn | Gln | Ala | Thr | |
| | 4220 | | | | 4225 | | | | | 4230 | | | | | |

| gag | gac | gtc | tac | cag | ctg | gag | cag | cag | ctg | cac | agc | ctg | caa | ggc | 12744 |
| Glu | Asp | Val | Tyr | Gln | Leu | Glu | Gln | Gln | Leu | His | Ser | Leu | Gln | Gly | |
| | 4235 | | | | 4240 | | | | | 4245 | | | | | |

| cgc | agg | agc | agc | cgg | gcg | ccc | gcc | gga | tct | tcc | cgt | ggc | cca | tcc | 12789 |
| Arg | Arg | Ser | Ser | Arg | Ala | Pro | Ala | Gly | Ser | Ser | Arg | Gly | Pro | Ser | |
| | 4250 | | | | 4255 | | | | | 4260 | | | | | |

| ccg | ggc | ctg | cgg | cca | gca | ctg | ccc | agc | cgc | ctt | gcc | cgg | gcc | agt | 12834 |
| Pro | Gly | Leu | Arg | Pro | Ala | Leu | Pro | Ser | Arg | Leu | Ala | Arg | Ala | Ser | |
| | 4265 | | | | 4270 | | | | | 4275 | | | | | |

| cgg | ggt | gtg | gac | ctg | gcc | act | ggc | ccc | agc | agg | aca | ccc | ctt | cgg | 12879 |
| Arg | Gly | Val | Asp | Leu | Ala | Thr | Gly | Pro | Ser | Arg | Thr | Pro | Leu | Arg | |
| | 4280 | | | | 4285 | | | | | 4290 | | | | | |

| gcc | aag | aac | aag | gtc | cac | ccc | agc | agc | act | tag | | | | | 12912 |
| Ala | Lys | Asn | Lys | Val | His | Pro | Ser | Ser | Thr | | | | | | |
| | 4295 | | | | 4300 | | | | | | | | | | |

<210> SEQ ID NO 2
<211> LENGTH: 4303
<212> TYPE: PRT
<213> ORGANISM: Homo sapiens PKD-1 gene

<400> SEQUENCE: 2

Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
                20                  25                  30

Cys Glu Pro Pro Cys Leu Cys Gly Pro Ala Pro Gly Ala Ala Cys Arg
            35                  40                  45

Val Asn Cys Ser Gly Arg Gly Leu Arg Thr Leu Gly Pro Ala Leu Arg
        50                  55                  60

Ile Pro Ala Asp Ala Thr Glu Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Gln Trp Ala Glu Glu Gln Gln
    130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Ala Pro Pro Ala
                245                 250                 255

-continued

```
Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Asp Thr Arg
        290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
                340                 345                 350

Glu Ala Ala Pro Ala Ala Leu Glu Leu Val Cys Pro Ser Ser Val Gln
            355                 360                 365

Ser Asp Glu Ser Leu Asp Leu Ser Ile Gln Asn Arg Gly Gly Ser Gly
        370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
                420                 425                 430

Gln Glu Gln Cys Gln Ala Trp Ala Gly Ala Ala Leu Ala Met Val Asp
            435                 440                 445

Ser Pro Ala Val Gln Arg Phe Leu Val Ser Arg Val Thr Arg Ser Leu
        450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
        515                 520                 525

Val Cys Glu Leu Gln Pro Gly Gly Pro Val Gln Asp Ala Glu Asn Leu
        530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
                580                 585                 590

Glu Phe Gly Thr Gln Glu Leu Arg Arg Pro Ala Gln Leu Arg Leu Gln
            595                 600                 605

Val Tyr Arg Leu Leu Ser Thr Ala Gly Thr Pro Glu Asn Gly Ser Glu
        610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
                660                 665                 670
```

```
Pro Gly Leu Pro Gly Ala Pro Tyr Ala Leu Trp Arg Glu Phe Leu Phe
        675                 680                 685

Ser Val Pro Ala Gly Pro Pro Ala Gln Tyr Ser Val Thr Leu His Gly
        690                 695                 700

Gln Asp Val Leu Met Leu Pro Gly Asp Leu Val Gly Leu Gln His Asp
705                 710                 715                 720

Ala Gly Pro Gly Ala Leu Leu His Cys Ser Ala Pro Gly His Pro
                725                 730                 735

Gly Pro Arg Ala Pro Tyr Leu Ser Ala Asn Ala Ser Ser Trp Leu Pro
        740                 745                 750

His Leu Pro Ala Gln Leu Glu Gly Thr Trp Gly Cys Pro Ala Cys Ala
        755                 760                 765

Leu Arg Leu Leu Ala Gln Arg Glu Gln Leu Thr Val Leu Leu Gly Leu
        770                 775                 780

Arg Pro Asn Pro Gly Leu Arg Leu Pro Gly Arg Tyr Glu Val Arg Ala
785                 790                 795                 800

Glu Val Gly Asn Gly Val Ser Arg His Asn Leu Ser Cys Ser Phe Asp
                805                 810                 815

Val Val Ser Pro Val Ala Gly Leu Arg Val Ile Tyr Pro Ala Pro Arg
        820                 825                 830

Asp Gly Arg Leu Tyr Val Pro Thr Asn Gly Ser Ala Leu Val Leu Gln
        835                 840                 845

Val Asp Ser Gly Ala Asn Ala Thr Ala Thr Ala Arg Trp Pro Gly Gly
        850                 855                 860

Ser Leu Ser Ala Arg Phe Glu Asn Val Cys Pro Ala Leu Val Ala Thr
865                 870                 875                 880

Phe Val Pro Ala Cys Pro Trp Glu Thr Asn Asp Thr Leu Phe Ser Val
                885                 890                 895

Val Ala Leu Pro Trp Leu Ser Glu Gly Glu His Val Val Asp Val Val
            900                 905                 910

Val Glu Asn Ser Ala Ser Arg Ala Asn Leu Ser Leu Arg Val Thr Ala
        915                 920                 925

Glu Glu Pro Ile Cys Gly Leu Arg Ala Thr Pro Ser Pro Glu Ala Arg
        930                 935                 940

Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
                965                 970                 975

Phe Gln Asn Val Val Phe Asn Val Ile Tyr Gln Ser Ala Ala Val Phe
            980                 985                 990

Lys Leu Ser Leu Thr Ala Ser Asn His Val Ser Asn Val Thr Val Asn
        995                 1000                1005

Tyr Asn Val Thr Val Glu Arg Met Asn Arg Met Gln Gly Leu Gln
        1010                1015                1020

Val Ser Thr Val Pro Ala Val Leu Ser Pro Asn Ala Thr Leu Ala
        1025                1030                1035

Leu Thr Ala Gly Val Leu Val Asp Ser Ala Val Glu Val Ala Phe
        1040                1045                1050

Leu Trp Thr Phe Gly Asp Gly Glu Gln Ala Leu His Gln Phe Gln
        1055                1060                1065

Pro Pro Tyr Asn Glu Ser Phe Pro Val Pro Asp Pro Ser Val Ala
        1070                1075                1080

Gln Val Leu Val Glu His Asn Val Thr His Thr Tyr Ala Ala Pro
```

-continued

```
            1085                1090                1095
Gly Glu Tyr Leu Leu Thr Val Leu Ala Ser Asn Ala Phe Glu Asn
        1100                1105                1110
Leu Thr Gln Gln Val Pro Val Ser Val Arg Ala Ser Leu Pro Ser
        1115                1120                1125
Val Ala Val Gly Val Ser Asp Gly Val Leu Val Ala Gly Arg Pro
        1130                1135                1140
Val Thr Phe Tyr Pro His Pro Leu Pro Ser Pro Gly Gly Val Leu
        1145                1150                1155
Tyr Thr Trp Asp Phe Gly Asp Gly Ser Pro Val Leu Thr Gln Ser
        1160                1165                1170
Gln Pro Ala Ala Asn His Thr Tyr Ala Ser Arg Gly Thr Tyr His
        1175                1180                1185
Val Arg Leu Glu Val Asn Asn Thr Val Ser Gly Ala Ala Ala Gln
        1190                1195                1200
Ala Asp Val Arg Val Phe Glu Glu Leu Arg Gly Leu Ser Val Asp
        1205                1210                1215
Met Ser Leu Ala Val Glu Gln Gly Ala Pro Val Val Val Ser Ala
        1220                1225                1230
Ala Val Gln Thr Gly Asp Asn Ile Thr Trp Thr Phe Asp Met Gly
        1235                1240                1245
Asp Gly Thr Val Leu Ser Gly Pro Glu Ala Thr Val Glu His Val
        1250                1255                1260
Tyr Leu Arg Ala Gln Asn Cys Thr Val Thr Val Gly Ala Gly Ser
        1265                1270                1275
Pro Ala Gly His Leu Ala Arg Ser Leu His Val Leu Val Phe Val
        1280                1285                1290
Leu Glu Val Leu Arg Val Glu Pro Ala Ala Cys Ile Pro Thr Gln
        1295                1300                1305
Pro Asp Ala Arg Leu Thr Ala Tyr Val Thr Gly Asn Pro Ala His
        1310                1315                1320
Tyr Leu Phe Asp Trp Thr Phe Gly Asp Gly Ser Ser Asn Thr Thr
        1325                1330                1335
Val Arg Gly Cys Pro Thr Val Thr His Asn Phe Thr Arg Ser Gly
        1340                1345                1350
Thr Phe Pro Leu Ala Leu Val Leu Ser Ser Arg Val Asn Arg Ala
        1355                1360                1365
His Tyr Phe Thr Ser Ile Cys Val Glu Pro Glu Val Gly Asn Val
        1370                1375                1380
Thr Leu Gln Pro Glu Arg Gln Phe Val Gln Leu Gly Asp Glu Ala
        1385                1390                1395
Trp Leu Val Ala Cys Ala Trp Pro Pro Phe Pro Tyr Arg Tyr Thr
        1400                1405                1410
Trp Asp Phe Gly Thr Glu Glu Ala Ala Pro Thr Arg Ala Arg Gly
        1415                1420                1425
Pro Glu Val Thr Phe Ile Tyr Arg Asp Pro Gly Ser Tyr Leu Val
        1430                1435                1440
Thr Val Thr Ala Ser Asn Asn Ile Ser Ala Ala Asn Asp Ser Ala
        1445                1450                1455
Leu Val Glu Val Gln Glu Pro Val Leu Val Thr Ser Ile Lys Val
        1460                1465                1470
Asn Gly Ser Leu Gly Leu Glu Leu Gln Gln Pro Tyr Leu Phe Ser
        1475                1480                1485
```

-continued

```
Ala Val Gly Arg Gly Arg Pro Ala Ser Tyr Leu Trp Asp Leu Gly
    1490                1495                1500

Asp Gly Gly Trp Leu Glu Gly Pro Glu Val Thr His Ala Tyr Asn
    1505                1510                1515

Ser Thr Gly Asp Phe Thr Val Arg Val Ala Gly Trp Asn Glu Val
    1520                1525                1530

Ser Arg Ser Glu Ala Trp Leu Asn Val Thr Val Lys Arg Arg Val
    1535                1540                1545

Arg Gly Leu Val Val Asn Ala Ser Arg Thr Val Val Pro Leu Asn
    1550                1555                1560

Gly Ser Val Ser Phe Ser Thr Ser Leu Glu Ala Gly Ser Asp Val
    1565                1570                1575

Arg Tyr Ser Trp Val Leu Cys Asp Arg Cys Thr Pro Ile Pro Gly
    1580                1585                1590

Gly Pro Thr Ile Ser Tyr Thr Phe Arg Ser Val Gly Thr Phe Asn
    1595                1600                1605

Ile Ile Val Thr Ala Glu Asn Glu Val Gly Ser Ala Gln Asp Ser
    1610                1615                1620

Ile Phe Val Tyr Val Leu Gln Leu Ile Glu Gly Leu Gln Val Val
    1625                1630                1635

Gly Gly Gly Arg Tyr Phe Pro Thr Asn His Thr Val Gln Leu Gln
    1640                1645                1650

Ala Val Val Arg Asp Gly Thr Asn Val Ser Tyr Ser Trp Thr Ala
    1655                1660                1665

Trp Arg Asp Arg Gly Pro Ala Leu Ala Gly Ser Gly Lys Gly Phe
    1670                1675                1680

Ser Leu Thr Val Leu Glu Ala Gly Thr Tyr His Val Gln Leu Arg
    1685                1690                1695

Ala Thr Asn Met Leu Gly Ser Ala Trp Ala Asp Cys Thr Met Asp
    1700                1705                1710

Phe Val Glu Pro Val Gly Trp Leu Met Val Ala Ala Ser Pro Asn
    1715                1720                1725

Pro Ala Ala Val Asn Thr Ser Val Thr Leu Ser Ala Glu Leu Ala
    1730                1735                1740

Gly Gly Ser Gly Val Val Tyr Thr Trp Ser Leu Glu Glu Gly Leu
    1745                1750                1755

Ser Trp Glu Thr Ser Glu Pro Phe Thr Thr His Ser Phe Pro Thr
    1760                1765                1770

Pro Gly Leu His Leu Val Thr Met Thr Ala Gly Asn Pro Leu Gly
    1775                1780                1785

Ser Ala Asn Ala Thr Val Glu Val Asp Val Gln Val Pro Val Ser
    1790                1795                1800

Gly Leu Ser Ile Arg Ala Ser Glu Pro Gly Gly Ser Phe Val Ala
    1805                1810                1815

Ala Gly Ser Ser Val Pro Phe Trp Gly Gln Leu Ala Thr Gly Thr
    1820                1825                1830

Asn Val Ser Trp Cys Trp Ala Val Pro Gly Gly Ser Ser Lys Arg
    1835                1840                1845

Gly Pro His Val Thr Met Val Phe Pro Asp Ala Gly Thr Phe Ser
    1850                1855                1860

Ile Arg Leu Asn Ala Ser Asn Ala Val Ser Trp Val Ser Ala Thr
    1865                1870                1875
```

-continued

| | | | | | | | | | | |
|---|---|---|---|---|---|---|---|---|---|---|
| Tyr | Asn | Leu | Thr | Ala | Glu | Glu | Pro | Ile | Val | Gly | Leu | Val | Leu | Trp |
| 1880 | | | | 1885 | | | | | 1890 | | | | | |

Ala Ser Ser Lys Val Val Ala Pro Gly Gln Leu Val His Phe Gln
1895                1900                1905

Ile Leu Leu Ala Ala Gly Ser Ala Val Thr Phe Arg Leu Gln Val
1910                1915                1920

Gly Gly Ala Asn Pro Glu Val Leu Pro Gly Pro Arg Phe Ser His
1925                1930                1935

Ser Phe Pro Arg Val Gly Asp His Val Ser Val Arg Gly Lys
1940                1945                1950

Asn His Val Ser Trp Ala Gln Ala Gln Val Arg Ile Val Val Leu
1955                1960                1965

Glu Ala Val Ser Gly Leu Gln Val Pro Asn Cys Cys Glu Pro Gly
1970                1975                1980

Ile Ala Thr Gly Thr Glu Arg Asn Phe Thr Ala Arg Val Gln Arg
1985                1990                1995

Gly Ser Arg Val Ala Tyr Ala Trp Tyr Phe Ser Leu Gln Lys Val
2000                2005                2010

Gln Gly Asp Ser Leu Val Ile Leu Ser Gly Arg Asp Val Thr Tyr
2015                2020                2025

Thr Pro Val Ala Ala Gly Leu Leu Glu Ile Gln Val Arg Ala Phe
2030                2035                2040

Asn Ala Leu Gly Ser Glu Asn Arg Thr Leu Val Leu Glu Val Gln
2045                2050                2055

Asp Ala Val Gln Tyr Val Ala Leu Gln Ser Gly Pro Cys Phe Thr
2060                2065                2070

Asn Arg Ser Ala Gln Phe Glu Ala Ala Thr Ser Pro Ser Pro Arg
2075                2080                2085

Arg Val Ala Tyr His Trp Asp Phe Gly Asp Gly Ser Pro Gly Gln
2090                2095                2100

Asp Thr Asp Glu Pro Arg Ala Glu His Ser Tyr Leu Arg Pro Gly
2105                2110                2115

Asp Tyr Arg Val Gln Val Asn Ala Ser Asn Leu Val Ser Phe Phe
2120                2125                2130

Val Ala Gln Ala Thr Val Thr Val Gln Val Leu Ala Cys Arg Glu
2135                2140                2145

Pro Glu Val Asp Val Val Leu Pro Leu Gln Val Leu Met Arg Arg
2150                2155                2160

Ser Gln Arg Asn Tyr Leu Glu Ala His Val Asp Leu Arg Asp Cys
2165                2170                2175

Val Thr Tyr Gln Thr Glu Tyr Arg Trp Glu Val Tyr Arg Thr Ala
2180                2185                2190

Ser Cys Gln Arg Pro Gly Arg Pro Ala Arg Val Ala Leu Pro Gly
2195                2200                2205

Val Asp Val Ser Arg Pro Arg Leu Val Leu Pro Arg Leu Ala Leu
2210                2215                2220

Pro Val Gly His Tyr Cys Phe Val Phe Val Val Ser Phe Gly Asp
2225                2230                2235

Thr Pro Leu Thr Gln Ser Ile Gln Ala Asn Val Thr Val Ala Pro
2240                2245                2250

Glu Arg Leu Val Pro Ile Ile Glu Gly Gly Ser Tyr Arg Val Trp
2255                2260                2265

Ser Asp Thr Arg Asp Leu Val Leu Asp Gly Ser Glu Ser Tyr Asp

-continued

```
            2270                2275                2280
Pro Asn Leu Glu Asp Gly Asp Gln Thr Pro Leu Ser Phe His Trp
    2285                2290                2295
Ala Cys Val Ala Ser Thr Gln Arg Glu Ala Gly Cys Ala Leu
    2300                2305                2310
Asn Phe Gly Pro Arg Gly Ser Ser Thr Val Thr Ile Pro Arg Glu
    2315                2320                2325
Arg Leu Ala Ala Gly Val Glu Tyr Thr Phe Ser Leu Thr Val Trp
    2330                2335                2340
Lys Ala Gly Arg Lys Glu Ala Thr Asn Gln Thr Val Leu Ile
    2345                2350                2355
Arg Ser Gly Arg Val Pro Ile Val Ser Leu Glu Cys Val Ser Cys
    2360                2365                2370
Lys Ala Gln Ala Val Tyr Glu Val Ser Arg Ser Ser Tyr Val Tyr
    2375                2380                2385
Leu Glu Gly Arg Cys Leu Asn Cys Ser Ser Gly Ser Lys Arg Gly
    2390                2395                2400
Arg Trp Ala Ala Arg Thr Phe Ser Asn Lys Thr Leu Val Leu Asp
    2405                2410                2415
Glu Thr Thr Thr Ser Thr Gly Ser Ala Gly Met Arg Leu Val Leu
    2420                2425                2430
Arg Arg Gly Val Leu Arg Asp Gly Glu Gly Tyr Thr Phe Thr Leu
    2435                2440                2445
Thr Val Leu Gly Arg Ser Gly Glu Glu Glu Gly Cys Ala Ser Ile
    2450                2455                2460
Arg Leu Ser Pro Asn Arg Pro Pro Leu Gly Gly Ser Cys Arg Leu
    2465                2470                2475
Phe Pro Leu Gly Ala Val His Ala Leu Thr Thr Lys Val His Phe
    2480                2485                2490
Glu Cys Thr Gly Trp His Asp Ala Glu Asp Ala Gly Ala Pro Leu
    2495                2500                2505
Val Tyr Ala Leu Leu Leu Arg Arg Cys Arg Gln Gly His Cys Glu
    2510                2515                2520
Glu Phe Cys Val Tyr Lys Gly Ser Leu Ser Ser Tyr Gly Ala Val
    2525                2530                2535
Leu Pro Pro Gly Phe Arg Pro His Phe Glu Val Gly Leu Ala Val
    2540                2545                2550
Val Val Gln Asp Gln Leu Gly Ala Ala Val Val Ala Leu Asn Arg
    2555                2560                2565
Ser Leu Ala Ile Thr Leu Pro Glu Pro Asn Gly Ser Ala Thr Gly
    2570                2575                2580
Leu Thr Val Trp Leu His Gly Leu Thr Ala Ser Val Leu Pro Gly
    2585                2590                2595
Leu Leu Arg Gln Ala Asp Pro Gln His Val Ile Glu Tyr Ser Leu
    2600                2605                2610
Ala Leu Val Thr Val Leu Asn Glu Tyr Glu Arg Ala Leu Asp Val
    2615                2620                2625
Ala Ala Glu Pro Lys His Glu Arg Gln His Arg Ala Gln Ile Arg
    2630                2635                2640
Lys Asn Ile Thr Glu Thr Leu Val Ser Leu Arg Val His Thr Val
    2645                2650                2655
Asp Asp Ile Gln Gln Ile Ala Ala Ala Leu Ala Gln Cys Met Gly
    2660                2665                2670
```

```
Pro Ser Arg Glu Leu Val Cys Arg Ser Cys Leu Lys Gln Thr Leu
    2675                2680                2685

His Lys Leu Glu Ala Met Met Leu Ile Leu Gln Ala Glu Thr Thr
2690                2695                2700

Ala Gly Thr Val Thr Pro Thr Ala Ile Gly Asp Ser Ile Leu Asn
    2705                2710                2715

Ile Thr Gly Asp Leu Ile His Leu Ala Ser Ser Asp Val Arg Ala
2720                2725                2730

Pro Gln Pro Ser Glu Leu Gly Ala Glu Ser Pro Ser Arg Met Val
    2735                2740                2745

Ala Ser Gln Ala Tyr Asn Leu Thr Ser Ala Leu Met Arg Ile Leu
2750                2755                2760

Met Arg Ser Arg Val Leu Asn Glu Glu Pro Leu Thr Leu Ala Gly
    2765                2770                2775

Glu Glu Ile Val Ala Gln Gly Lys Arg Ser Asp Pro Arg Ser Leu
2780                2785                2790

Leu Cys Tyr Gly Gly Ala Pro Gly Pro Gly Cys His Phe Ser Ile
    2795                2800                2805

Pro Glu Ala Phe Ser Gly Ala Leu Ala Asn Leu Ser Asp Val Val
2810                2815                2820

Gln Leu Ile Phe Leu Val Asp Ser Asn Pro Phe Pro Phe Gly Tyr
    2825                2830                2835

Ile Ser Asn Tyr Thr Val Ser Thr Lys Val Ala Ser Met Ala Phe
2840                2845                2850

Gln Thr Gln Ala Gly Ala Gln Ile Pro Ile Glu Arg Leu Ala Ser
    2855                2860                2865

Glu Arg Ala Ile Thr Val Lys Val Pro Asn Asn Ser Asp Trp Ala
2870                2875                2880

Ala Arg Gly His Arg Ser Ser Ala Asn Ser Ala Asn Ser Val Val
    2885                2890                2895

Val Gln Pro Gln Ala Ser Val Gly Ala Val Val Thr Leu Asp Ser
2900                2905                2910

Ser Asn Pro Ala Ala Gly Leu His Leu Gln Leu Asn Tyr Thr Leu
    2915                2920                2925

Leu Asp Gly His Tyr Leu Ser Glu Glu Pro Glu Pro Tyr Leu Ala
2930                2935                2940

Val Tyr Leu His Ser Glu Pro Arg Pro Asn Glu His Asn Cys Ser
    2945                2950                2955

Ala Ser Arg Arg Ile Arg Pro Glu Ser Leu Gln Gly Ala Asp His
2960                2965                2970

Arg Pro Tyr Thr Phe Phe Ile Ser Pro Gly Ser Arg Asp Pro Ala
    2975                2980                2985

Gly Ser Tyr His Leu Asn Leu Ser Ser His Phe Arg Trp Ser Ala
2990                2995                3000

Leu Gln Val Ser Val Gly Leu Tyr Thr Ser Leu Cys Gln Tyr Phe
    3005                3010                3015

Ser Glu Glu Asp Met Val Trp Arg Thr Glu Gly Leu Leu Pro Leu
3020                3025                3030

Glu Glu Thr Ser Pro Arg Gln Ala Val Cys Leu Thr Arg His Leu
    3035                3040                3045

Thr Ala Phe Gly Ala Ser Leu Phe Val Pro Pro Ser His Val Arg
3050                3055                3060
```

-continued

```
Phe Val Phe Pro Glu Pro Thr Ala Asp Val Asn Tyr Ile Val Met
    3065            3070            3075

Leu Thr Cys Ala Val Cys Leu Val Thr Tyr Met Val Met Ala Ala
    3080            3085            3090

Ile Leu His Lys Leu Asp Gln Leu Asp Ala Ser Arg Gly Arg Ala
    3095            3100            3105

Ile Pro Phe Cys Gly Gln Arg Gly Arg Phe Lys Tyr Glu Ile Leu
    3110            3115            3120

Val Lys Thr Gly Trp Gly Arg Gly Ser Gly Thr Thr Ala His Val
    3125            3130            3135

Gly Ile Met Leu Tyr Gly Val Asp Ser Arg Ser Gly His Arg His
    3140            3145            3150

Leu Asp Gly Asp Arg Ala Phe His Arg Asn Ser Leu Asp Ile Phe
    3155            3160            3165

Arg Ile Ala Thr Pro His Ser Leu Gly Ser Val Trp Lys Ile Arg
    3170            3175            3180

Val Trp His Asp Asn Lys Gly Leu Ser Pro Ala Trp Phe Leu Gln
    3185            3190            3195

His Val Ile Val Arg Asp Leu Gln Thr Ala Arg Ser Ala Phe Phe
    3200            3205            3210

Leu Val Asn Asp Trp Leu Ser Val Glu Thr Glu Ala Asn Gly Gly
    3215            3220            3225

Leu Val Glu Lys Glu Val Leu Ala Ala Ser Asp Ala Ala Leu Leu
    3230            3235            3240

Arg Phe Arg Arg Leu Leu Val Ala Glu Leu Gln Arg Gly Phe Phe
    3245            3250            3255

Asp Lys His Ile Trp Leu Ser Ile Trp Asp Arg Pro Pro Arg Ser
    3260            3265            3270

Arg Phe Thr Arg Ile Gln Arg Ala Thr Cys Cys Val Leu Leu Ile
    3275            3280            3285

Cys Leu Phe Leu Gly Ala Asn Ala Val Trp Tyr Gly Ala Val Gly
    3290            3295            3300

Asp Ser Ala Tyr Ser Thr Gly His Val Ser Arg Leu Ser Pro Leu
    3305            3310            3315

Ser Val Asp Thr Val Ala Val Gly Leu Val Ser Ser Val Val Val
    3320            3325            3330

Tyr Pro Val Tyr Leu Ala Ile Leu Phe Leu Phe Arg Met Ser Arg
    3335            3340            3345

Ser Lys Val Ala Gly Ser Pro Ser Pro Thr Pro Ala Gly Gln Gln
    3350            3355            3360

Val Leu Asp Ile Asp Ser Cys Leu Asp Ser Ser Val Leu Asp Ser
    3365            3370            3375

Ser Phe Leu Thr Phe Ser Gly Leu His Ala Glu Gln Ala Phe Val
    3380            3385            3390

Gly Gln Met Lys Ser Asp Leu Phe Leu Asp Asp Ser Lys Ser Leu
    3395            3400            3405

Val Cys Trp Pro Ser Gly Glu Gly Thr Leu Ser Trp Pro Asp Leu
    3410            3415            3420

Leu Ser Asp Pro Ser Ile Val Gly Ser Asn Leu Arg Gln Leu Ala
    3425            3430            3435

Arg Gly Gln Ala Gly His Gly Leu Gly Pro Glu Glu Asp Gly Phe
    3440            3445            3450

Ser Leu Ala Ser Pro Tyr Ser Pro Ala Lys Ser Phe Ser Ala Ser
```

-continued

```
            3455                3460                3465

Asp Glu Asp Leu Ile Gln Gln Val Leu Ala Glu Gly Val Ser Ser
        3470                3475                3480

Pro Ala Pro Thr Gln Asp Thr His Met Glu Thr Asp Leu Leu Ser
        3485                3490                3495

Ser Leu Ser Ser Thr Pro Gly Glu Lys Thr Glu Thr Leu Ala Leu
        3500                3505                3510

Gln Arg Leu Gly Glu Leu Gly Pro Pro Ser Pro Gly Leu Asn Trp
        3515                3520                3525

Glu Gln Pro Gln Ala Ala Arg Leu Ser Arg Thr Gly Leu Val Glu
        3530                3535                3540

Gly Leu Arg Lys Arg Leu Leu Pro Ala Trp Cys Ala Ser Leu Ala
        3545                3550                3555

His Gly Leu Ser Leu Leu Leu Val Ala Val Ala Val Ala Val Ser
        3560                3565                3570

Gly Trp Val Gly Ala Ser Phe Pro Pro Gly Val Ser Val Ala Trp
        3575                3580                3585

Leu Leu Ser Ser Ser Ala Ser Phe Leu Ala Ser Phe Leu Gly Trp
        3590                3595                3600

Glu Pro Leu Lys Val Leu Leu Glu Ala Leu Tyr Phe Ser Leu Val
        3605                3610                3615

Ala Lys Arg Leu His Pro Asp Glu Asp Asp Thr Leu Val Glu Ser
        3620                3625                3630

Pro Ala Val Thr Pro Val Ser Ala Arg Val Pro Arg Val Arg Pro
        3635                3640                3645

Pro His Gly Phe Ala Leu Phe Leu Ala Lys Glu Glu Ala Arg Lys
        3650                3655                3660

Val Lys Arg Leu His Gly Met Leu Arg Ser Leu Leu Val Tyr Met
        3665                3670                3675

Leu Phe Leu Leu Val Thr Leu Leu Ala Ser Tyr Gly Asp Ala Ser
        3680                3685                3690

Cys His Gly His Ala Tyr Arg Leu Gln Ser Ala Ile Lys Gln Glu
        3695                3700                3705

Leu His Ser Arg Ala Phe Leu Ala Ile Thr Arg Ser Glu Glu Leu
        3710                3715                3720

Trp Pro Trp Met Ala His Val Leu Leu Pro Tyr Val His Gly Asn
        3725                3730                3735

Gln Ser Ser Pro Glu Leu Gly Pro Pro Arg Leu Arg Gln Val Arg
        3740                3745                3750

Leu Gln Glu Ala Leu Tyr Pro Asp Pro Pro Gly Pro Arg Val His
        3755                3760                3765

Thr Cys Ser Ala Ala Gly Gly Phe Ser Thr Ser Asp Tyr Asp Val
        3770                3775                3780

Gly Trp Glu Ser Pro His Asn Gly Ser Gly Thr Trp Ala Tyr Ser
        3785                3790                3795

Ala Pro Asp Leu Leu Gly Ala Trp Ser Trp Gly Ser Cys Ala Val
        3800                3805                3810

Tyr Asp Ser Gly Gly Tyr Val Gln Glu Leu Gly Leu Ser Leu Glu
        3815                3820                3825

Glu Ser Arg Asp Arg Leu Arg Phe Leu Gln Leu His Asn Trp Leu
        3830                3835                3840

Asp Asn Arg Ser Arg Ala Val Phe Leu Glu Leu Thr Arg Tyr Ser
        3845                3850                3855
```

-continued

Pro Ala Val Gly Leu His Ala Ala Val Thr Leu Arg Leu Glu Phe
3860                3865                3870

Pro Ala Ala Gly Arg Ala Leu Ala Ala Leu Ser Val Arg Pro Phe
3875                3880                3885

Ala Leu Arg Arg Leu Ser Ala Gly Leu Ser Leu Pro Leu Leu Thr
3890                3895                3900

Ser Val Cys Leu Leu Leu Phe Ala Val His Phe Ala Val Ala Glu
3905                3910                3915

Ala Arg Thr Trp His Arg Glu Gly Arg Trp Arg Val Leu Arg Leu
3920                3925                3930

Gly Ala Trp Ala Arg Trp Leu Leu Val Ala Leu Thr Ala Ala Thr
3935                3940                3945

Ala Leu Val Arg Leu Ala Gln Leu Gly Ala Ala Asp Arg Gln Trp
3950                3955                3960

Thr Arg Phe Val Arg Gly Arg Pro Arg Arg Phe Thr Ser Phe Asp
3965                3970                3975

Gln Val Ala His Val Ser Ser Ala Ala Arg Gly Leu Ala Ala Ser
3980                3985                3990

Leu Leu Phe Leu Leu Leu Val Lys Ala Ala Gln His Val Arg Phe
3995                4000                4005

Val Arg Gln Trp Ser Val Phe Gly Lys Thr Leu Cys Arg Ala Leu
4010                4015                4020

Pro Glu Leu Leu Gly Val Thr Leu Gly Leu Val Val Leu Gly Val
4025                4030                4035

Ala Tyr Ala Gln Leu Ala Ile Leu Leu Val Ser Ser Cys Val Asp
4040                4045                4050

Ser Leu Trp Ser Val Ala Gln Ala Leu Leu Val Leu Cys Pro Gly
4055                4060                4065

Thr Gly Leu Ser Thr Leu Cys Pro Ala Glu Ser Trp His Leu Ser
4070                4075                4080

Pro Leu Leu Cys Val Gly Leu Trp Ala Leu Arg Leu Trp Gly Ala
4085                4090                4095

Leu Arg Leu Gly Ala Val Ile Leu Arg Trp Arg Tyr His Ala Leu
4100                4105                4110

Arg Gly Glu Leu Tyr Arg Pro Ala Trp Glu Pro Gln Asp Tyr Glu
4115                4120                4125

Met Val Glu Leu Phe Leu Arg Arg Leu Arg Leu Trp Met Gly Leu
4130                4135                4140

Ser Lys Val Lys Glu Phe Arg His Lys Val Arg Phe Glu Gly Met
4145                4150                4155

Glu Pro Leu Pro Ser Arg Ser Ser Arg Gly Ser Lys Val Ser Pro
4160                4165                4170

Asp Val Pro Pro Pro Ser Ala Gly Ser Asp Ala Ser His Pro Ser
4175                4180                4185

Thr Ser Ser Ser Gln Leu Asp Gly Leu Ser Val Ser Leu Gly Arg
4190                4195                4200

Leu Gly Thr Arg Cys Glu Pro Glu Pro Ser Arg Leu Gln Ala Val
4205                4210                4215

Phe Glu Ala Leu Leu Thr Gln Phe Asp Arg Leu Asn Gln Ala Thr
4220                4225                4230

Glu Asp Val Tyr Gln Leu Glu Gln Gln Leu His Ser Leu Gln Gly
4235                4240                4245

| | | | | | | | | | | |
|---|---|---|---|---|---|---|---|---|---|---|
|Arg|Arg|Ser|Ser|Arg|Ala|Pro|Ala|Gly|Ser|Ser|Arg|Gly|Pro|Ser|
| |4250| | | |4255| | | |4260| |

| | | | | | | | | | | |
|---|---|---|---|---|---|---|---|---|---|---|
|Pro|Gly|Leu|Arg|Pro|Ala|Leu|Pro|Ser|Arg|Leu|Ala|Arg|Ala|Ser|
| |4265| | | |4270| | | |4275| |

|Arg|Gly|Val|Asp|Leu|Ala|Thr|Gly|Pro|Ser|Arg|Thr|Pro|Leu|Arg|
|---|---|---|---|---|---|---|---|---|---|---|---|---|---|---|
| |4280| | | |4285| | | |4290| |

|Ala|Lys|Asn|Lys|Val|His|Pro|Ser|Ser|Thr|
|---|---|---|---|---|---|---|---|---|---|
| |4295| | | |4300| |

<210> SEQ ID NO 3
<211> LENGTH: 12685
<212> TYPE: DNA
<213> ORGANISM: C. Elegans lov-1 gene

<400> SEQUENCE: 3

```
tcaatctttc tccacatcgt ttagccgcca cttctggaat ctctttggtc cagtttcgtg      60
aatagcagag acaggatcat aggagagtgt gtagttgatg actgtttggt tttggtattg     120
accttgagtt tggagcattc tggtggcacg atgatgaagc agattgactt tggcaacagc     180
gctgtggaat agacggaagt ctttttgagt gtcagcaatt gaaactggag caaaatcttt     240
tggttcaaga agacccaagc gacgttttgt ctgaaattaa ataacagaaa ttaaagaaca     300
tctaatagtg agcttgaaaa ataaatacct tgtatttat gtgatcgatt atttcgtaat      360
cattggtctg cttctcactg tcattacgaa tttcctcgaa ctcgaacata attatagtga     420
cgtaaagttg caggacgagc tttgatccgg caatcatata aagcatgatc acaacaaacg     480
caaattgaga aatcggttga atagaggtaa catcaagttt ccaagcatt ccagccaatg      540
ctgtttgaaa ggtagccatt aagctccgat atctggaacc aattttaaa aattgatttc      600
tttcaattaa gttttcatcc tcaccctccc attttatttc ctaaaactgc gtacaataca     660
gagttgaatg tcatgctgaa gaacaggaaa gcaattccaa atgacacaat agctccgaga     720
gcgttatcca gtgtagccgc taatactcca attcttctgt tgaatctcaa gattcgaatc     780
attttacaag aagtgaagaa tacggctccg gcaagacaat aactgaatac aatctcccaa     840
tttctctgtt cagtcaaatt aatgtacgaa tttccattgt ttgcattgaa atcttccatt     900
gctctatttg tggttcgttg gcggatggtg taggctagga ccgatgcaac agcgagagct     960
ccaactatca agtccatgaa gttccatggt gagaagtttc tataaaatgt ctttttgaaa    1020
ctgaagttct cattagaccc accccagtgc cagctgatac acaattttga atggatttct    1080
cgttggtttc attgttgtta tcaccttgta ccgcccatac aagtagaaca caatctcttt    1140
tacaaatatg agaactgaga aaagatgta aagcatctca taatacttga ccacagttcc     1200
atcgcttccc tctgatttga taagtcttac tgattcaacc caactattag gaagataaat    1260
tcctgacttt ggaatctcca ccaacaactg taccaccgaa aagtagttga tttgagcatt    1320
gtatgcagag aactcaatga tgactgctcg agtatgatca tcgatccatc gttccgaatc    1380
aagtttattg aagagagtga tgatttccgc ttgggtacca gacatactga tagtatatcc    1440
acctcctgaa tagctataca gtaggcctga aactgtttca gtggataatt cttcagaagt    1500
cttgtaggtg tattcatctg aagcatctgt tccattctcg gattccagtt cggtccaacc    1560
agcttgcatg tacaaagttt tttcttcgtt tctgaaacct ctctattagt tggaaattga    1620
agatttttac tcacttgctt gtcaactcct ctccacaatc attgatgtat ccttgaaact    1680
gcttgaacat cgtacactct gcactttct ttgtccgaac ctgccgtatc gtacctattc     1740
ccatacttct tgaaacttta tcattcatgt aggctctcat cccgtatgca ggatttccgt    1800
```

-continued

```
cgtaccaaga agccaaaaga gcagtggcca gagattcacg agcccaatcc cagaaatcgt   1860
cagcatgttg gattgacatg aaagtattgt caccgtagtt cttttgattg atgttcaaga   1920
ttgtgctcat ctgaaaataa taagttcatc taaatctatg tgcattaaag tctacctcca   1980
actgatacca atatccatgc cggtctttgc aatagtatgt cagcataacc ataatataca   2040
aagaagcaaa gaaacaaagc atatcacgaa tggttataaa taactgttca tctctcattt   2100
ttcggttttc agtgtctcgg agctttgtaa catcagcaat ttcggttccc agaccttttt   2160
cgattttccc atagggattt cctgaatttc agtaatgaat tctgatagct tcttttttata   2220
aaacttactc aagaacgtct cagctggctt agctcttagc aatgcttcct ccaacttgtt   2280
aatgatttta tgactctttc tggttttcaa aattaaaaac gcccaaatca atcccttaat   2340
tggctcgaac accactgccc atagaatcag actgatcaga aatcggatat agaaagagtt   2400
ggctaaatca tccatcaagc tcattccagc tccagaaata taaataagac ccatgagaac   2460
tggaaatact atgatggtac gtgccatccc agccatgaac atcggccatg aaccactatt   2520
atccttgaat tccggatcct ctctctttcg tttttttgtag tagtaatgtt cactgtggga   2580
acgacatttg gtgcataata aaatgtgcaa tgagttgagg aaagtgataa gaacaccgaa   2640
tccaactccg aatgcaatat cttttatagt gaaagtgaac tcggagacac tcttcgaatc   2700
actgataatc gaattatcgc tcttcagaat tgtgatgcta atcatgctga ccacaacaag   2760
tgagaagatg atactgacag aatagtcttg ccttgacact cgatccctca accgattgcc   2820
tccaccagta aacatggcaa accaggaaat tgtttgagcc agcatatgca tactcattga   2880
ctcatccaaa aaccttcgct tatactccac tcgcgctagt cttttcagtct ctccgtctcc   2940
gtttttagtt ccaagccaat tgttgaaagg gaagtagtag atatcctgag tctgtagatc   3000
tttcacaatt attcgattgc aataccacga ctctcggtga tctagaccag catcgtcaag   3060
ccagagtctc atgtattcca actcgccaag agggctgaaa tattaaattt ggtaaatgat   3120
ttttgatttg aaaacttgaa ttagtccatc aaaaaccaaa acaagttagg gggataaaaa   3180
aaactacacg tccaatctat aattagctca actcacactt gaaccaatca gcgttgtccg   3240
aatttgcata attggttgaa acgtgtgtgg agctaatcgg tattatttat tttaattatt   3300
tttttattgc taaaaatcag cgtcttctaa cttacaatgc cgttgtcatc acaaatcgat   3360
cagtggttcc ccatgaaaac ggaaactccc aattaccatc ttcttctgat ctgaacgatc   3420
ggaaaatctg atccccttca tttccagata aattgaaaca tatcgtacta tccgtagttg   3480
caaacattcg atatccagtc tccacggcaa tcacatacat gtatccatca tgaggctcat   3540
tgtctttcag aaaacgaagt ctcccgcgtg atgcatcttt acgttgacag atgattgcat   3600
tgatggtaag acatccgtaa actactagca tgaaaacagc ggcaatcatc actttcacat   3660
tcttttcgat ttcattcaca ttataattgt aagagaaatc tgcatcaata gttggattga   3720
atgcaccaac agagaacatt gttaaatgat cagttgaaca attaacgaac tgcattcctt   3780
gtccatcact tggatacatt ccttcagaat tgaagcatc cgatgttttc tgatagaagt   3840
aacatccttt actcactgca gcgacttgat aatccattgg tacacttcgt gcaaatgacc   3900
actgcattga atcgtactga ccatagttta caatatccga actatttcca gtgttagtag   3960
agctatttct ttttccaatt ccaataaaga aaagtccagt gttgttgatc aaatttccgg   4020
cggtgacaaa ataattgctt gtcttgttca atgtgttcaa gtcaaagatc cattcatgat   4080
ttgattcaag tgggccagga agactttgga atgatgagaa catgtaggtg tcatcgttgt   4140
```

```
ttggaatttc atagtcttga gatgcaataa tctctacttg aagcgagttg ttccagttag    4200
tggttcgaaa agcatgaaga tctaatatct gataactggc aaagtctcct tgttgcatta    4260
aagttagcac tgcatcatcc tcacttcccc tgccgttcac ataaattgga gcagtagttc    4320
cggttattct aaaaacattt taacttatat tggaaaaatt ataggttatt caataaactt    4380
acggaatgat tatctgattc tcatctttga tatgtgcttc aagtgcacct gaggtaatta    4440
acatatcaaa gttatccaca taagttctcg ggtttgtggc atagcaaact aatccaactt    4500
gaatcagtgt tttatctgtg atctcagcag tattcagagt tgaagcgggc gatggaagtt    4560
tgaatgccca ttcttcacag ttttgagttt ttcctacaat atttgatgca tcatcgataa    4620
cgattaccat tccggttccg tcgacgctat tctaaaaatt tgattgacat tagtgtaaac    4680
tgtaactttt tgattaccga gtagtcataa ggtaagttgc cagttgctat agctctagct    4740
gctagcgtgt tttccagggt atctagtgta gatgcaagtt ggttggctag attttttggcc   4800
tgaatagaat atgaataatt ccaaactcaa aaagttttaa aaactcacga tgttcttctg    4860
gaacattttt gtgacgtaag cagcccattc ttctgacgtc atttcctcca cgtacacaat    4920
attgtctgga tcacttggta gcacgttgta caaggaatca tagttatctg ttgcatattt    4980
caaattggca gctagatcag aagaaagagg attgtcgaga gcaatcttca acgctgatgt    5040
taaagatccc gcaattgaaa ggagagagtt ggatgtctga aaattattat tatgacatct    5100
accaaagttt agtgtatgaa tacatcatta atctctgcat ctgtcatagt cattccatta    5160
tttgtaagaa aatcttgagt attgctaaga atcgtttcaa tttgttgctg ggattcttga    5220
ttcatcaaac tttgcggcac aatatctgga tatttaaaat gatttgtatg catttgtgta    5280
tttattttt tgagttacca attttagttc ccgaaacatc gccttccgtc gaaacttgtc     5340
cattctgaat tacatatcca ttcgttccat ttctaataat caaccctcca tcgattctca    5400
ttttctgtgt gtcagagaat tccattaaag ttctcaaaat taaagttcct atacaaaata    5460
tccattcgag actatactta caccgtatga gtttgagaac cagatgtgta agttccggct    5520
gttatctgaa taccgtaacc tccaagcgcc aaagaaacaa tattgtaggt gggagaactg    5580
atcaccagag ttgtcacaga gtttgacaaa taaagggcgg tggagtctac gaaaaatgag    5640
tagccgctga catcgatgga tgacgctttg gagaagaata gctgcaagaa aagttatttt    5700
gatattaaca actcatcagc aaaagtctta cagttcccga aacggtgaca agtgtttgtt    5760
ccttaatcaa tgattgcaaa tcatcttttgg tgtacgaagc cgtcggtgaa agagtagata   5820
ttgagacagt ttgagataaa gcagagacag ctggaattcc aatgtcctgc ggagacagca    5880
ccattcgcat tgaataactt cccgcgtttg agaacacaag tggagaagta gtttgattga    5940
ataaagcaag gttgacgtct gaattttta gcgtcataac cagaccactc ccattgcata    6000
cttactctca ataactatcg gcatctgaat caacttctta accgtgctcg ctgaggatcc    6060
atctgatgcc acaaccgtga agctgtcagc attgtatgag aaaatggcat tatctgtgtc    6120
tacttcaaca aactttcctg ttccattcgt gcaagttatt gtgtaagtaa ctccaccata    6180
tgatgcagtt actactagtc ctctagatac aatattttga gtagaatgca gttttatcat    6240
tgttccagat tcaatctgaa taaaaattga aaatttcat gtgctctacg atttataaat     6300
ttaccaataa tatgtattga acttctgaga ctgggatatt gaacgaaaat gaagtgttct    6360
tctgacttgt ggatcctact gttgaattgt cataagtgac attccaagca gttacataca    6420
tatcattata actatattcc cctgattgaa catctccaac tccactcatt gtagccatta    6480
tatttccaga aaccagtgat cgtttgtcat ctatttttatc ctgctcaact tgcacagtcc   6540
```

```
ttccatttgt tgcgaacatt ccttggattc cgatggcagc tgctagcata gtgtccgcct    6600
gaacagtttc acataaacta caatgttcta tattcaaaaa gtcttacagt aacggtatct    6660
ccatcaagct gtttataaga tgcccgggta tctcctgtaa ggtatattgt agatccgtaa    6720
atgctgagct gtaagttgaa acaattaac tctcccaacc atcatttct taccgtacac     6780
ctaggcgata ccaatgtata tcccgatgca ataacatatc caaaaataac cgcgtaagtt    6840
ccatcttttg attttgtact tgatactccc aaggtataga ctgtacttcc tttgagagca    6900
agatcgagag aagacagtac ggagttcaag gattgtgcgg aagtcatatt gacatttgct    6960
agtttagtga taacttttgc catttcgtcg gccaattccg aatttgttgt tgcaatattg    7020
tcttgcaatg ttttcaaaac atcaacactt gacatatttc cgactccagg gattttgagg    7080
gtatttgaga gcaaactttg agcaacttcc actagatctg cggcaggtag agatgagatt    7140
tgattgagaa gagagctgct tgtgtttaga gagttgttgg atgcagatcc atccattatc    7200
ccagccagtt ggttcattac atcagctttt tgagcatcta tgatcgcttg ttcagctgca    7260
gaaattggag aaactgttgc aagagagctg cgagttttag tagttcttgt agatggttgc    7320
gcggtagcag agaatgcacc atttgcacca gaggaatcgg aagatccaga cgtatcggag    7380
ccagatgagc tcttggttga aacaccagaa gatccatttg aatctgatcc tgagccagat    7440
gtactaccac cgtctcctaa atgggatcct ggtgtggtag ctgttccaga tcctgtacca    7500
tctccattca atgccgttgt ttttccagag tttaccccgt ccgaacccgt ccctgaagac    7560
cccccctgacc cacttccaga agcggtcgtt cctgatccac cagcccccga tcccgttgat   7620
gattgtccac ttccagatcc agaagtggtt gatctgactg catcacccgt gctaagagtt    7680
gtcgcagatc ctcctgaacc tgttccacca gttcccccag tagctccagt tccaccggtt    7740
ttgccaccgg catcatccga cgagctgaca gtggttggtg gggtttctaa aaattgaatt    7800
ttatgaaaaa aaacagtaa tgcgcttacc agtagttgta gttggaagaa ctacattcat    7860
agtaaagatg tgactggcag attctccaga tgcacgattg gtaacattaa ttaagaattc    7920
ataagttcca gttgcaggta caaagctggt cattgggttg aaagatacgg aggcactata    7980
tgcaccattt tttccaactg taatatagta cataaatgaa aattgataac gttgctaact    8040
agggagtgct ctttgtactc catggaaata tgagtcggaa aactacttt cgggtagttt     8100
atgtcatttt ctacacgatt ctgaaagaaa atcctgccgg ttttgggttt tagtgtgaaa    8160
agtttgcgtt tgaaaatacc accctaaatt cagttgattt aacactacgc gacccatatt    8220
tcatgtgcaa cgggaaagcc aagtacactg aaaactcact ttcaaattt caaagcaaag     8280
tcataatttc ggtggtccag tggataacgg cgggagcggc gccagttttc agtgtacttg    8340
gctttcccgt tgcacatgaa atatgggtcg cgtagtgtta aatcaactga atttagggtg    8400
gtattttcaa acgcaaactt ttcacactaa acccaaaac cggcaggatt ttctttcaga     8460
atcgtgtaga aaatgatatc aactaccgga aaagtagttt tccgactcat atttccatgg    8520
agtacaaaaa gcactcccta gtaggcaaaa tctcacactc tgtcaagcaa ttgctttcct    8580
tcagtaaaac aaatggctga gaagaatcgt ttcgacattg acaggtcata gcagtcttaa    8640
aatattaagg tttttttaa gtaagattga tttgaatatc ttaccgttaa agctccgggc     8700
tctttgtttg gaattggtgt aatataaaat ggattttcag agtaatacac tgtctcgttc    8760
catgtcaaat tttccaatac aaagtcgtaa ggggtttctg tacttgcgtc tggatccaca    8820
gttgttgttc tcatgctatc agatgcactt gatgaatcgg atggtgtttg agataaacca    8880
```

-continued

| | |
|---|---|
| gatgaatctg aagtggatgg agttgagtta gatgagtcta tggtggtgga atctgaagtt | 8940 |
| gtgccagaat ccgatgttga tgtagaactg tcttgtgaag catcagtcgt gctagcttcc | 9000 |
| aaagtcgacg tagattcaat tcctgaagtt gtggaaatgg ctgaactttc ggaagaagat | 9060 |
| ccagttgaag ttgtactggt aacttcggat gtacttgttg aatccgcaac aacattcaat | 9120 |
| gtgaaaatgt ggctgaccac ttgcattgtc gtcaaatccg tcatgttgat tcgaaactca | 9180 |
| taggtgccaa tgccaacaag aaatgtttca attggttgaa ttggaatatt agaagaataa | 9240 |
| gttgcgttta ggaccgtgtt tgctggaaat tcgctttaat tcaataattt caaaaagttt | 9300 |
| gttaatccta cagtagttta agcaagtgga ttccttaatt ataagaaaag gctcagtaga | 9360 |
| cacatttctg cattcaaatg tttggcttct ctaaaatcat tcgtttcatt tggctcaacg | 9420 |
| atttattaaa cccgcctcag taggagtaat ggcattagtt ggtaaaggta caatgttgat | 9480 |
| gctgtcttca ttgtgacgtg tctcgttcca tgacaatcca ctgtccaaga tgaaatcgaa | 9540 |
| ctgatcgact gacaaagtgg aagttgaatc agcagtggta gaactcggac tggaagaagt | 9600 |
| tgtggatgtg tccgagatgg tagttgtact ggaatcagta gtactttctt cggaagttgt | 9660 |
| tgtggattct tgtaaagtag ttgtgctccc agccgacgtt gtcgtagaat cgcttgaacg | 9720 |
| tgtggatgac ggctctgtga ctgtggatgt tgataatgtg gaagatggag ttgatggtgt | 9780 |
| agatgacgta gagcttgcta cagcagatgt agaagattcc gactctatgg tggtggaaga | 9840 |
| atattcctga atataaacgt tcgcatacgt gtagtaaact ttttttatcgt cggttgtcat | 9900 |
| agttgctctg aaggtgtagt ttccaggacc aacgaatgtg ctagcagggt acgtccctcc | 9960 |
| gagacgtggc attgatacac tttctgaata tattgaaaaa atatgtgtaa aaaatctaaa | 10020 |
| taactatcgc ccgaaaaagg tttgcttttt ttccgatttg aagtttttat agaaacgttt | 10080 |
| tcagaattaa agattttgcc tgtctctaat ttataataag tctttataaa caattactcg | 10140 |
| tgaaacatgc tccgtcttta gtggttgaaa cataattaga agatgtaggg cttgtacatt | 10200 |
| cgatggatgt ttgatactga aatacagtgt tacatttgaa taatgcagtc ttcaatattg | 10260 |
| tacttactcc aatgattccg aggccggaat taagcgttag gttcacactt gtggaatcat | 10320 |
| agaacgttgt agttgccttt tctacaaaat agaagtctgg attagttccg tccgagctag | 10380 |
| tagttgtctc agattttgtt gttgttgaac tttgctgagt agacgtggat gattgagtag | 10440 |
| aagaagcggt gcttgacaca gacgaagaag ccgttgaact tggagtggaa gaagaactcg | 10500 |
| atggcccagt agttgatgtt gaaggagcag ttgtgctggt tgttactgta gacgaaggag | 10560 |
| atgtcgatgt ggactcagtg cttgttgggg tcgttacagt agtcgaggag cttgaactag | 10620 |
| atgtcaccgt agaagtcaca ggggatgttg acggggaagt agttacagta ctcgtcgatg | 10680 |
| gttcggttgt tgacgttgaa gcagtcgagg tggtcaaagt agtggttggt tcagttgttg | 10740 |
| taacagtaga agatgtagat gtaacttctg ttgtggttgt ggaagtagat ggttcttcgg | 10800 |
| tagtagtgga tgtcaacata gtggtggtga agtggtagac gtagtggtc tcgtcaaggt | 10860 |
| aggagcaaat cgcattatcc gggagagacg acaaagttgc tgaaaatttt cgttaaggat | 10920 |
| tttctggata actaacaatg cacaacaagg tgatcggtaa tagtgactgc tttgttttac | 10980 |
| cctgagcaaa ctgtaattgt ataaaatctg aaatattggc aatacaaacg ggtttgaaga | 11040 |
| aaattattaa caatttatt cctgcctctc aatcataaca gcaaattctg gtttgcttgt | 11100 |
| aattattatt gtgcgtccga aactcacatg tgatttcggg tgttgtagtg gttggaatac | 11160 |
| ttgtactcag tgtggtggag ctcggcgagc ttgtgattgt gctagaactc tgctgagttg | 11220 |
| tgctagttga tgatgtcgac gtggatgctg tggaagtgaa cgttgttgac gtggattcga | 11280 |

-continued

```
tggtggtgga tgttgatgga gttgatgtgc ttgtgctcat tgcggtagtc accgtacttg    11340
tacttgttgg gacggttgtt gtagatgtca cggtactagt cacggttgtg gtagttggag    11400
ttgtagtcga ggttgaagtt gactcaatag tgtagtcgca agtattatca ccctggaata    11460
aaatgaaagt aaacactatc tgagaaatcg tactcacagc gtctcgtttc attcttctca    11520
aagtaggtga tccagaagtc ctcatgctaa actgttttgc cctgacaccc ttaagtacct    11580
gcccatcata atacactcct tgactatcac tgatagctgt gctcttttca gaacgatctg    11640
aaatactgtt tagccaatgt tcatgagcaa ttaagaactg acaaggtcgc ttgcacattc    11700
ttctcgcata ctcttcgttg atctctccgc tctcacactt ctctcggtag cccagcaacg    11760
ccatctcgtt tccaccgact tggagccacc atagggagcc atcacatctg tcgataccgt    11820
catctgagaa agagtttcta ttaaaatgtt agaaacacat agcactacat atgcaaataa    11880
cgtttcacca gattcagaat gcgcaattca tgcctatctc atagcctacc tatgtgtcta    11940
cctgagtatc tacttgagta ccttgcaaag aagattaatc ggcacaaacc aagtcaagac    12000
tttgttggca taggtcttcc aggtgagtaa cgccgacatt atacataggt acgcacaaaa    12060
ccttccccaa ataataatcc ttaccataac aaacttcata tttcgcctcc acagcaatac    12120
tgatctcatc gtcatcattc acttcattca agtaatcca agttgagttc aaaaagagtc    12180
cgacaagcct ggtctctgtt tggatgcagt tgtgaatctg aataggaaca acaaggtttt    12240
acaactaaaa aaatacacga ctaaccaatt ccaaacttga acttccgta accttgttct    12300 caactgaaag tctattcaat ccgcagctca atttgatttt aacgactcct tgtgaattcc    12360
ttggaactcc tccaattgtt gtgtcatcgt tgtctaatcg aaaagttgcg atcccgtcaa    12420
gaagttggta atgcaatcca tcaatttgta tcttaaaagt agttttattc agcttttcct    12480
tctgagattt ttcactcacc gccgatattg ccagtagcaa tagaacaaag aagtttgact    12540
tcttcatcca atgagctgga aggttatctt gtagaagttt tgtaaaaatt cgcctgaaaa    12600
caaaaatgaa ttcagagcag aaaagacaac aactgaaaaa tgaagttgtc gaaaagcgaa    12660
aaggcgggct gaatcgaagg accat                                         12685
```

<210> SEQ ID NO 4
<211> LENGTH: 3178
<212> TYPE: PRT
<213> ORGANISM: C. Elegans Lov-1 protein

<400> SEQUENCE: 4

```
Met Val Leu Arg Phe Ser Pro Pro Phe Arg Phe Ser Thr Thr Ser Phe
1               5                   10                  15

Phe Ser Cys Cys Leu Phe Cys Ser Glu Phe Ile Phe Val Phe Arg Arg
            20                  25                  30

Ile Phe Thr Lys Leu Leu Gln Asp Asn Leu Pro Ala His Trp Met Lys
        35                  40                  45

Lys Ser Asn Phe Phe Val Leu Leu Leu Ala Ile Ser Ala Ile Gln
    50                  55                  60

Ile Asp Gly Leu His Tyr Gln Leu Leu Asp Gly Ile Ala Thr Phe Arg
65                  70                  75                  80

Leu Asp Asn Asp Asp Thr Thr Ile Gly Gly Val Pro Arg Asn Ser Gln
                85                  90                  95

Gly Val Val Lys Ile Lys Leu Ser Cys Gly Leu Asn Arg Leu Ser Val
            100                 105                 110

Glu Asn Lys Val Thr Glu Val Ser Ser Leu Glu Leu Ile His Asn Cys
```

-continued

```
            115                 120                 125
Ile Gln Thr Glu Thr Arg Leu Val Gly Leu Phe Leu Asn Ser Thr Trp
130                 135                 140
Ile Thr Leu Asn Glu Val Asn Asp Asp Glu Ile Ser Ile Ala Val
145                 150                 155                 160
Glu Ala Lys Tyr Glu Val Cys Tyr Asp Asp Gly Ile Asp Arg Cys Asp
                    165                 170                 175
Gly Ser Leu Trp Trp Leu Gln Val Gly Gly Asn Glu Met Ala Leu Leu
                180                 185                 190
Gly Tyr Arg Glu Lys Cys Glu Ser Gly Glu Ile Asn Glu Glu Tyr Ala
                195                 200                 205
Arg Arg Met Cys Lys Arg Pro Tyr Arg Ser Glu Lys Ser Thr Ala Ile
        210                 215                 220
Ser Asp Ser Gln Gly Val Tyr Tyr Asp Gly Gln Val Leu Lys Gly Val
225                 230                 235                 240
Arg Ala Lys Gln Phe Ser Met Arg Thr Ser Gly Ser Pro Thr Leu Arg
                245                 250                 255
Arg Met Lys Arg Asp Ala Gly Asp Asn Thr Cys Asp Tyr Thr Ile Glu
                260                 265                 270
Ser Thr Ser Thr Ser Thr Thr Thr Pro Thr Thr Thr Val Thr Ser
        275                 280                 285
Thr Val Thr Ser Thr Thr Thr Val Pro Thr Ser Thr Ser Thr Val Thr
        290                 295                 300
Thr Ala Met Ser Thr Ser Thr Ser Thr Pro Ser Thr Ser Thr Thr Ile
305                 310                 315                 320
Glu Ser Thr Ser Thr Thr Phe Thr Ser Thr Ala Ser Thr Ser Thr Ser
                    325                 330                 335
Ser Thr Ser Thr Thr Gln Gln Ser Ser Ser Thr Ile Thr Ser Ser Pro
                340                 345                 350
Ser Ser Thr Thr Leu Ser Thr Ser Ile Pro Thr Thr Thr Thr Pro Glu
                355                 360                 365
Ile Thr Ser Thr Leu Ser Ser Leu Pro Asp Asn Ala Ile Cys Ser Tyr
        370                 375                 380
Leu Asp Glu Thr Thr Thr Ser Thr Thr Phe Thr Thr Thr Met Leu Thr
385                 390                 395                 400
Ser Thr Thr Thr Glu Glu Pro Ser Thr Ser Thr Thr Thr Thr Glu Val
                    405                 410                 415
Thr Ser Thr Ser Ser Thr Val Thr Thr Thr Glu Pro Thr Thr Thr Leu
                420                 425                 430
Thr Thr Ser Thr Ala Ser Thr Ser Thr Thr Glu Pro Ser Thr Ser Thr
                435                 440                 445
Val Thr Thr Ser Pro Ser Thr Ser Pro Val Thr Ser Thr Val Thr Ser
        450                 455                 460
Ser Ser Ser Ser Ser Thr Thr Val Thr Thr Pro Thr Ser Thr Glu Ser
465                 470                 475                 480
Thr Ser Thr Ser Pro Ser Ser Thr Val Thr Thr Ser Thr Thr Ala Pro
                485                 490                 495
Ser Thr Ser Thr Thr Gly Pro Ser Ser Ser Ser Thr Pro Ser Ser
                500                 505                 510
Thr Ala Ser Ser Ser Val Ser Ser Thr Ala Ser Ser Thr Gln Ser Ser
            515                 520                 525
Thr Ser Thr Gln Gln Ser Ser Thr Thr Thr Lys Ser Glu Thr Thr Thr
        530                 535                 540
```

-continued

```
Ser Ser Asp Gly Thr Asn Pro Asp Phe Tyr Phe Val Glu Lys Ala Thr
545                 550                 555                 560

Thr Thr Phe Tyr Asp Ser Thr Ser Val Asn Leu Thr Leu Asn Ser Gly
                565                 570                 575

Leu Gly Ile Ile Gly Tyr Gln Thr Ser Ile Glu Cys Thr Ser Pro Thr
                580                 585                 590

Ser Ser Asn Tyr Val Ser Thr Thr Lys Asp Gly Ala Cys Phe Thr Lys
                595                 600                 605

Ser Val Ser Met Pro Arg Leu Gly Gly Thr Tyr Pro Ala Ser Thr Phe
            610                 615                 620

Val Gly Pro Gly Asn Tyr Thr Phe Arg Ala Thr Met Thr Thr Asp Asp
625                 630                 635                 640

Lys Lys Val Tyr Tyr Thr Tyr Ala Asn Val Tyr Ile Gln Glu Tyr Ser
                645                 650                 655

Ser Thr Thr Ile Glu Ser Glu Ser Ser Thr Ser Ala Val Ala Ser Ser
                660                 665                 670

Thr Ser Ser Thr Pro Ser Thr Pro Ser Ser Thr Leu Ser Thr Ser Thr
            675                 680                 685

Val Thr Glu Pro Ser Ser Thr Arg Ser Ser Asp Ser Thr Thr Thr Ser
690                 695                 700

Ala Gly Ser Thr Thr Thr Leu Gln Glu Ser Thr Thr Thr Ser Glu Glu
705                 710                 715                 720

Ser Thr Thr Asp Ser Ser Thr Thr Ile Ser Asp Thr Ser Thr Ser
            725                 730                 735

Thr Ser Ser Pro Ser Ser Thr Thr Ala Asp Ser Thr Ser Thr Leu Ser
            740                 745                 750

Val Asp Gln Phe Asp Phe Ile Leu Asp Ser Gly Leu Ser Trp Asn Glu
            755                 760                 765

Thr Arg His Asn Glu Asp Ser Ile Asn Ile Val Pro Leu Pro Thr Asn
            770                 775                 780

Ala Ile Thr Pro Thr Glu Arg Ser Gln Thr Phe Glu Cys Arg Asn Val
785                 790                 795                 800

Ser Thr Glu Pro Phe Leu Ile Ile Lys Glu Ser Thr Cys Leu Asn Tyr
                805                 810                 815

Ser Asn Thr Val Leu Asn Ala Thr Tyr Ser Ser Asn Ile Pro Ile Gln
            820                 825                 830

Pro Ile Glu Thr Phe Leu Val Gly Ile Gly Thr Tyr Glu Phe Arg Ile
            835                 840                 845

Asn Met Thr Asp Leu Thr Thr Met Gln Val Val Ser His Ile Phe Thr
    850                 855                 860

Leu Asn Val Val Ala Asp Ser Thr Ser Thr Ser Glu Val Thr Ser Thr
865                 870                 875                 880

Thr Ser Thr Gly Ser Ser Ser Glu Ser Ser Ala Ile Ser Thr Thr Ser
                885                 890                 895

Gly Ile Glu Ser Thr Ser Thr Leu Glu Ala Ser Thr Thr Asp Ala Ser
                900                 905                 910

Gln Asp Ser Ser Thr Ser Thr Ser Asp Ser Gly Thr Ser Thr Asp Ser
            915                 920                 925

Thr Thr Ile Asp Ser Ser Asn Ser Thr Pro Ser Thr Ser Asp Ser Ser
                930                 935                 940

Gly Leu Ser Gln Thr Pro Ser Asp Ser Ser Ser Ala Ser Asp Ser Met
945                 950                 955                 960
```

-continued

```
Arg Thr Thr Thr Val Asp Pro Asp Ala Ser Thr Glu Thr Pro Tyr Asp
            965                 970                 975
Phe Val Leu Glu Asn Leu Thr Trp Asn Glu Thr Val Tyr Tyr Ser Glu
            980                 985                 990
Asn Pro Phe Tyr Ile Thr Pro Ile Pro Asn Lys Glu Pro Gly Ala Leu
            995                 1000                1005
Thr Thr Ala Met Thr Cys Gln Cys Arg Asn Asp Ser Ser Gln Pro
    1010                1015                1020
Phe Val Leu Leu Lys Glu Ser Asn Cys Leu Thr Glu Phe Gly Lys
    1025                1030                1035
Asn Gly Ala Tyr Ser Ala Ser Val Ser Phe Asn Pro Met Thr Ser
    1040                1045                1050
Phe Val Pro Ala Thr Gly Thr Tyr Glu Phe Leu Ile Asn Val Thr
    1055                1060                1065
Asn Arg Ala Ser Gly Glu Ser Ala Ser His Ile Phe Thr Met Asn
    1070                1075                1080
Val Val Leu Pro Thr Thr Thr Glu Thr Pro Pro Thr Thr Val
    1085                1090                1095
Ser Ser Ser Asp Asp Ala Gly Gly Lys Thr Gly Gly Thr Gly Ala
    1100                1105                1110
Thr Gly Gly Thr Gly Gly Thr Gly Ser Gly Gly Ser Ala Thr Thr
    1115                1120                1125
Leu Ser Thr Gly Asp Ala Val Arg Ser Thr Thr Ser Gly Ser Gly
    1130                1135                1140
Ser Gly Gln Ser Ser Thr Gly Ser Gly Ala Gly Gly Ser Gly Thr
    1145                1150                1155
Thr Ala Ser Gly Ser Gly Ser Gly Gly Ser Ser Gly Thr Gly Ser
    1160                1165                1170
Asp Gly Val Asn Ser Gly Lys Thr Thr Ala Leu Asn Gly Asp Gly
    1175                1180                1185
Thr Gly Ser Gly Thr Ala Thr Thr Pro Gly Ser His Leu Gly Asp
    1190                1195                1200
Gly Gly Ser Thr Ser Gly Ser Gly Ser Asp Ser Asn Gly Ser Ser
    1205                1210                1215
Gly Val Ser Thr Lys Ser Ser Ser Gly Ser Asp Thr Ser Gly Ser
    1220                1225                1230
Ser Asp Ser Ser Gly Ala Asn Gly Ala Phe Ser Ala Thr Ala Gln
    1235                1240                1245
Pro Ser Thr Arg Thr Thr Lys Thr Arg Ser Ser Leu Ala Thr Val
    1250                1255                1260
Ser Pro Ile Ser Ala Ala Glu Gln Ala Ile Ile Asp Ala Gln Lys
    1265                1270                1275
Ala Asp Val Met Asn Gln Leu Ala Gly Ile Met Asp Gly Ser Ala
    1280                1285                1290
Ser Asn Asn Ser Leu Asn Thr Ser Ser Ser Leu Leu Asn Gln Ile
    1295                1300                1305
Ser Ser Leu Pro Ala Ala Asp Leu Val Glu Val Ala Gln Ser Leu
    1310                1315                1320
Leu Ser Asn Thr Leu Lys Ile Pro Gly Val Gly Asn Met Ser Ser
    1325                1330                1335
Val Asp Val Leu Lys Thr Leu Gln Asp Asn Ile Ala Thr Thr Asn
    1340                1345                1350
Ser Glu Leu Ala Asp Glu Met Ala Lys Val Ile Thr Lys Leu Ala
```

-continued

```
                1355                1360                1365

Asn Val Asn Met Thr Ser Ala Gln Ser Leu Asn Ser Val Leu Ser
        1370                1375                1380

Ser Leu Asp Leu Ala Leu Lys Gly Ser Thr Val Tyr Thr Leu Gly
        1385                1390                1395

Val Ser Ser Thr Lys Ser Lys Asp Gly Thr Tyr Ala Val Ile Phe
        1400                1405                1410

Gly Tyr Val Ile Ala Ser Gly Tyr Thr Leu Val Ser Pro Arg Cys
        1415                1420                1425

Thr Leu Ser Ile Tyr Gly Ser Thr Ile Tyr Leu Thr Gly Asp Thr
        1430                1435                1440

Arg Ala Ser Tyr Lys Gln Leu Asp Gly Asp Thr Val Thr Ala Asp
        1445                1450                1455

Thr Met Leu Ala Ala Ala Ile Gly Ile Gln Gly Met Phe Ala Thr
        1460                1465                1470

Asn Gly Arg Thr Val Gln Val Glu Gln Asp Lys Ile Asp Asp Lys
        1475                1480                1485

Arg Ser Leu Val Ser Gly Asn Ile Met Ala Thr Met Ser Gly Val
        1490                1495                1500

Gly Asp Val Gln Ser Gly Glu Tyr Ser Tyr Asn Asp Met Tyr Val
        1505                1510                1515

Thr Ala Trp Asn Val Thr Tyr Asp Asn Ser Thr Val Gly Ser Thr
        1520                1525                1530

Ser Gln Lys Asn Thr Ser Phe Ser Phe Asn Ile Pro Val Ser Glu
        1535                1540                1545

Val Gln Tyr Ile Leu Leu Ile Glu Ser Gly Thr Met Ile Lys Leu
        1550                1555                1560

His Ser Thr Gln Asn Ile Val Ser Arg Gly Leu Val Val Thr Ala
        1565                1570                1575

Ser Tyr Gly Gly Val Thr Tyr Thr Ile Thr Cys Thr Asn Gly Thr
        1580                1585                1590

Gly Lys Phe Val Glu Val Asp Thr Asp Asn Ala Ile Phe Ser Tyr
        1595                1600                1605

Asn Ala Asp Ser Phe Thr Val Val Ala Ser Asp Gly Ser Ser Ala
        1610                1615                1620

Ser Thr Val Lys Lys Leu Ile Gln Met Pro Ile Val Ile Glu Asn
        1625                1630                1635

Val Asn Leu Ala Leu Phe Asn Gln Thr Thr Ser Pro Leu Val Phe
        1640                1645                1650

Ser Asn Ala Gly Ser Tyr Ser Met Arg Met Val Leu Ser Pro Gln
        1655                1660                1665

Asp Ile Gly Ile Pro Ala Val Ser Ala Leu Ser Gln Thr Val Ser
        1670                1675                1680

Ile Ser Thr Leu Ser Pro Thr Ala Ser Tyr Thr Lys Asp Asp Leu
        1685                1690                1695

Gln Ser Leu Ile Lys Glu Gln Thr Leu Val Thr Val Ser Gly Thr
        1700                1705                1710

Thr Ser Asn Ser Leu Leu Ser Ile Ala Gly Ser Leu Thr Ser Ala
        1715                1720                1725

Leu Lys Ile Ala Leu Asp Asn Pro Leu Ser Ser Asp Leu Ala Ala
        1730                1735                1740

Asn Leu Lys Tyr Ala Thr Asp Asn Tyr Asp Ser Leu Tyr Asn Val
        1745                1750                1755
```

-continued

Leu Pro Ser Asp Pro Asp Asn Ile Val Tyr Val Glu Glu Met Thr
    1760            1765            1770

Ser Glu Glu Trp Ala Ala Tyr Val Thr Lys Met Phe Gln Lys Asn
    1775            1780            1785

Ile Ala Lys Asn Leu Ala Asn Gln Leu Ala Ser Thr Leu Asp Thr
    1790            1795            1800

Leu Glu Asn Thr Leu Ala Ala Arg Ala Ile Ala Thr Gly Asn Leu
    1805            1810            1815

Pro Tyr Asp Tyr Ser Asn Ser Val Asp Gly Thr Gly Met Val Ile
    1820            1825            1830

Val Ile Asp Asp Ala Ser Asn Ile Val Gly Lys Thr Gln Asn Cys
    1835            1840            1845

Glu Glu Trp Ala Phe Lys Leu Pro Ser Pro Ala Ser Thr Leu Asn
    1850            1855            1860

Thr Ala Glu Ile Thr Asp Lys Thr Leu Ile Gln Val Gly Leu Val
    1865            1870            1875

Cys Tyr Ala Thr Asn Pro Arg Thr Tyr Val Asp Asn Phe Asp Met
    1880            1885            1890

Leu Ile Thr Ser Gly Ala Leu Glu Ala His Ile Lys Asp Glu Asn
    1895            1900            1905

Gln Ile Ile Ile Pro Ile Thr Gly Thr Thr Ala Pro Ile Tyr Val
    1910            1915            1920

Asn Gly Arg Gly Ser Glu Asp Asp Ala Val Leu Thr Leu Met Gln
    1925            1930            1935

Gln Gly Asp Phe Ala Ser Tyr Gln Ile Leu Asp Leu His Ala Phe
    1940            1945            1950

Arg Thr Thr Asn Trp Asn Asn Ser Leu Gln Val Glu Ile Ile Ala
    1955            1960            1965

Ser Gln Asp Tyr Glu Ile Pro Asn Asn Asp Asp Thr Tyr Met Phe
    1970            1975            1980

Ser Ser Phe Gln Ser Leu Pro Gly Pro Leu Glu Ser Asn His Glu
    1985            1990            1995

Trp Ile Phe Asp Leu Asn Thr Leu Asn Lys Thr Ser Asn Tyr Phe
    2000            2005            2010

Val Thr Ala Gly Asn Leu Ile Asn Asn Thr Gly Leu Phe Phe Ile
    2015            2020            2025

Gly Ile Gly Lys Arg Asn Ser Ser Thr Asn Thr Gly Asn Ser Ser
    2030            2035            2040

Asp Ile Val Asn Tyr Gly Gln Tyr Asp Ser Met Gln Trp Ser Phe
    2045            2050            2055

Ala Arg Ser Val Pro Met Asp Tyr Gln Val Ala Ala Val Ser Lys
    2060            2065            2070

Gly Cys Tyr Phe Tyr Gln Lys Thr Ser Asp Val Phe Asn Ser Glu
    2075            2080            2085

Gly Met Tyr Pro Ser Asp Gly Gln Gly Met Gln Phe Val Asn Cys
    2090            2095            2100

Ser Thr Asp His Leu Thr Met Phe Ser Val Gly Ala Phe Asn Pro
    2105            2110            2115

Thr Ile Asp Ala Asp Phe Ser Tyr Asn Tyr Asn Val Asn Glu Ile
    2120            2125            2130

Glu Lys Asn Val Lys Val Met Ile Ala Ala Val Phe Met Leu Val
    2135            2140            2145

-continued

```
Val Tyr Gly Cys Leu Thr Ile Asn Ala Ile Ile Cys Gln Arg Lys
    2150                2155                2160

Asp Ala Ser Arg Gly Arg Leu Arg Phe Leu Lys Asp Asn Glu Pro
    2165                2170                2175

His Asp Gly Tyr Met Tyr Val Ile Ala Val Glu Thr Gly Tyr Arg
    2180                2185                2190

Met Phe Ala Thr Thr Asp Ser Thr Ile Cys Phe Asn Leu Ser Gly
    2195                2200                2205

Asn Glu Gly Asp Gln Ile Phe Arg Ser Phe Arg Ser Glu Glu Asp
    2210                2215                2220

Gly Asn Trp Glu Phe Pro Phe Ser Trp Gly Thr Thr Asp Arg Phe
    2225                2230                2235

Val Met Thr Thr Ala Phe Pro Leu Gly Glu Leu Glu Tyr Met Arg
    2240                2245                2250

Leu Trp Leu Asp Asp Ala Gly Leu Asp His Arg Glu Ser Trp Tyr
    2255                2260                2265

Cys Asn Arg Ile Ile Val Lys Asp Leu Gln Thr Gln Asp Ile Tyr
    2270                2275                2280

Tyr Phe Pro Phe Asn Asn Trp Leu Gly Thr Lys Asn Gly Asp Gly
    2285                2290                2295

Glu Thr Glu Arg Leu Ala Arg Val Glu Tyr Lys Arg Arg Phe Leu
    2300                2305                2310

Asp Glu Ser Met Ser Met His Met Leu Ala Gln Thr Ile Ser Trp
    2315                2320                2325

Phe Ala Met Phe Thr Gly Gly Gly Asn Arg Leu Arg Asp Arg Val
    2330                2335                2340

Ser Arg Gln Asp Tyr Ser Val Ser Ile Ile Phe Ser Leu Val Val
    2345                2350                2355

Val Ser Met Ile Ser Ile Thr Ile Leu Lys Ser Asp Asn Ser Ile
    2360                2365                2370

Ile Ser Asp Ser Lys Ser Val Ser Glu Phe Thr Phe Thr Ile Lys
    2375                2380                2385

Asp Ile Ala Phe Gly Val Gly Phe Gly Val Leu Ile Thr Phe Leu
    2390                2395                2400

Asn Ser Leu His Ile Leu Leu Cys Thr Lys Cys Arg Ser His Ser
    2405                2410                2415

Glu His Tyr Tyr Tyr Lys Lys Arg Lys Arg Glu Asp Pro Glu Phe
    2420                2425                2430

Lys Asp Asn Ser Gly Ser Trp Pro Met Phe Met Ala Gly Met Ala
    2435                2440                2445

Arg Thr Ile Ile Val Phe Pro Val Leu Met Gly Leu Ile Tyr Ile
    2450                2455                2460

Ser Gly Ala Gly Met Ser Leu Met Asp Asp Leu Ala Asn Ser Phe
    2465                2470                2475

Tyr Ile Arg Phe Leu Ile Ser Leu Ile Leu Trp Ala Val Val Phe
    2480                2485                2490

Glu Pro Ile Lys Gly Leu Ile Trp Ala Phe Leu Ile Leu Lys Thr
    2495                2500                2505

Arg Lys Ser His Lys Ile Ile Asn Lys Leu Glu Glu Ala Leu Leu
    2510                2515                2520

Arg Ala Lys Pro Ala Glu Thr Phe Leu Arg Asn Pro Tyr Gly Lys
    2525                2530                2535

Ile Glu Lys Gly Leu Gly Thr Glu Ile Ala Asp Val Thr Lys Leu
```

-continued

```
            2540                2545                2550
Arg Asp Thr Glu Asn Arg Lys Met Arg Asp Glu Gln Leu Phe Ile
            2555                2560                2565
Thr Ile Arg Asp Met Leu Cys Phe Phe Ala Ser Leu Tyr Ile Met
            2570                2575                2580
Val Met Leu Thr Tyr Tyr Cys Lys Asp Arg His Gly Tyr Trp Tyr
            2585                2590                2595
Gln Leu Glu Met Ser Thr Ile Leu Asn Ile Asn Gln Lys Asn Tyr
            2600                2605                2610
Gly Asp Asn Thr Phe Met Ser Ile Gln His Ala Asp Phe Trp
            2615                2620                2625
Asp Trp Ala Arg Glu Ser Leu Ala Thr Ala Leu Leu Ala Ser Trp
            2630                2635                2640
Tyr Asp Gly Asn Pro Ala Tyr Gly Met Arg Ala Tyr Met Asn Asp
            2645                2650                2655
Lys Val Ser Arg Ser Met Gly Ile Gly Thr Ile Arg Gln Val Arg
            2660                2665                2670
Thr Lys Lys Ser Ala Glu Cys Thr Met Phe Lys Gln Phe Gln Gly
            2675                2680                2685
Tyr Ile Asn Asp Cys Gly Glu Glu Leu Thr Ser Lys Asn Glu Glu
            2690                2695                2700
Lys Thr Leu Tyr Met Gln Ala Gly Trp Thr Glu Leu Glu Ser Glu
            2705                2710                2715
Asn Gly Thr Asp Ala Ser Asp Glu Tyr Thr Tyr Lys Thr Ser Glu
            2720                2725                2730
Glu Leu Ser Thr Glu Thr Val Ser Gly Leu Leu Tyr Ser Tyr Ser
            2735                2740                2745
Gly Gly Gly Tyr Thr Ile Ser Met Ser Gly Thr Gln Ala Glu Ile
            2750                2755                2760
Ile Thr Leu Phe Asn Lys Leu Asp Ser Glu Arg Trp Ile Asp Asp
            2765                2770                2775
His Thr Arg Ala Val Ile Ile Glu Phe Ser Ala Tyr Asn Ala Gln
            2780                2785                2790
Ile Asn Tyr Phe Ser Val Val Gln Leu Leu Val Glu Ile Pro Lys
            2795                2800                2805
Ser Gly Ile Tyr Leu Pro Asn Ser Trp Val Glu Ser Val Arg Leu
            2810                2815                2820
Ile Lys Ser Glu Gly Ser Asp Gly Thr Val Lys Tyr Tyr Glu
            2825                2830                2835
Met Leu Tyr Ile Phe Phe Ser Val Leu Ile Phe Val Lys Glu Ile
            2840                2845                2850
Val Phe Tyr Leu Tyr Gly Arg Tyr Lys Val Ile Thr Thr Met Lys
            2855                2860                2865
Pro Thr Arg Asn Pro Phe Lys Ile Val Tyr Gln Leu Ala Leu Gly
            2870                2875                2880
Asn Phe Ser Pro Trp Asn Phe Met Asp Leu Ile Val Gly Ala Leu
            2885                2890                2895
Ala Val Ala Ser Val Leu Ala Tyr Thr Ile Arg Gln Arg Thr Thr
            2900                2905                2910
Asn Arg Ala Met Glu Asp Phe Asn Ala Asn Gly Asn Ser Tyr
            2915                2920                2925
Ile Asn Leu Thr Glu Gln Arg Asn Trp Glu Ile Val Phe Ser Tyr
            2930                2935                2940
```

```
Cys Leu Ala Gly Ala Val Phe Phe Thr Ser Cys Lys Met Ile Arg
    2945                2950                2955

Ile Leu Arg Phe Asn Arg Arg Ile Gly Val Leu Ala Ala Thr Leu
    2960                2965                2970

Asp Asn Ala Leu Gly Ala Ile Val Ser Phe Gly Ile Ala Phe Leu
    2975                2980                2985

Phe Phe Ser Met Thr Phe Asn Ser Val Leu Tyr Ala Val Leu Gly
    2990                2995                3000

Asn Lys Met Gly Gly Tyr Arg Ser Leu Met Ala Thr Phe Gln Thr
    3005                3010                3015

Ala Leu Ala Gly Met Leu Gly Lys Leu Asp Val Thr Ser Ile Gln
    3020                3025                3030

Pro Ile Ser Gln Phe Ala Phe Val Val Ile Met Leu Tyr Met Ile
    3035                3040                3045

Ala Gly Ser Lys Leu Val Leu Gln Leu Tyr Val Thr Ile Ile Met
    3050                3055                3060

Phe Glu Phe Glu Glu Ile Arg Asn Asp Ser Glu Lys Gln Thr Asn
    3065                3070                3075

Asp Tyr Glu Ile Ile Asp His Ile Lys Tyr Lys Thr Lys Arg Arg
    3080                3085                3090

Leu Gly Leu Leu Glu Pro Lys Asp Phe Ala Pro Val Ser Ile Ala
    3095                3100                3105

Asp Thr Gln Lys Asp Phe Arg Leu Phe His Ser Ala Val Ala Lys
    3110                3115                3120

Val Asn Leu Leu His His Arg Ala Thr Arg Met Leu Gln Thr Gln
    3125                3130                3135

Gly Gln Tyr Gln Asn Gln Thr Val Ile Asn Tyr Thr Leu Ser Tyr
    3140                3145                3150

Asp Pro Val Ser Ala Ile His Glu Thr Gly Pro Lys Arg Phe Gln
    3155                3160                3165

Lys Trp Arg Leu Asn Asp Val Glu Lys Asp
    3170                3175

<210> SEQ ID NO 5
<211> LENGTH: 8073
<212> TYPE: DNA
<213> ORGANISM: C. Elegans pkd-2 gene

<400> SEQUENCE: 5
tcattcttct tttttgtcag caatcgaggt gattgttgga cgacgagcgg cagattcacg    60
gttacggact tggttggtga ggagggcctg gacaagtaaa atatttattg gaaatttaga   120
tatttagcag taacagcaaa attatttgta ttttgttgtt aatttacta aatagtaaaa    180 attgtaagtt ttcattaatt cttattgcca gaataaaaaa ttttctaatt ttgttttgtc   240
taatttgtct aaaactacga aagttttttct ctaaaaattt cactagataa atacaatttt  300
tcatgtttca attactttcc aaaagaagta acactataat tgcattagtt acaattttca   360
actcacactc aaatccatca aatttcctcc atcttgttgt tgaactcttt gttttcgat    420 tgtctggagt gttgcattga ctccttcaat ccgatccaca atgctgaaca ctgattcttg   480
catttgatct acacggcggt tcaaactgaa atgatttacg taatgtttat gatcatttat   540
gatagagctg atacagtaaa agttaccaat ttttgtttct attcttcgga attgtgaaaa   600
aatacaattt tctcatggtt ttcattattt gaaaattcca gtcttcacac gtataaactg   660
```

```
gaacacgaaa aactatgggt tttattctag aatactaatt ttttaatcga taaataatat      720
tatcgtcaaa aaagcataaa gttttttttg taagatatat gaaaatcgaa taacaaaagt      780
taaacttaat caatttatga aaacattgaa ccagtcaaaa atctaattgt gataccgtga      840
aaaaaaaacg tttccctcca aaagtttacc tttttcaagt cttctgttaa caaattttca      900
gaacgtttat atttgtatgg tgacggtgaa acattatttg atcaaaactg ctgtgggaac      960
tgacggttat tatataatta aggttattat ggtaacagtg aaacagtatt taaaaatagc     1020
tgtttcggta ctcaagggt atcccatgag gaaaataaaa gtattacttt ttcagttatg      1080
aaaactgaga atgttttcac aaaatgttac ctgtggtctg tttgggaaaa aggaaatcta     1140
cgatgagaaa tttgcagaac attttttgtc aaaattctct acatgttttt ttttgttgta     1200
cgcagcacag cggaagttca ggtggttatg aaagagtaaa tatttttttt ctgtgatata     1260
aaaaatgttt gcctgtcttg acggctgcgg gccagcacat ttgcctacgt ttcaggtaaa     1320
catgattttt gtaattttcc agtggcatgt aggcccgcag gtaggcaggc ctaacaattt     1380
gaccatttaa agttgtgtac acaataaaat attaattctt taaaatataa tcatttgaaa     1440
attgaaatgc gaaccttcgg ttattatcga attgaatgaa aaacaaaaag aaataattc      1500 taaaaactag ctgaaacatc acaattttcc gtaaaactca ctttgcgtaa tccctgtgat     1560
tctccatata atttctttc tgttccgtca ttctagccac ctcatcagca atatcttcag      1620
ccactttctc cggaacatgc tcagtcattg atgttacatt gaatcgagtg aatgcttcat     1680
tgatgtcttt ttcagcgtat ccggcacggt agagcatcag tttgtagtct tcatacgtgg     1740
catcctctcc aggggcatcc gggcgttttc cacgttttgt gagtcctcga actttctgga     1800
atgaggtatt ttgtggtttt agccaagcgc ccgacgtatt tcgggaactc ttagaatatg     1860
gggcgttgat gaaccctgaa gcacccgaca tattccaggt ttcaacacaa acccagaaaa     1920
tgtccgacgc tagtttaggt acaccaagta acttacattc ataaaccaat ccaaaatccc     1980
ctctccatct ttctttctag ccagctctgc tttcacttca acgtaggaat cattgatgat     2040
agccaagaac atgttcaata ggatgaacga gacgaagaag acgtaggcaa tgaagaaggc     2100
gggtccgaag aatcgattgc aggattctag agccgagaag ttaaagtcac cgagaatgag     2160
acggagcagg gcgaacgcag agttgtagag gttggagtag tcggcgatct tagaaaaatg     2220
tgaagcgccc gacatttacc gggttttgtg taggcaaaac ccggaagatg tcggatgcaa     2280
gaatgtaaca tgccgattag gatacttggt atcactcagt cagataacca ccattttgt    2340 taaaagaaaa tttactgttt cattcaagtt atataagtaa ttggaagatc ccgctgcggt     2400
gaagcgtatt taagattgtt aaaatagctg tgttgatatt tgggtacgtc aaaataaagg     2460
aaatgaatgt tgtaatggat cagacatctg gcgggctcgg tgtaggcaga accaggcaga     2520
tgtcggatgc atgaatgtaa aacgcatccg acatctgccg ggttcttggt tcaaggtaag     2580
cttgataata tttaaaaatg aaaaaaaaac accaggcaga tgtcgggtgc taaaataatt     2640
gctgcgaatt tcccgtttcg taaactttat gagatggaaa tgaatcaaaa tgtcattgta     2700
cctaagaatg cattcgaatg gtagtaaaaa taatgttttt tcatataaaa ttggtgaaac     2760 tgcgatttttt ttctaatttt atattttta aatttcacag caatataaaa cgttacagta     2820
ccccaactat tctaaactcc acgaataaaa caaagatctt aaagattaag ttacctgtgt     2880
cccaaagcac aaatatccaa actgtgcgaa tgcaaaaaag aaaacagcga acatcactgc     2940
aaatcctcca atatccttg cagatctggt caacgtagag acaactgtg acatggtctt      3000 gttaactgag atgaacttga acactttcac ccaagcaaca aataccacac atgctttgat     3060
```

-continued

```
gttcagataa gagttctcgg aagaagtgac gtcatcgaat ggtgcatttg tcaatccgtt    3120
ctcaatgaca gagttgacac gatttactcc ggttttgtg cgattcactg acagaattat     3180
tgtggctact gaaaatccta gcagcacaac gtctaccaaa ttccagaact gggtgagata    3240
gtggagacgg tgacggccga tagcaaaaag ctcctcgaaa atgaagtata gtatgaatcc    3300
acagaagatt ccttcaaaaa tcatcattcg ggtgcctcca gatgtttgat aggtcagaag   3360
atcgtaagtc ataagctttg gagttgtgat aacaccgcca gatgcaggga gctcaaatag    3420
gagtctgaaa tgggaaattt cgaaaaaaat ttaactcgct gcttcagctt tatcataaaa    3480
ttggcgcact tatttgaaaa ttattatctg atcgacattg attggaatgc aaatatttat    3540
aataaatttg ttgacgtaac taaagtttaa aaatccagtt taaaaaaact atgtaaaatt    3600
tcagtactct tgaaactaga caagatttat acttgttttc atttccatag acaccctcac    3660
agttggccgg gtgactgata tgtatggccc gacattttc gggttactgt ggattcatag     3720
ttttcggtgt ggcccattgc aaggcaaagc tagtgcggcg cgaaactcgg aaaacgtcgg    3780
accatgcata tcagtcaaat gccactcgaa tttcgaaatt tttgaatgaa cgtttactct    3840
tgttgaaata cttataatta cagtttcaca aacattgtaa aattttagtc aaaaacgaga    3900
caccattcca ccaaacatga tagaactcac ttcaccacac aaaacagatt aatattcgca    3960
ttgtacagag caaagtccac aataattgca cgtgatcctc tgtcgatcca gcgattagcc   4020
tttaacgtgg caattgcaga ttgagcttca gttgagccag ctactggaag gcgttgaaca    4080
aatccaccac ctccatatga agcaatggtg cccacggttt tcaggttttc aagctctttt    4140
gccgtggcgt agatgaatct gaatataata ttttatttaa aaaaaggatt ggtgagactg     4200
ttttttatag gaattatatg ttgacaataa ctatctaaga ctaacaatta aatgaaaatt    4260
gcatgacaac cataatgttc taaaatttaa aaaaggagc atgaaacatt acgaatatta      4320
gttagaatat ttcaattttc gaggtacttt tcacaaactt tacattttt tcaacgtttt      4380
ttaataagaa tactctttca ggtagttaat atataagcta aattttgcat ttgtgtattg   4440
aagcttttgc aaaaacacat aaacagatat aactgataat ttcttggaac ataaaattgt    4500
attttcatgc aaatttcgta acattctttc aaatacagtt tcataatatt gttaaaaga     4560
aattggggtt ttctcaatag tccataaaat tctaaatatt tttaaaataa aactaagtat    4620
tttccgcaaa taagtcaagt tttgcaataa aatttactgt ttcacattat gatcaagttt    4680
gcatcacaat aagaaataat agtaaaaatt ggttctccat gaaaaaaccc cataaatgcc    4740
atgaaacaac gttagctccg cctttcacca atcgccgatt ggtcagcaga attcaaaagg    4800
tactagaagc tgctgattca acgaccaaac ttggccgaat ttacaaaatt gacgtcactc    4860
acgcatcaac acttccatca ccgaccatcg tcttatcctc gagcttttcc tcataatttg    4920
caaaacattc cttaatctcc cgctggaaac ttttcatcac agtacacgag tcatttgtca    4980
cttttcaacat tctgatccga ggttccccaa gcaaacgatt ctcatagtag atcatattct   5040
cgttatccgt cgaattggaa gtttccgtcc aatatatgcc aggtattagg acttgtgaca    5100
gccactgaaa gtttgatttg aaggttttca tttaaaaatt gaggaaactt acatcccaaa    5160
tattatccat tgaggtacaa gatccaaatg ctggagctcc ggaggcaccg gtgctcgcca   5220
caaacaggtc gctcattact ttggagtagt agtaagattg gatgctgttt tgggcgaacg    5280
caactgtaaa ttttttgaatt tagaaaaaaa aaacccgtga agtgtcgggt gctaactggg    5340
cgtgctcgat atatcacagg attagcccga ctacctgcga ggtgtcgcgc gaaacactag    5400
```

```
atgaaaattt tacaagaaaa tgattttcga aaatacaaac atttgttaac attaattgta   5460 ttttttaagtt gtaaacgcaa aaataaatat tggaaatttg aaaatgtttt gttacaaaaa   5520
ttctgctgtt ttgcttacta agtaaaccta acaaattata ggtaaaaata gtatgtgaac   5580
gtttcatgag gttattcaag tagtgtcgga aaattaaaaa gtgtagaaaa attacgtcac   5640
aactgtatta aaatacataa aaacatgtat tttaatacat ttgtgacgtc acaaatgtat   5700
ttaaatacat tttgctacat tacttgatta accccattaa caaagttgta ctcgtaaaat   5760
ttcagttgaa atgctcaaac tcactaaacg tgttgaggaa aaaaataaa aatttaaaaa   5820 aaaactgttc caccgttgta acaaatgttg tacgcgtttg tcttaaatag tattcggagg   5880
attcagcctg caatggacag ttttcaaaag agaaaattt aactaattgg aagccattta   5940
atcaaaaatt atgaatttag agattacttt gaaaatgta tgattctaaa cgtttctttt   6000
gtgtttattt gcaaaattca aatataagtt tttccacttt tcaaaaccta tttataaaaa   6060
ttagaaaatt aaacaatttt ccaaacaaca ttttttcccg tactgcatta agtaacaac   6120 ataaattgga agattagtaa ctactttggt catagtgttt ccaacaaagt gtggtttta   6180 tgatgctcac aataaatttt tcgatgcca gttgaaacat ttttgaaaaa ttataaaaca   6240
cgaaatgaat atttttgcagt tgatagttac aaatccctgc caaatctttt ttttcacaaa   6300
cttgaatttt aagaaatttg ctaaaaaaaa acttcggctg tttcatacat gccatataat   6360
ttgtaaaaat aaagtgaaaa tcgattcgtc gtgtgtagtt tcgccactca ctataaaatt   6420
gctgattaag tatagtgagt ggcgaaactc ggaaattgtc ggccgccgtg gaaacctacc   6480
ccaaaaccgg acgcagtgcg tccggtggtg ttaaaatcgg acgaccggac gccgatttgt   6540
acagccctat ttgaaagtaa tgacgtcata cttactttca tacagaaatt aaatatctga   6600
tacgttagat tttgggaaat aagcttgtca caaaaaatga tgtggtttat ttctagaagt   6660
cttactatgt agttggtaca caaaatatga aatttgtagc gtatgcttca tagcagttac   6720
aaagtcgaga actatttgta cattaatttg accaacaaac ttaccataaa ccagcacaat   6780
caagaacaca gcgtatccac caacttccat aaacgaacgg gcagtcagct tgatctttcc   6840
atccgatttc tcgtgtccgg atgccagcaa ggcttgagaa aacgagattc cctcttttg   6900 agccggattc ttcttcttat cgtgctcata ctcctcactg accatagaat ggtcaaacga   6960
ggggccatgc tccgcagcgg cgaccggctg cggtggatta gcccatcgct cgtccgcagc   7020
gccgtagttc attgaagacg gctcgctgaa acagtagaaa atttgaatta aagttttgag   7080
aaaagttgaa aatcgagagc tctgtagtgt aaaaactgga aaaatagagt cgaaaagagg   7140
cgagctcgcg aaatccacgt cctcgtagct cttggagatg ccgcattgct aagagatttc   7200
cgtagatact atgttttatg ggatttcacg tttttggttg gagacggttt tttgcataga   7260
aacggaaaaa tgatgcagga atagaaaacg aacatgattt gaaactgaaa accatcgact   7320
atacggcaca atcatactac atttatcggg ttattgaaac tgcatcccaa aagtttacaa   7380
tttaaattca cataccattt gaagataaca acgaataaaa agacttcgaa aggcggcaaa   7440
tgtcgtggtt tcgtggtgta gtggttatca catctgtcta acacacagaa ggtcggtggt   7500
tcgagcccgc ccgagatcat aagttttttg tcaatcatta atattgattc atctgaatga   7560
aattgtaaaa ttcttgaag gtgttctaaa atattgaact gtttttttt agatttcgtt   7620 agtatataat ttttgaaaca tacattttt tcttccaaat ttcaagtatc ttctacgatt   7680
tttgaaaaat cccaaaaatt gtaaacatta aaattctgaa taaacggtgg aaatttgtag   7740
ttctctcaaa ttctaaataa aaattgaacg aaatttgaga aatttcctgt ttcaaaaact   7800
```

-continued

```
aaatgtctta ttttcagagt tcaacaatgc cttagagaaa gttggaaaat gataatgttt    7860
gttagtatat tgagaatatc atgcaagtga aacaattagt ttttttttcg ataacaatta    7920
tttaaaaaaa actactgttt caaatctttt attcaaccaa tcctgtaata aaagttcact    7980
tatcttctcc ctcttcatcc ataatgtatg cccctcttca aatggaaaat atgatgtcgg    8040
ggggaggtcc tccccctccc cacgaccctc cat                                 8073
```

<210> SEQ ID NO 6
<211> LENGTH: 815
<212> TYPE: PRT
<213> ORGANISM: C. Elegans Pkd-2 protein

<400> SEQUENCE: 6

```
Met Glu Gly Arg Gly Glu Gly Glu Asp Leu Pro Pro Thr Ser Tyr Phe
1               5                   10                  15

Pro Phe Glu Glu Gly His Thr Leu Trp Met Lys Arg Glu Lys Ile Lys
            20                  25                  30

His Leu Gln Arg Ile Leu Gln Phe His Ser Asp Glu Ser Ile Leu Met
        35                  40                  45

Ile Asp Lys Lys Leu Met Ile Ser Gly Gly Leu Glu Pro Pro Thr Phe
    50                  55                  60

Cys Val Leu Asp Arg Cys Asp Asn His Tyr Thr Thr Lys Pro Arg His
65                  70                  75                  80

Leu Pro Pro Phe Glu Val Phe Leu Phe Val Ile Phe Lys Cys Glu
                85                  90                  95

Pro Ser Ser Met Asn Tyr Gly Ala Ala Asp Glu Arg Trp Ala Asn Pro
            100                 105                 110

Pro Gln Pro Val Ala Ala Ala Glu His Gly Pro Ser Phe Asp His Ser
        115                 120                 125

Met Val Ser Glu Glu Tyr Glu His Asp Lys Lys Lys Asn Pro Ala Gln
    130                 135                 140

Lys Glu Gly Ile Ser Phe Ser Gln Ala Leu Leu Ala Ser Gly His Glu
145                 150                 155                 160

Lys Ser Asp Gly Lys Ile Lys Leu Thr Ala Arg Ser Phe Met Glu Val
                165                 170                 175

Gly Gly Tyr Ala Val Phe Leu Ile Val Leu Val Tyr Val Ala Phe Ala
            180                 185                 190

Gln Asn Ser Ile Gln Ser Tyr Tyr Ser Lys Val Met Ser Asp Leu
        195                 200                 205

Phe Val Ala Ser Thr Gly Ala Ser Gly Ala Pro Ala Phe Gly Ser Cys
    210                 215                 220

Thr Ser Met Asp Asn Ile Trp Asp Trp Leu Ser Gln Val Leu Ile Pro
225                 230                 235                 240

Gly Ile Tyr Trp Thr Glu Thr Ser Asn Ser Thr Asp Asn Glu Asn Met
                245                 250                 255

Ile Tyr Tyr Glu Asn Arg Leu Leu Gly Glu Pro Arg Ile Arg Met Leu
            260                 265                 270

Lys Val Thr Asn Asp Ser Cys Thr Val Met Lys Ser Phe Gln Arg Glu
        275                 280                 285

Ile Lys Glu Cys Phe Ala Asn Tyr Glu Glu Lys Leu Glu Asp Lys Thr
    290                 295                 300

Met Val Gly Asp Gly Ser Val Asp Ala Phe Ile Tyr Ala Thr Ala Lys
305                 310                 315                 320
```

```
Glu Leu Glu Asn Leu Lys Thr Val Gly Thr Ile Ala Ser Tyr Gly Gly
                325                 330                 335
Gly Gly Phe Val Gln Arg Leu Pro Val Ala Gly Ser Thr Glu Ala Gln
            340                 345                 350
Ser Ala Ile Ala Thr Leu Lys Ala Asn Arg Trp Ile Asp Arg Gly Ser
        355                 360                 365
Arg Ala Ile Ile Val Asp Phe Ala Leu Tyr Asn Ala Asn Ile Asn Leu
    370                 375                 380
Phe Cys Val Val Lys Leu Leu Phe Glu Leu Pro Ala Ser Gly Gly Val
385                 390                 395                 400
Ile Thr Thr Pro Lys Leu Met Thr Tyr Asp Leu Leu Thr Tyr Gln Thr
                405                 410                 415
Ser Gly Gly Thr Arg Met Met Ile Phe Glu Gly Ile Phe Cys Gly Phe
            420                 425                 430
Ile Leu Tyr Phe Ile Phe Glu Glu Leu Phe Ala Ile Gly Arg His Arg
        435                 440                 445
Leu His Tyr Leu Thr Gln Phe Trp Asn Leu Val Asp Val Val Leu Leu
    450                 455                 460
Gly Phe Ser Val Ala Thr Ile Ile Leu Ser Val Asn Arg Thr Lys Thr
465                 470                 475                 480
Gly Val Asn Arg Val Asn Ser Val Ile Glu Asn Gly Leu Thr Asn Ala
                485                 490                 495
Pro Phe Asp Asp Val Thr Ser Ser Glu Asn Ser Tyr Leu Asn Ile Lys
            500                 505                 510
Ala Cys Val Val Phe Val Ala Trp Val Lys Val Phe Lys Phe Ile Ser
        515                 520                 525
Val Asn Lys Thr Met Ser Gln Leu Ser Ser Thr Leu Thr Arg Ser Ala
    530                 535                 540
Lys Asp Ile Gly Gly Phe Ala Val Met Phe Ala Val Phe Phe Phe Ala
545                 550                 555                 560
Phe Ala Gln Phe Gly Tyr Leu Cys Phe Gly Thr Gln Ile Ala Asp Tyr
                565                 570                 575
Ser Asn Leu Tyr Asn Ser Ala Phe Ala Leu Leu Arg Leu Ile Leu Gly
            580                 585                 590
Asp Phe Asn Phe Ser Ala Leu Glu Ser Cys Asn Arg Phe Phe Gly Pro
        595                 600                 605
Ala Phe Phe Ile Ala Tyr Val Phe Val Ser Phe Ile Leu Leu Asn
    610                 615                 620
Met Phe Leu Ala Ile Ile Asn Asp Ser Tyr Val Glu Val Lys Ala Glu
625                 630                 635                 640
Leu Ala Arg Lys Lys Asp Gly Glu Gly Ile Leu Asp Trp Phe Met Asn
                645                 650                 655
Lys Val Arg Gly Leu Thr Lys Arg Gly Lys Arg Pro Asp Ala Pro Gly
            660                 665                 670
Glu Asp Ala Thr Tyr Glu Asp Tyr Lys Leu Met Leu Tyr Arg Ala Gly
        675                 680                 685
Tyr Ala Glu Lys Asp Ile Asn Glu Ala Phe Thr Arg Phe Asn Val Thr
    690                 695                 700
Ser Met Thr Glu His Val Pro Glu Lys Val Ala Glu Asp Ile Ala Asp
705                 710                 715                 720
Glu Val Ala Arg Met Thr Glu Gln Lys Arg Asn Tyr Met Glu Asn His
                725                 730                 735
Arg Asp Tyr Ala Asn Leu Asn Arg Arg Val Asp Gln Met Gln Glu Ser
```

```
                740                 745                 750
Val Phe Ser Ile Val Asp Arg Ile Glu Gly Val Asn Ala Thr Leu Gln
            755                 760                 765
Thr Ile Glu Lys Gln Arg Val Gln Gln Gln Asp Gly Gly Asn Leu Met
    770                 775                 780
Asp Leu Ser Ala Leu Leu Thr Asn Gln Val Arg Asn Arg Glu Ser Ala
785                 790                 795                 800
Ala Arg Arg Pro Thr Ile Thr Ser Ile Ala Asp Lys Lys Glu Glu
                805                 810                 815

<210> SEQ ID NO 7
<211> LENGTH: 22
<212> TYPE: DNA
<213> ORGANISM: Artificial sequence
<220> FEATURE:
<223> OTHER INFORMATION: Description of Artificial Sequence: Outside
      primer for PCR screening of lov-1 genomic (sy582) deletion

<400> SEQUENCE: 7
ctctatttgt ggttcgttgg cg                                         22

<210> SEQ ID NO 8
<211> LENGTH: 22
<212> TYPE: DNA
<213> ORGANISM: Artificial sequence
<220> FEATURE:
<223> OTHER INFORMATION: Description of Artificial Sequence: Outside
      primer for PCR screening of lov-1 genomic (sy582) deletion

<400> SEQUENCE: 8
gggagtttcc gttttcatgg gg                                         22

<210> SEQ ID NO 9
<211> LENGTH: 22
<212> TYPE: DNA
<213> ORGANISM: Artificial sequence
<220> FEATURE:
<223> OTHER INFORMATION: Description of Artificial Sequence: Nested
      primer for PCR screening of lov-1 genomic (sy582) deletion

<400> SEQUENCE: 9
ctaggaccga tgcaacagcg ag                                         22

<210> SEQ ID NO 10
<211> LENGTH: 22
<212> TYPE: DNA
<213> ORGANISM: Artificial sequence
<220> FEATURE:
<223> OTHER INFORMATION: Description of Artificial Sequence: Nested
      primer for PCR screening of lov-1 genomic (sy582) deletion

<400> SEQUENCE: 10
aacgctgatt ggttcaagtg tg                                         22

<210> SEQ ID NO 11
<211> LENGTH: 23
<212> TYPE: DNA
<213> ORGANISM: Artificial sequence
<220> FEATURE:
<223> OTHER INFORMATION: Description of Artificial Sequence: Outside
      primer for PCR screening of pkd-2 genomic (sy606) deletion

<400> SEQUENCE: 11
cccctcgttt gaccattcta tgg                                        23
```

<210> SEQ ID NO 12
<211> LENGTH: 22
<212> TYPE: DNA
<213> ORGANISM: Artificial sequence
<220> FEATURE:
<223> OTHER INFORMATION: Description of Artificial Sequence: Outside
    primer for PCR screening of pkd-2 genomic (sy606) deletion

<400> SEQUENCE: 12
acgtgatcct ctgtcgatcc ag                                           22

<210> SEQ ID NO 13
<211> LENGTH: 22
<212> TYPE: DNA
<213> ORGANISM: Artificial sequence
<220> FEATURE:
<223> OTHER INFORMATION: Description of Artificial Sequence: Nested
    primer for PCR screening of pkd-2 genomic (sy606) deletion

<400> SEQUENCE: 13
agatcaagct gactgcccgt tc                                           22

<210> SEQ ID NO 14
<211> LENGTH: 23
<212> TYPE: DNA
<213> ORGANISM: Artificial sequence
<220> FEATURE:
<223> OTHER INFORMATION: Description of Artificial Sequence: Nested
    primer for PCR screening of pkd-2 genomic (sy606) deletion

<400> SEQUENCE: 14
gatccagcga ttagccttta acg                                          23

<210> SEQ ID NO 15
<211> LENGTH: 2870
<212> TYPE: PRT
<213> ORGANISM: C. Elegans Lov-1 sy582 deletion protein

<400> SEQUENCE: 15

Met Val Leu Arg Phe Ser Pro Pro Phe Arg Phe Ser Thr Thr Ser Phe
1               5                   10                  15

Phe Ser Cys Cys Leu Phe Cys Ser Glu Phe Ile Phe Val Phe Arg Arg
            20                  25                  30

Ile Phe Thr Lys Leu Leu Gln Asp Asn Leu Pro Ala His Trp Met Lys
        35                  40                  45

Lys Ser Asn Phe Phe Val Leu Leu Leu Ala Ile Ser Ala Ile Gln
    50                  55                  60

Ile Asp Gly Leu His Tyr Gln Leu Leu Asp Gly Ile Ala Thr Phe Arg
65                  70                  75                  80

Leu Asp Asn Asp Asp Thr Thr Ile Gly Gly Val Pro Arg Asn Ser Gln
                85                  90                  95

Gly Val Val Lys Ile Lys Leu Ser Cys Gly Leu Asn Arg Leu Ser Val
            100                 105                 110

Glu Asn Lys Val Thr Glu Val Ser Ser Leu Glu Leu Ile His Asn Cys
        115                 120                 125

Ile Gln Thr Glu Thr Arg Leu Val Gly Leu Phe Leu Asn Ser Thr Trp
    130                 135                 140

Ile Thr Leu Asn Glu Val Asn Asp Asp Glu Ile Ser Ile Ala Val
145                 150                 155                 160

Glu Ala Lys Tyr Glu Val Cys Tyr Asp Asp Gly Ile Asp Arg Cys Asp
                165                 170                 175

-continued

```
Gly Ser Leu Trp Trp Leu Gln Val Gly Gly Asn Glu Met Ala Leu Leu
            180                 185                 190
Gly Tyr Arg Glu Lys Cys Glu Ser Gly Glu Ile Asn Glu Glu Tyr Ala
        195                 200                 205
Arg Arg Met Cys Lys Arg Pro Tyr Arg Ser Glu Lys Ser Thr Ala Ile
    210                 215                 220
Ser Asp Ser Gln Gly Val Tyr Tyr Asp Gly Gln Val Leu Lys Gly Val
225                 230                 235                 240
Arg Ala Lys Gln Phe Ser Met Arg Thr Ser Gly Ser Pro Thr Leu Arg
                245                 250                 255
Arg Met Lys Arg Asp Ala Gly Asp Asn Thr Cys Asp Tyr Thr Ile Glu
            260                 265                 270
Ser Thr Ser Thr Ser Thr Thr Thr Pro Thr Thr Thr Val Thr Ser
        275                 280                 285
Thr Val Thr Ser Thr Thr Thr Val Pro Thr Ser Thr Ser Thr Val Thr
    290                 295                 300
Thr Ala Met Ser Thr Ser Thr Ser Thr Pro Ser Thr Ser Thr Thr Ile
305                 310                 315                 320
Glu Ser Thr Ser Thr Thr Phe Thr Ser Thr Ala Ser Thr Ser Thr Ser
                325                 330                 335
Ser Thr Ser Thr Thr Gln Gln Ser Ser Ser Thr Ile Thr Ser Ser Pro
            340                 345                 350
Ser Ser Thr Thr Leu Ser Thr Ser Ile Pro Thr Thr Thr Thr Pro Glu
        355                 360                 365
Ile Thr Ser Thr Leu Ser Ser Leu Pro Asp Asn Ala Ile Cys Ser Tyr
    370                 375                 380
Leu Asp Glu Thr Thr Thr Ser Thr Thr Phe Thr Thr Thr Met Leu Thr
385                 390                 395                 400
Ser Thr Thr Thr Glu Glu Pro Ser Thr Ser Thr Thr Thr Thr Glu Val
                405                 410                 415
Thr Ser Thr Ser Ser Thr Val Thr Thr Thr Glu Pro Thr Thr Thr Leu
            420                 425                 430
Thr Thr Ser Thr Ala Ser Thr Ser Thr Thr Glu Pro Ser Thr Ser Thr
        435                 440                 445
Val Thr Thr Ser Pro Ser Thr Ser Pro Val Thr Ser Thr Val Thr Ser
    450                 455                 460
Ser Ser Ser Ser Ser Thr Thr Val Thr Thr Pro Thr Ser Thr Glu Ser
465                 470                 475                 480
Thr Ser Thr Ser Pro Ser Ser Thr Val Thr Thr Ser Thr Thr Ala Pro
                485                 490                 495
Ser Thr Ser Thr Thr Gly Pro Ser Ser Ser Ser Thr Pro Ser Ser
            500                 505                 510
Thr Ala Ser Ser Ser Val Ser Ser Thr Ala Ser Ser Thr Gln Ser Ser
        515                 520                 525
Thr Ser Thr Gln Gln Ser Ser Thr Thr Thr Lys Ser Glu Thr Thr Thr
    530                 535                 540
Ser Ser Asp Gly Thr Asn Pro Asp Phe Tyr Phe Val Glu Lys Ala Thr
545                 550                 555                 560
Thr Thr Phe Tyr Asp Ser Thr Ser Val Asn Leu Thr Leu Asn Ser Gly
                565                 570                 575
Leu Gly Ile Ile Gly Tyr Gln Thr Ser Ile Glu Cys Thr Ser Pro Thr
            580                 585                 590
```

```
Ser Ser Asn Tyr Val Ser Thr Thr Lys Asp Gly Ala Cys Phe Thr Lys
        595                 600                 605

Ser Val Ser Met Pro Arg Leu Gly Gly Thr Tyr Pro Ala Ser Thr Phe
        610                 615                 620

Val Gly Pro Gly Asn Tyr Thr Phe Arg Ala Thr Met Thr Thr Asp Asp
625                 630                 635                 640

Lys Lys Val Tyr Tyr Thr Tyr Ala Asn Val Tyr Ile Gln Glu Tyr Ser
                645                 650                 655

Ser Thr Thr Ile Glu Ser Glu Ser Ser Thr Ser Ala Val Ala Ser Ser
                660                 665                 670

Thr Ser Ser Thr Pro Ser Thr Pro Ser Ser Thr Leu Ser Thr Ser Thr
        675                 680                 685

Val Thr Glu Pro Ser Ser Thr Arg Ser Ser Asp Ser Thr Thr Thr Ser
        690                 695                 700

Ala Gly Ser Thr Thr Thr Leu Gln Glu Ser Thr Thr Thr Ser Glu Glu
705                 710                 715                 720

Ser Thr Thr Asp Ser Ser Thr Thr Ile Ser Asp Thr Ser Thr Thr Ser
                725                 730                 735

Thr Ser Ser Pro Ser Ser Thr Thr Ala Asp Ser Thr Ser Thr Leu Ser
        740                 745                 750

Val Asp Gln Phe Asp Phe Ile Leu Asp Ser Gly Leu Ser Trp Asn Glu
        755                 760                 765

Thr Arg His Asn Glu Asp Ser Ile Asn Ile Val Pro Leu Pro Thr Asn
        770                 775                 780

Ala Ile Thr Pro Thr Glu Arg Ser Gln Thr Phe Glu Cys Arg Asn Val
785                 790                 795                 800

Ser Thr Glu Pro Phe Leu Ile Ile Lys Glu Ser Thr Cys Leu Asn Tyr
                805                 810                 815

Ser Asn Thr Val Leu Asn Ala Thr Tyr Ser Ser Asn Ile Pro Ile Gln
                820                 825                 830

Pro Ile Glu Thr Phe Leu Val Gly Ile Gly Thr Tyr Glu Phe Arg Ile
        835                 840                 845

Asn Met Thr Asp Leu Thr Thr Met Gln Val Val Ser His Ile Phe Thr
        850                 855                 860

Leu Asn Val Val Ala Asp Ser Thr Ser Thr Ser Glu Val Thr Ser Thr
865                 870                 875                 880

Thr Ser Thr Gly Ser Ser Ser Glu Ser Ser Ala Ile Ser Thr Thr Ser
                885                 890                 895

Gly Ile Glu Ser Thr Ser Thr Leu Glu Ala Ser Thr Thr Asp Ala Ser
                900                 905                 910

Gln Asp Ser Ser Thr Ser Thr Ser Asp Ser Gly Thr Thr Ser Asp Ser
        915                 920                 925

Thr Thr Ile Asp Ser Ser Asn Ser Thr Pro Ser Thr Ser Asp Ser Ser
        930                 935                 940

Gly Leu Ser Gln Thr Pro Ser Asp Ser Ser Ser Ala Ser Asp Ser Met
945                 950                 955                 960

Arg Thr Thr Thr Val Asp Pro Asp Ala Ser Thr Glu Thr Pro Tyr Asp
                965                 970                 975

Phe Val Leu Glu Asn Leu Thr Trp Asn Glu Thr Val Tyr Tyr Ser Glu
                980                 985                 990

Asn Pro Phe Tyr Ile Thr Pro Ile Pro Asn Lys Glu Pro Gly Ala Leu
        995                 1000                1005

Thr Thr Ala Met Thr Cys Gln Cys Arg Asn Asp Ser Ser Gln Pro
```

-continued

```
                1010                1015                1020
Phe Val Leu Leu Lys Glu Ser Asn Cys Leu Thr Glu Phe Gly Lys
        1025                1030                1035
Asn Gly Ala Tyr Ser Ala Ser Val Ser Phe Asn Pro Met Thr Ser
        1040                1045                1050
Phe Val Pro Ala Thr Gly Thr Tyr Glu Phe Leu Ile Asn Val Thr
        1055                1060                1065
Asn Arg Ala Ser Gly Glu Ser Ala Ser His Ile Phe Thr Met Asn
        1070                1075                1080
Val Val Leu Pro Thr Thr Thr Thr Glu Thr Pro Pro Thr Thr Val
        1085                1090                1095
Ser Ser Ser Asp Asp Ala Gly Gly Lys Thr Gly Gly Thr Gly Ala
        1100                1105                1110
Thr Gly Gly Thr Gly Gly Thr Gly Ser Gly Gly Ser Ala Thr Thr
        1115                1120                1125
Leu Ser Thr Gly Asp Ala Val Arg Ser Thr Ser Gly Ser Gly
        1130                1135                1140
Ser Gly Gln Ser Ser Thr Gly Ser Gly Ala Gly Gly Ser Gly Thr
        1145                1150                1155
Thr Ala Ser Gly Ser Gly Ser Gly Gly Ser Ser Gly Thr Gly Ser
        1160                1165                1170
Asp Gly Val Asn Ser Gly Lys Thr Thr Ala Leu Asn Gly Asp Gly
        1175                1180                1185
Thr Gly Ser Gly Thr Ala Thr Thr Pro Gly Ser His Leu Gly Asp
        1190                1195                1200
Gly Gly Ser Thr Ser Gly Ser Gly Ser Asp Ser Asn Gly Ser Ser
        1205                1210                1215
Gly Val Ser Thr Lys Ser Ser Ser Gly Ser Asp Thr Ser Gly Ser
        1220                1225                1230
Ser Asp Ser Ser Gly Ala Asn Gly Ala Phe Ser Ala Thr Ala Gln
        1235                1240                1245
Pro Ser Thr Arg Thr Thr Lys Thr Arg Ser Ser Leu Ala Thr Val
        1250                1255                1260
Ser Pro Ile Ser Ala Ala Glu Gln Ala Ile Ile Asp Ala Gln Lys
        1265                1270                1275
Ala Asp Val Met Asn Gln Leu Ala Gly Ile Met Asp Gly Ser Ala
        1280                1285                1290
Ser Asn Asn Ser Leu Asn Thr Ser Ser Ser Leu Leu Asn Gln Ile
        1295                1300                1305
Ser Ser Leu Pro Ala Ala Asp Leu Val Glu Val Ala Gln Ser Leu
        1310                1315                1320
Leu Ser Asn Thr Leu Lys Ile Pro Gly Val Gly Asn Met Ser Ser
        1325                1330                1335
Val Asp Val Leu Lys Thr Leu Gln Asp Asn Ile Ala Thr Thr Asn
        1340                1345                1350
Ser Glu Leu Ala Asp Glu Met Ala Lys Val Ile Thr Lys Leu Ala
        1355                1360                1365
Asn Val Asn Met Thr Ser Ala Gln Ser Leu Asn Ser Val Leu Ser
        1370                1375                1380
Ser Leu Asp Leu Ala Leu Lys Gly Ser Thr Val Tyr Thr Leu Gly
        1385                1390                1395
Val Ser Ser Thr Lys Ser Lys Asp Gly Thr Tyr Ala Val Ile Phe
        1400                1405                1410
```

-continued

```
Gly Tyr Val Ile Ala Ser Gly Tyr Thr Leu Val Ser Pro Arg Cys
1415                1420                1425

Thr Leu Ser Ile Tyr Gly Ser Thr Ile Tyr Leu Thr Gly Asp Thr
1430                1435                1440

Arg Ala Ser Tyr Lys Gln Leu Asp Gly Asp Thr Val Thr Ala Asp
1445                1450                1455

Thr Met Leu Ala Ala Ala Ile Gly Ile Gln Gly Met Phe Ala Thr
1460                1465                1470

Asn Gly Arg Thr Val Gln Val Glu Gln Asp Lys Ile Asp Asp Lys
1475                1480                1485

Arg Ser Leu Val Ser Gly Asn Ile Met Ala Thr Met Ser Gly Val
1490                1495                1500

Gly Asp Val Gln Ser Gly Glu Tyr Ser Tyr Asn Asp Met Tyr Val
1505                1510                1515

Thr Ala Trp Asn Val Thr Tyr Asp Asn Ser Thr Val Gly Ser Thr
1520                1525                1530

Ser Gln Lys Asn Thr Ser Phe Ser Phe Asn Ile Pro Val Ser Glu
1535                1540                1545

Val Gln Tyr Ile Leu Leu Ile Glu Ser Gly Thr Met Ile Lys Leu
1550                1555                1560

His Ser Thr Gln Asn Ile Val Ser Arg Gly Leu Val Val Thr Ala
1565                1570                1575

Ser Tyr Gly Gly Val Thr Tyr Thr Ile Thr Cys Thr Asn Gly Thr
1580                1585                1590

Gly Lys Phe Val Glu Val Asp Thr Asp Asn Ala Ile Phe Ser Tyr
1595                1600                1605

Asn Ala Asp Ser Phe Thr Val Val Ala Ser Asp Gly Ser Ser Ala
1610                1615                1620

Ser Thr Val Lys Lys Leu Ile Gln Met Pro Ile Val Ile Glu Asn
1625                1630                1635

Val Asn Leu Ala Leu Phe Asn Gln Thr Thr Ser Pro Leu Val Phe
1640                1645                1650

Ser Asn Ala Gly Ser Tyr Ser Met Arg Met Val Leu Ser Pro Gln
1655                1660                1665

Asp Ile Gly Ile Pro Ala Val Ser Ala Leu Ser Gln Thr Val Ser
1670                1675                1680

Ile Ser Thr Leu Ser Pro Thr Ala Ser Tyr Thr Lys Asp Asp Leu
1685                1690                1695

Gln Ser Leu Ile Lys Glu Gln Thr Leu Val Thr Val Ser Gly Thr
1700                1705                1710

Thr Ser Asn Ser Leu Leu Ser Ile Ala Gly Ser Leu Thr Ser Ala
1715                1720                1725

Leu Lys Ile Ala Leu Asp Asn Pro Leu Ser Ser Asp Leu Ala Ala
1730                1735                1740

Asn Leu Lys Tyr Ala Thr Asp Asn Tyr Asp Ser Leu Tyr Asn Val
1745                1750                1755

Leu Pro Ser Asp Pro Asp Asn Ile Val Tyr Val Glu Glu Met Thr
1760                1765                1770

Ser Glu Glu Trp Ala Ala Tyr Val Thr Lys Met Phe Gln Lys Asn
1775                1780                1785

Ile Ala Lys Asn Leu Ala Asn Gln Leu Ala Ser Thr Leu Asp Thr
1790                1795                1800
```

-continued

```
Leu Glu Asn Thr Leu Ala Ala Arg Ala Ile Ala Thr Gly Asn Leu
    1805                1810                1815

Pro Tyr Asp Tyr Ser Asn Ser Val Asp Gly Thr Gly Met Val Ile
    1820                1825                1830

Val Ile Asp Asp Ala Ser Asn Ile Val Gly Lys Thr Gln Asn Cys
    1835                1840                1845

Glu Glu Trp Ala Phe Lys Leu Pro Ser Pro Ala Ser Thr Leu Asn
    1850                1855                1860

Thr Ala Glu Ile Thr Asp Lys Thr Leu Ile Gln Val Gly Leu Val
    1865                1870                1875

Cys Tyr Ala Thr Asn Pro Arg Thr Tyr Val Asp Asn Phe Asp Met
    1880                1885                1890

Leu Ile Thr Ser Gly Ala Leu Glu Ala His Ile Lys Asp Glu Asn
    1895                1900                1905

Gln Ile Ile Ile Pro Ile Thr Gly Thr Thr Ala Pro Ile Tyr Val
    1910                1915                1920

Asn Gly Arg Gly Ser Glu Asp Ala Val Leu Thr Leu Met Gln
    1925                1930                1935

Gln Gly Asp Phe Ala Ser Tyr Gln Ile Leu Asp Leu His Ala Phe
    1940                1945                1950

Arg Thr Thr Asn Trp Asn Asn Ser Leu Gln Val Glu Ile Ile Ala
    1955                1960                1965

Ser Gln Asp Tyr Glu Ile Pro Asn Asn Asp Asp Thr Tyr Met Phe
    1970                1975                1980

Ser Ser Phe Gln Ser Leu Pro Gly Pro Leu Glu Ser Asn His Glu
    1985                1990                1995

Trp Ile Phe Asp Leu Asn Thr Leu Asn Lys Thr Ser Asn Tyr Phe
    2000                2005                2010

Val Thr Ala Gly Asn Leu Ile Asn Asn Thr Gly Leu Phe Phe Ile
    2015                2020                2025

Gly Ile Gly Lys Arg Asn Ser Ser Thr Asn Thr Gly Asn Ser Ser
    2030                2035                2040

Asp Ile Val Asn Tyr Gly Gln Tyr Asp Ser Met Gln Trp Ser Phe
    2045                2050                2055

Ala Arg Ser Val Pro Met Asp Tyr Gln Val Ala Ala Val Ser Lys
    2060                2065                2070

Gly Cys Tyr Phe Tyr Gln Lys Thr Ser Asp Val Phe Asn Ser Glu
    2075                2080                2085

Gly Met Tyr Pro Ser Asp Gly Gln Gly Met Gln Phe Val Asn Cys
    2090                2095                2100

Ser Thr Asp His Leu Thr Met Phe Ser Val Gly Ala Phe Asn Pro
    2105                2110                2115

Thr Ile Asp Ala Asp Phe Ser Tyr Asn Tyr Asn Val Asn Glu Ile
    2120                2125                2130

Glu Lys Asn Val Lys Val Met Ile Ala Ala Val Phe Met Leu Val
    2135                2140                2145

Val Tyr Gly Cys Leu Thr Ile Asn Ala Ile Ile Cys Gln Arg Lys
    2150                2155                2160

Asp Ala Ser Arg Gly Arg Leu Arg Phe Leu Lys Asp Asn Glu Pro
    2165                2170                2175

His Asp Gly Tyr Met Tyr Val Ile Ala Val Glu Thr Gly Tyr Arg
    2180                2185                2190

Met Phe Ala Thr Thr Asp Ser Thr Ile Cys Phe Asn Leu Ser Gly
```

-continued

|  | 2195 |  |  | 2200 |  |  |  | 2205 |  |  |  |
| --- | --- | --- | --- | --- | --- | --- | --- | --- | --- | --- | --- |

Asn Glu Gly Asp Gln Ile Phe Arg Ser Phe Arg Ser Glu Glu Asp
         2210                2215                 2220

Gly Asn Trp Glu Phe Pro Phe Ser Trp Gly Thr Thr Asp Arg Phe
         2225                2230                 2235

Val Met Thr Thr Ala Phe Pro Leu Gly Glu Leu Glu Tyr Met Arg
         2240                2245                 2250

Leu Trp Leu Asp Asp Ala Gly Leu Asp His Arg Glu Ser Trp Tyr
         2255                2260                 2265

Cys Asn Arg Ile Ile Val Lys Asp Leu Gln Thr Gln Asp Ile Tyr
         2270                2275                 2280

Tyr Phe Pro Phe Asn Asn Trp Leu Gly Thr Lys Asn Gly Asp Gly
         2285                2290                 2295

Glu Thr Glu Arg Leu Ala Arg Val Glu Tyr Lys Arg Arg Phe Leu
         2300                2305                 2310

Asp Glu Ser Met Ser Met His Met Leu Ala Gln Thr Ile Ser Trp
         2315                2320                 2325

Phe Ala Met Phe Thr Gly Gly Gly Asn Arg Leu Arg Asp Arg Val
         2330                2335                 2340

Ser Arg Gln Asp Tyr Ser Val Ser Ile Ile Phe Ser Leu Val Val
         2345                2350                 2355

Val Ser Met Ile Ser Ile Thr Ile Leu Lys Ser Asp Asn Ser Ile
         2360                2365                 2370

Ile Ser Asp Ser Lys Ser Val Ser Glu Phe Thr Phe Thr Ile Lys
         2375                2380                 2385

Asp Ile Ala Phe Gly Val Gly Phe Gly Val Leu Ile Thr Phe Leu
         2390                2395                 2400

Asn Ser Leu His Ile Leu Leu Cys Thr Lys Cys Arg Ser His Ser
         2405                2410                 2415

Glu His Tyr Tyr Tyr Lys Lys Arg Lys Arg Glu Asp Pro Glu Phe
         2420                2425                 2430

Lys Asp Asn Ser Gly Ser Trp Pro Met Phe Met Ala Gly Met Ala
         2435                2440                 2445

Arg Thr Ile Ile Val Phe Pro Val Leu Met Gly Leu Ile Tyr Ile
         2450                2455                 2460

Ser Gly Ala Gly Met Ser Leu Met Asp Asp Leu Ala Asn Ser Phe
         2465                2470                 2475

Tyr Ile Arg Phe Leu Ile Ser Leu Ile Leu Trp Ala Val Val Phe
         2480                2485                 2490

Glu Pro Ile Lys Gly Leu Ile Trp Ala Phe Leu Ile Leu Lys Thr
         2495                2500                 2505

Arg Lys Ser His Lys Ile Ile Asn Lys Leu Glu Gly Ser Asp Gly
         2510                2515                 2520

Thr Val Val Lys Tyr Tyr Glu Met Leu Tyr Ile Phe Phe Ser Val
         2525                2530                 2535

Leu Ile Phe Val Lys Glu Ile Val Phe Tyr Leu Tyr Gly Arg Tyr
         2540                2545                 2550

Lys Val Ile Thr Thr Met Lys Pro Thr Arg Asn Pro Phe Lys Ile
         2555                2560                 2565

Val Tyr Gln Leu Ala Leu Gly Asn Phe Ser Pro Trp Asn Phe Met
         2570                2575                 2580

Asp Leu Ile Val Gly Ala Leu Ala Val Ala Ser Val Leu Ala Tyr
         2585                2590                 2595

-continued

```
Thr Ile Arg Gln Arg Thr Thr Asn Arg Ala Met Glu Asp Phe Asn
    2600                2605                2610
Ala Asn Asn Gly Asn Ser Tyr Ile Asn Leu Thr Glu Gln Arg Asn
    2615                2620                2625
Trp Glu Ile Val Phe Ser Tyr Cys Leu Ala Gly Ala Val Phe Phe
    2630                2635                2640
Thr Ser Cys Lys Met Ile Arg Ile Leu Arg Phe Asn Arg Arg Ile
    2645                2650                2655
Gly Val Leu Ala Ala Thr Leu Asp Asn Ala Leu Gly Ala Ile Val
    2660                2665                2670
Ser Phe Gly Ile Ala Phe Leu Phe Phe Ser Met Thr Phe Asn Ser
    2675                2680                2685
Val Leu Tyr Ala Val Leu Gly Asn Lys Met Gly Gly Tyr Arg Ser
    2690                2695                2700
Leu Met Ala Thr Phe Gln Thr Ala Leu Ala Gly Met Leu Gly Lys
    2705                2710                2715
Leu Asp Val Thr Ser Ile Gln Pro Ile Ser Gln Phe Ala Phe Val
    2720                2725                2730
Val Ile Met Leu Tyr Met Ile Ala Gly Ser Lys Leu Val Leu Gln
    2735                2740                2745
Leu Tyr Val Thr Ile Ile Met Phe Glu Phe Glu Glu Ile Arg Asn
    2750                2755                2760
Asp Ser Glu Lys Gln Thr Asn Asp Tyr Glu Ile Ile Asp His Ile
    2765                2770                2775
Lys Tyr Lys Thr Lys Arg Arg Leu Gly Leu Leu Glu Pro Lys Asp
    2780                2785                2790
Phe Ala Pro Val Ser Ile Ala Asp Thr Gln Lys Asp Phe Arg Leu
    2795                2800                2805
Phe His Ser Ala Val Ala Lys Val Asn Leu Leu His His Arg Ala
    2810                2815                2820
Thr Arg Met Leu Gln Thr Gln Gly Gln Tyr Gln Asn Gln Thr Val
    2825                2830                2835
Ile Asn Tyr Thr Leu Ser Tyr Asp Pro Val Ser Ala Ile His Glu
    2840                2845                2850
Thr Gly Pro Lys Arg Phe Gln Lys Trp Arg Leu Asn Asp Val Glu
    2855                2860                2865
Lys Asp
    2870

<210> SEQ ID NO 16
<211> LENGTH: 200
<212> TYPE: PRT
<213> ORGANISM: C. Elegans Pkd-2 deletion mutant (sy606) protein

<400> SEQUENCE: 16

Met Glu Gly Arg Gly Glu Gly Glu Asp Leu Pro Pro Thr Ser Tyr Phe
1               5                   10                  15
Pro Phe Glu Glu Gly His Thr Leu Trp Met Lys Arg Glu Lys Ile Lys
            20                  25                  30
His Leu Gln Arg Ile Leu Gln Phe His Ser Asp Glu Ser Ile Leu Met
        35                  40                  45
Ile Asp Lys Lys Leu Met Ile Ser Gly Gly Leu Glu Pro Pro Thr Phe
    50                  55                  60
Cys Val Leu Asp Arg Cys Asp Asn His Tyr Thr Thr Lys Pro Arg His
```

-continued

```
65                  70                  75                  80

Leu Pro Pro Phe Glu Val Phe Leu Phe Val Val Ile Phe Lys Cys Glu
                85                  90                  95

Pro Ser Ser Met Asn Tyr Gly Ala Ala Asp Glu Arg Trp Ala Asn Pro
               100                 105                 110

Pro Gln Pro Val Ala Ala Glu His Gly Pro Ser Phe Asp His Ser
           115                 120                 125

Met Val Ser Glu Glu Tyr Glu His Asp Lys Lys Lys Asn Pro Ala Gln
        130                 135                 140

Lys Glu Gly Ile Ser Phe Ser Gln Ala Leu Leu Ala Ser Gly His Glu
145                 150                 155                 160

Lys Ser Asp Gly Lys Ile Lys Leu Thr Ala Arg Ser Phe Met Glu Val
               165                 170                 175

Gly Gly Tyr Ala Val Phe Leu Ile Val Leu Val Tyr Asp Ser Ser Thr
           180                 185                 190

Pro Arg Gln Lys Ser Leu Lys Thr
        195                 200
```

POLYCYSTIC KIDNEY DISEASE GENE HOMOLOGS REQUIRED FOR MALE MATING BEHAVIOR IN NEMATODES AND ASSAYS BASED THEREON

RELATED APPLICATIONS

This application is a divisional of U.S. application Ser. No. 09/479,467, filed Jan. 6, 2000, to Paul W. Sternberg and Maureen M. Barr, and entitled "POLYCYSTIC KIDNEY DISEASE GENE HOMOLOGS REQUIRED FOR MALE MATING BEHAVIOR IN NEMATODES AND ASSAYS BASED THEREON" now abandoned. Benefit of priority under 35 U.S.C. §119(e) to U.S. Provisional Application Serial No. 60/115,127, entitled "*CAENORHABDITIS ELEGANS* STRAINS PERTURBED IN POLYCYSTIN FUNCTION" to Paul W. Sternberg and Maureen M. Barr, filed Jan. 6, 1999, is also claimed herein. The subject matter of each of U.S. Provisional Application Serial No. 60/115,127 and U.S. application Ser. No. 09/479,467 is incorporated in its entirety by reference.

FIELD OF INVENTION

Systems and assays for identification of compounds that can be used to treat polycystic kidney disease (PKD) are provided. Nematode orthologs of genes involved in PKD are identified and associated with mating behaviors. In particular, nematodes, such as *Caenorhabditis elegans,* that express mutant and wild-type orthologs of human genes involved in this disease, are used to study the functions of the proteins encoded by the genes, to screen for other genes involved in the disease, to identify mutations involved in the disease, and to screen for drugs that affect PKD. Hence an animal model is provided that permits study of the etiology of polycystic kidney disease and provides a tool to identify the genes and factors involved in the disease pathway and to identify compounds that may be used to treat or alter the disease progression, lessen its severity or ameliorate symptoms.

BACKGROUND

Polycystic Kidney Diseases

Polycystic kidney diseases (PKD) are a group of disorders characterized by the presence of a large number of fluid-filled cysts throughout grossly enlarged kidneys (Gabow et al. (1993) *Diseases of the Kidney,* Schrier et al., eds.). In humans, PKDs can be inherited in autosomal dominant (ADPKD) or autosomal recessive (ARPKD) forms. ADPKD is the more common form and is the most common, dominantly-inherited kidney disease in humans, occurring at a frequency of about 1 in 800. ARPKD occurs at a frequency of about 1 in 10,000.

ADPKD is the most common single-gene disorder leading to kidney failure (see, Emmons et al. (1999) *Nature* 401:339–340). Since ADPKD is inherited as an autosomal dominant disorder, children of affected parents have a one in two chance of inheriting the disease. Although the kidney is the most severely affected organ, the disease is systemic and affects the liver, pancreas cardiovascular system and cerebro-vascular system. The major manifestation of the disorder is the progressive cystic dilation of renal tubules (Gabow (1990) *Am. J. Kidney Dis.* 16:403–413), leading to renal failure in half of affected individuals by age 50. Microdissection, histochemical and immunologic studies show that cysts in ARPKD kidneys arise from focal dilations of medullary collecting ducts (McDonald (1991) *Semin. Nephrol.* 11:632–642). Although end-stage renal failure usually supervenes in middle age (ADPKD is sometimes called adult polycystic kidney disease), children may occasionally have severe renal cystic disease.

ADPKD-associated renal cysts may enlarge to contain several liters of fluid and the kidneys usually enlarge progressively causing pain. Other abnormalities such as hematuria, renal and urinary infection, renal tumors, salt and water imbalance and hypertension frequently result from the renal defect. Cystic abnormalities in other organs, including the liver, pancreas, spleen and ovaries are commonly found in ADPKD. Massive liver enlargement can cause portal hypertension and hepatic failure. Cardiac valve abnormalities and an increased frequency of subarachnoid and other intracranial hemorrhage have also been observed in ADPKD. Progressive renal failure causes death in many ADPKD patients, and dialysis and transplantation are frequently required to maintain life in these patients.

Numerous biochemical abnormalities associated with this disease also are observed. These include defects in protein sorting, the distribution of cell membrane markers within renal epithelial cells, extracellular matrix, ion transport, epithelial cell turnover, and epithelial cell proliferation.

Three distinct loci have been shown to cause phenotypically indistinct forms of the ADPKD humans. These include polycystin-1 (PKD1) on chromosome 16, polycystin-2 (PKD2) on chromosome 4, and polycystin-3 (PKD3) (see, e.g., Reeders et al. (1985) *Nature* 317:542–544; Kimberling et al.. (1993) *Genomics* 18:467–472; Daoust et al. (1995) Genomics, 25:733–736). The ARPKD mutation is on human chromosome 6 (Zerres et al. (1994) *Nature Genet.* 7:429–432). Two proteins polycystin-1 (PKD1) and polycystin-2 (PKD2) are defective in human autosomal dominant polycystic kidney disease.

Mutations in either PKD1 or PKD2 cause almost indistinguishable clinical symptoms. Mutations in PKD1 or PKD2 account for 95% of autosomal dominant polycystic disease (Torres et al. 1998) Current Opinion in Nephrology and *Hypertension* 7:159–1691 with greater than 85–90% of disease incidence being due to mutations in PKD1.

The human PKD1 protein is an approximately 4,300 amino-acid integral-membrane glycoprotein with a large amino-terminal extracellular domain and a small, carboxy-terminal cytoplasmic tail. The human PKD1 gene (see, e.g., U.S. Pat. No. 5,891,628), including the complete nucleotide sequence of the gene's coding region (se SEQ ID No. 1) and encoded amino acid sequence, is known (see, SEQ ID No. 2). The predicted structure of the domains suggested that it is involved in cell-cell interactions or in interactions with the extracellular matrix. The PKD2 protein has similarities to PKD1, but its topology and domain structure suggest that it might act as a subunit of a cation channel. These proteins have been shown to interact directly (Mochizuki et at. (1996) *Science* 272:1339–1342, Qian (1997) *Nature Generics* 16:179–183).

Although these genes have been implicated in the disorders, their role in it etiology is not established. In addition, while studies of kidneys from ADPKD patients exhibit a number of different biochemical, structural and physiological abnormalities, the disorder's underlying causative biochemical defect is not known. Hence the molecular mechanisms leading to cyst enlargement and progressive loss of renal function in the PKDs are not understood. Presently there are no cures or effective treatments, other than palliative treatments, for these diseases. Hence there is a need to understand the underlying biochemistry and physiology of the ADPKD and to provide treatments.

Therefore, it is an object herein to provide a means to identify the underlying biochemistry and genetics of these diseases and to provide a means to identify compounds for use in treatment of these diseases.

SUMMARY

Isolated genes, cDNA and encoded proteins from nematodes that participate in a pathway leading to an observable phenotype are provided. In particular, it is shown herein, that a mutation in *C. elegans*, which gives rise to males that are defective in certain aspects of mating behavior, lies in a gene designed herein lov-1 (location of vulva), and that this gene is an ortholog of the mammalian, particularly human, PKD1 gene. A mutation in a gene designated pkd-2 herein also gives rise to these behaviors. This gene is shown to be an ortholog of the mammalian, including human, PKD2 gene.

The expression pattern of lov-1 and pkd-2 was studied, and it was found that promoter sequences of both genes cause reporter genes to be expressed in the rays and the hook sensory neurons required for "response" and vulva location, thus showing that the LOV-1 and PKD-2 proteins are involved in chemosensory or mechanosensory signal transduction in sensory neurons.

Hence genes that are components of a pathway in nematodes are provided and are shown to be linked to observable behaviors. Each of the encoded proteins, LOV-1 and PKD-2 are components in a pathway, which appears to be a signal transduction pathway, that leads to the observed phenotype. The genes from the nematode *Caenorhabditis elegans* are exemplified herein.

The pathway is shown to be homologous to the pathway in which the human polycystins, PKD1 and PKD2, participate. In particular, it is shown herein, that a mutation in nematodes, which gives rise to males that are defective in mating behavior, lies in a gene designated herein lov-1 (location of vulva). This gene, lov-1, is shown herein to be required for two male sensory behaviors, 'response' and 'location of vulva' (Lov).

A second gene, designated pkd-2, that affects this behavior in a similar manner is also identified and provided herein. The encoded proteins are also provided. The gene, cDNA, and encoded protein are also provided. In an exemplary embodiment, the *C. elegans* genome sequence was used to isolate pkd-2. This gene is a nematode ortholog of the mammalian, particularly human PKD2 gene. Strains that contain knock-out mutants of this gene also exhibit the defective mating behaviors.

In an exemplary embodiment, provided herein are the *C. elegans* genes, designated lov-1 and pkd-2. SEQ ID No. 3 sets forth the complement (i.e., the non-coding strand) of the lov-1 gene from *C. elegans*. SEQ ID No. 4 sets forth the sequence of amino acids of the protein (N-terminus to C-terminus)). SEQ ID No. 5 sets forth the complement (i.e., the non-coding strand) of the *C. elegans* pkd-2 gene from *C. elegans*. SEQ ID No. 6 sets forth the encoded sequence of amino acids.

Also provided are the mutants of the genes, lov-1, and pkd-2 and the resulting mutant encoded proteins. Nucleic acid molecules encoding mutants of these genes are also provided. For example, deletion mutants of these genes, particularly deletion mutants that substantially or completely knock-out gene product function, are provided. Thus, nucleic acid molecules containing deletions of each of these genes and deletion mutants that alter the phenotype of nematodes, such as *C. elegans*, that contain these mutant genes are also provided. Constructs, vectors, plasmids and strains containing each of the nucleic molecules are also provided. Also provided are strains defective in these genes.

Also provided are strains containing the mutant nucleic acids. Strains that manifest the defective male sensory behaviors are also provided herein. Constructs containing the genes, vectors containing the constructs, cells containing the vectors and transgenic *C. elegans* and provided. Assays that use these strains of *C. elegans* are also provided.

As noted, it is shown herein that these genes are human homologs of the human genes that encode polycystins, proteins polycystin-1 (PKD1) and polycystin-2 (PKD2), which are defective in human autosomal dominant polycystic kidney disease. Hence, the genes and nematode strains provide model systems for studying this pathway, identifying additional components of the pathway, and for use in drug screening assays to identify compounds affect the pathway and/or compounds that serve as leads for development of drugs for treatment of polycystic kidney disease.

Each gene is shown to affect two sensory behaviors in *C. elegans*. One behavior designated "Response" and refers to the response of males to hermaphrodites; and the other behavior, designated "Lov" refers to location of the vulva by the male. Strains that are defective in either or both of these genes are also provided. In particular deletion mutants are provided.

By correlating the phenotypic behaviors with wild-type or defects in these genes, nematodes, such as *C. elegans*, can be used to identify other genes involved in this pathway and also as a means for direct screening for lead candidate compounds for drugs for treatment of PKD. Identification of additional genes necessary for PKD function can provide additional diagnostic tools for PKD. Hence, provided herein are mutant strains of *C. elegans* and assays that use the strains.

Also provided herein are assays that employ the constructs, vectors, plasmids and strains containing each of the nucleic molecules. In particular, in one type of assay wild-type nematodes are mutagenized or treated with a test compound, and those that exhibit a change in behavior are identified.

In other types of assays, nematodes that are defective in LOV and/or Response are mutagenized or treated with a compound, and those that exhibit a change in behavior are identified. Test compounds or mutations responsible for the change in behavior are identified. Such compounds are candidates for treatment of PKDs.

A Among these methods are those that involve contacting a nematode that exhibits normal mating behavior with a test compound; and selecting compounds that result in altered mating behavior, wherein the altered mating behavior comprises alteration in the behavior involving location of vulva and/or response to contact with the hermaphrodite.

Also provided are methods for identifying genes involved in autosomal dominant polycystic kidney disease (ADPKD). Among these methods are those involving mutagenizing nematodes that exhibit normal mating behavior; and identifying and selecting nematodes that exhibit altered mating behavior, where the altered mating behavior is manifested as an alteration in location of vulva and/or response to contact with the hermaphrodite. The mutated gene(s) responsible for the alteration in behavior are then identified. Databases or libraries of mammalian genes can be screened to identify homologs of these genes, which can then serve as therapeutic or diagnostic targets or aid in elucidation of the disease pathology.

Methods for identifying compounds that are candidate therapeutic agents for treatment of autosomal dominant polycystic kidney disease (ADPK) are provided. Among the methods are those in which normal males are treated with a candidate compound. Compounds that result in changes in mating behaviors or changes in mating efficiencies are selected.

Methods for identifying genes involved in the disease pathway are also provided. Among the methods are those in which normal males are mutagenized. Offspring that exhibit changes in mating behaviors or changes in mating efficiencies are selected, and mutated genes are identified and shown to be part of the pathway. Mammalian, particularly human, homologs of the mutated genes are then identified. Such genes are likely to be part of the disease pathway. Such genes can serve as therapeutic targets and disease markers for diagnostics.

Other assays use nematode strains that have mutations in either or both of lov-1 or pkd-2. As described herein, suppressor and enhancer genetics can be used to assign functions to genes, to assign genes to pathways, to identify the key switches in these pathways and to provide a sensitive assay to identify new genes in a pathway and lead compounds that modulate the activity of genes and/or gene products in the pathway.

Assays that identify the role of PKD proteins in sensory function are also provided. Since lov1 and pkd-2 are expressed in CEM neurons, they have activity in other sensory functions, such as finding the mating partner at a distance. Accordingly assays using sexual chemotaxis or kinesis are provided. For example, males that are mutagenized or treated with a test compound are placed on a surface containing males and hermaphrodites and are then observed to assess whether they can choose between males and hermaphrodites. If the male is defective in this sensory function, it will not distinguish between males and hermaphrodites.

Assays that use dominant negative forms of PKD in nematodes or in other cells to identify mutations and/or compounds that inhibit PKD function are also provided. Transgenic nematodes that express a version of the LOV-1 or PKD-2 protein that inhibits the activity of LOV-1 and/or PKD-2 as assessed by manifestation of the altered LOV and/or response phenotypic behavior(s) are used in these assays. Transgenic nematodes can be produced by any method known to those of skill in the art, including, but are not limited to, injection of the nucleic acid into the embryos or cells of the animal. Transgenic nematodes that contain a dominant negative lov-1 or pkd-2 transgene are contacted with a test compound, and compounds that interfere with a remaining activity of the LOV-1 or PKD-2 protein are selected. Alternatively, these transgenic nematodes are mutagenized, and mutants that lose a remaining activity are selected, and the gene or mutation responsible for the loss or that contributes to the loss is identified.

Assays based on localization and trafficking of LOV-1 and/or PKD-2 within a cell or cells are also provided. These assays can identify regulators and factors necessary for synthesis and transport of LOV-1 and/or PKD-2 proteins and employ strains in which LOV-1 and PKD-2 are expressed linked to a detectable label, such as a fluorescent protein. These strains are used to assess the effects of compounds or mutagenesis on the trafficking patterns of LOV-1 and PKD-2 and cellular location(s) of the proteins in the animal. Identified mutations can be mapped and the genes identified. If mammalian, particularly human, homologs of these identified genes exist, such genes can serve as therapeutic or diagnostic targets and can aid in elucidation of the disease in mammals, particularly humans. Assays for identification of transcriptional regulators of expression of lov-1 and/or pkd-2 are also provided. These assays screen for loss or alteration of expression of either gene and use transgenic nematodes with a reporter gene, such as a gene encoding a FP or lacZ or other detectable product, linked to the nucleic acid encoding lov-1or pkd-2. The animal is mutagenized or treated with a test compound, and loss of expression or reduction in expression of either gene is assessed. These assays identify regulators of and factors that affect lov-1 and pkd-2 expression. Mammalian, particularly human homologs of these regulators and factors are identified. Such regulators and factors can be therapeutic or diagnostic targets, and/or can aid in developing an understanding of the development and progression of PKD in mammals.

Kits for performing the assays, particularly, the drug screening assays, are also provided. The kits include transgenic or wild-type nematodes or both that express either wild-type or a mutant or a transgenic form of lov-1 and/or pkd-2. The nematodes may be on plates, in wells or in any form suitable for the assays. Kits containing nucleic acid encoding either of the two genes or probes based upon these sequences or reporter gene constructions containing all or portions of either or both genes are also provided. The nucleic acids may be in solution, in lyophilized or other concentrated form, or may be bound to a suitable substrate. The kits can include additional reagents for performing the assays, such reagents include any for performing any of the steps of the methods. The kits include instructions for performing the assays.

Identity (%) and number of identical amino acids (in parentheses) between LOV-1 and a particular polycystin is indicated. Although LOV-1 lacks the carboxy terminal coiled-coil domain of all known polycystins, a coiled-coil is predicted in the middle of LOV-1 using the most stringent criteria for the COILS program (data not shown). Y73F8A.B+A was identified in a Blast search of unpublished sequences available through the Sanger Center and is more similar to PKD2 (30% identity, 48% similarity, 13% gaps over 752 aa) than LOV-1 (25% identity, 44% similarity, 14% gaps over 367 aa).

Figure 3A:
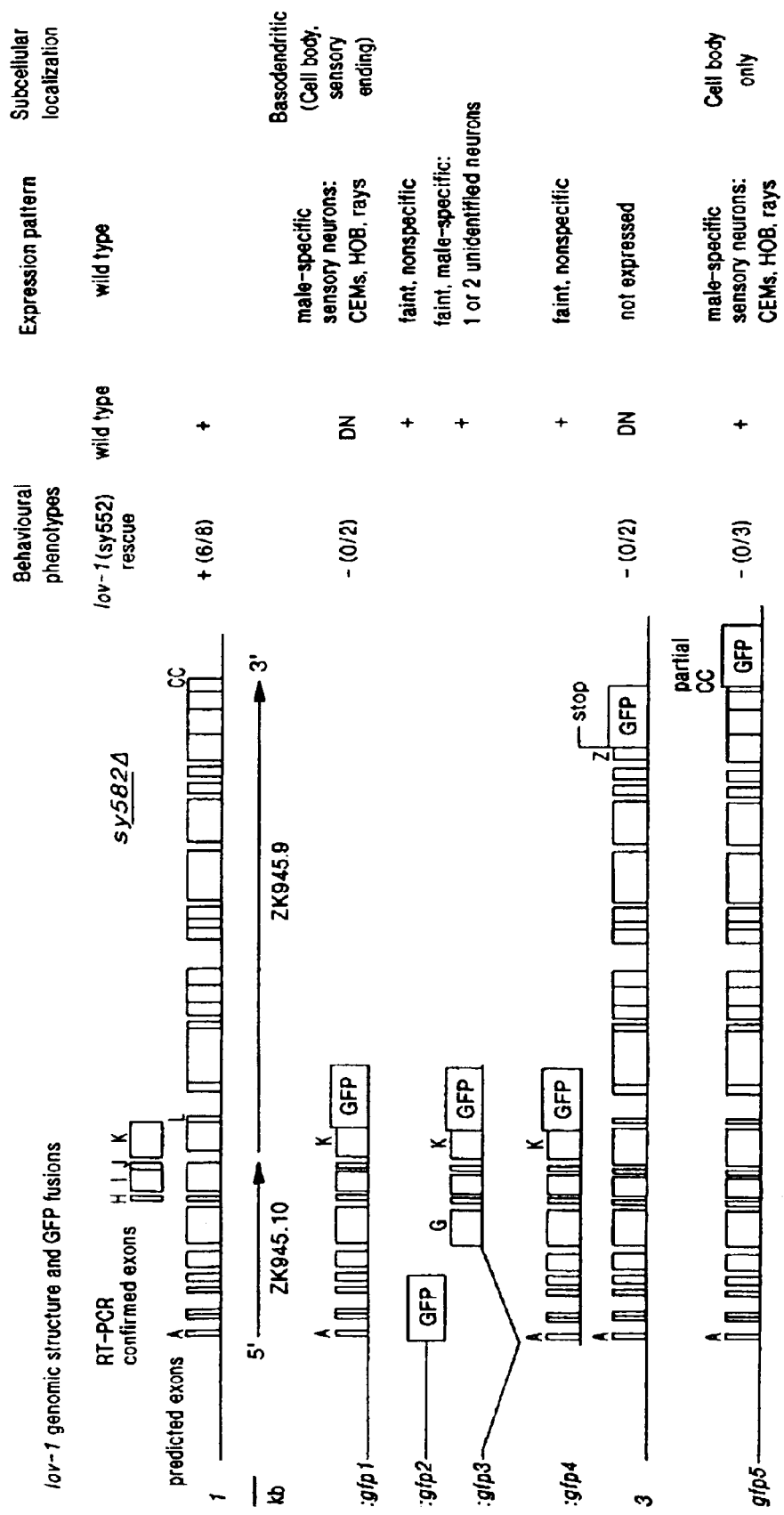

FIG. 3 shows the lov-1 and pkd-2 genomic structures, constructs, rescue date and expression patterns; the line above lov-1 indicates the 1,059 bp deletion in lov-1 (sy582Δ); numbers in parentheses indicate the ratio of rescuing stable lines to the number of stable lines examined, DN is dominant negative.

FIG. 4 shows that lov-1::GFP1 and PKD-2::GFP2 are colocalized to cell bodies and dendrites and are specifically expressed in adult male sensory neurons; the spicules, hook structure and posteriomost fan region autofluoresce; Arrows indicate neuronal cell bodies and arrowheads denote dendrites or ciliated endings. a–c lov-1::GFP1: (a) HOB and ray cell bodies (arrows), HOGB dendridic process (arrowhead); (b) HOB and ray process 5 (arrowheads); (c) Ciliated endings in nose tip from male specific cephalic CEM neurons (cell bodies not shown). d–f pkd-2::GFP2: (d) ray cell bodies (arrow) and ray process 2 (arrowhead); (e) ray process 5 (arrowhead); (f) male-specific cephalic CEM ciliated endings (arrow) Scale bar corresponds to 20 μm.

DETAILED DESCRIPTION

Definitions

Unless defined otherwise, all technical and scientific terms used herein have the same meaning as is commonly understood by one of skill in the art to which this invention belongs. *Caenorhabditis elegans* nomenclature is well understood by those of skill in this area (see, e.g., *Methods in Cell Biology C. elegans* I, and II, Academic Press, Shakes, Epstein eds. 1995).

All patents, patent applications and publications referred anywhere herein, including the background, are, unless noted otherwise, incorporated by reference in their entirety. In the event a definition in this section is not consistent with definitions elsewhere, the definition set forth in this section will control.

As used herein, nematode is intended to refer generally to the class Nematoda or Nematoidea and includes those animals of a slender cylindrical or thread-like form commonly called roundworms. Among those species, members of the genus Caenorhabditis are preferred, but species that can be cultured in the laboratory may be used.

As used herein, the term "mutant," as in "nematode mutant" or "mutant nematode," is intended to refer generally to a nematode which contains an altered genotype, preferably stably altered. The altered genotype results from a mutation not generally found in the genome of the wild-type nematode.

As used herein, a mutant gene, such as a mutant lov-1 or pkd-2 gene, refers to a gene that is altered, whereby a nematode with such gene, expresses an altered phenotype compared to a nematode with the wild type gene, such as the genes set forth in SEQ ID Nos. 3 and 5 (which set forth the non-coding strands). Mutations include point mutations, insertions, deletions, rearrangements and any other change in the gene that results in an altered phenotype. Deletion mutants that eliminate the function of the encoded protein (knock-out mutations) are exemplified herein. Not all mutations necessarily completely destroy the activity of the protein.

As used herein, "normal mating behavior" means that the animal exhibits behavior typical of wild-type nematodes with respect to the location of vulva (Lov) and response of males to hermaphrodites. Thus a male that exhibits "normal mating behavior" upon encountering a hermaphrodite, ceases forward motion, places his tail flush on the hermaphrodite, commences backing along her body, and turns at her ends until he encounters her vulva and stops. This is the behavior of a lov-1(+) male. Mutant males defective in lov-1 frequently do not respond to contact with the hermaphrodite and continue blindly moving forward. When response is initiated, lov-1 mutants back and turn normally but pass the vulva at a high frequency. Thus, they can mate with paralyzed or otherwise slow moving hermaphrodites.

As used herein, a mammalian homolog of a nematode gene refers to a gene that encodes a protein that exhibits identifiable sequence homology and conservation of structure. The degree of sequence homology between a mammalian and nematode protein or gene to be considered homologs, depends upon the gene considered but is typically at least about 30% at the protein level. An ortholog will typically have greater sequence similarity and conservation of structure and often function. Methods and criteria for identifying mammalian, including human, homologs of nematode genes are known to those of skill in the art and involve a comparison of the sequence and structural features of the encoded protein.

As used herein, a dominant negative mutation is a mutation that encodes a polypeptide that when expressed disrupts that activity of the protein encoded by the wild-type gene (see, Herskowitz (1987) *Nature* 329:219–222). The function of the wild-type gene is blocked; a cloned gene is altered so that it encodes a mutant product that inhibits the wild-type gene product in a cell or organism. As a result, the cell or organism is deficient in the product. The mutation is "dominant" because its phenotype is manifested in the presence of the wild-type gene, and it is "negative" in the sense that it inactivates the wild-type gene function. It is possible to do this because proteins have multiple functional sites.

As used herein, a "library" of nematodes is a collection of a plurality of nematodes, typically more than 10, preferably more than 100. Typically a library will include variety of different nematodes and may include wild-type and mutant nematodes and a sufficient number to achieve the intended purpose for which the library is used.

As used herein, a gene encoding LOV-1 protein refers to a gene (a sequence of nucleotides including introns, and exons, and optionally transcriptional regulatory sequences) from any nematode that encodes a protein that performs the same function in the nematode as the LOV-1 protein provided herein. Such protein can be identified using the methods provided herein for identifying it in *C. elegans,* or by isolating cDNA encoding the protein using probes constructed from the nucleic acid provided herein to isolate it using standard methods. Typically the coding sequence of the gene provided herein will hybridize along its length to the coding sequence of a related gene under conditions of at least low stringency, preferably moderate stringency, and likely under conditions of high stringency. Nucleic acid encoding a LOV-1 protein includes any nucleic acid molecule, DNA, cDNA, RNA, that encodes a protein that has substantially the sequence of amino acids set forth in SEQ ID No. 4 and encodes a protein that has the same activity as this protein. Minor sequence variations from species to species and even among a species are considered to be substantially the same sequence. Such nucleic acid will hybridize to the nucleic acid encoding the proteins provided herein under conditions of at least low stringency, preferably moderate stringency and more preferably high stringency.

As used herein, a gene encoding PKD-2 protein from a nematode is similarly defined, except that it has the substantially the same sequence as the sequence of amino acids set forth in SEQ ID No. 6. Having identified these proteins and functions therefor in *C. elegans* permits similar identification in other nematode species.

As used herein, stringency conditions refer to the washing conditions for removing the non-specific probes and conditions that are equivalent to either high, medium, or low stringency as described below:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

As used herein, percentage or amount or degree of sequence identity is used interchangeable with homology and refers to sequence identity or homology determined using standard alignment programs with gap penalties and other parameters set to the manufacturer's default settings. It is understood that for relatively high levels of sequence identity or homology, the particular program selected and/or defaults set for various parameters, do not substantially affect the results. Hence, for example, a requirement for 90% sequence identity of a nucleic acid sequence with another can be determined using any program known to the skilled artisan or manually, and that such percentage can encompass about 85% to 95% identity.

As used herein, reference to a drug refers to a chemical entity, whether in the solid, liquid, or gaseous phase that is capable of providing a desired therapeutic effect when administered to a subject. The term "drug" should be read to include synthetic compounds, natural products and macromolecular entities such as polypeptides, polynucleotides, or lipids and also small molecules, including, but are not limited to, neurotransmitters, ligands, hormones and elemental compounds. The term "drug" is meant to refer to that compound whether it is in a crude mixture or purified and isolated.

As used herein, heterologous or foreign DNA and RNA are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Examples of heterologous DNA include, but are not limited to, DNA that encodes exogenous invertase. Heterologous DNA and RNA may also encode RNA or proteins that mediate or alter expression of endogenous DNA by affecting transcription, translation, or other regulatable biochemical processes.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, a gene containing a heterologous transcriptional or translational or processing control region(s) refers to a nucleic acid molecule or construct that includes coding portion of a gene operatively linked to a such region derived from a different gene. A homologous transcriptional or translational or processing control region(s) refers to a nucleic acid molecule or construct that includes coding portion of a gene operatively linked to a such region derived from the same gene.

As used herein, a promoter region refers to the portion of DNA of a gene that controls expression of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. A constitutive promoter is always turned on. A regulatable promoter requires specific signals to be turned on or off, A developmentally regulated promoter is one that is turned on or off as a function of development.

As used herein, regulatory sequences include, sequences of nucleotides that function, for example, as transcriptional and translational control sequences. Transcriptional control sequences include the promoter and other regulatory regions, such as enhancer sequences, that modulate the activity of the promoter, or control sequences that modulate the activity or efficiency of the RNA polymerase that recognizes the promoter, or control sequences that are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, transcriptional controls sequences include sequences of nucleotides that alter translation of the resulting mRNA, thereby altering the amount of a gene product.

As used herein, a reporter gene refers to a gene that encodes a detectable product. Such genes are well known to those of skill in the art and include, but are not limited to, genes encoding fluorescent proteins, particularly the well-known green fluorescent proteins, lacZ, enzymes and other such reporters known to be expressible and detectable in nematodes. These genes are linked to a gene of interest whereby upon expression of a detectable fusion protein is produced. For purposes herein, such fusions are exemplified using an aequorin GFP (see, Chalfie et al. (1994) *Science* 263:802–805; see, also U.S. Pat. No. 5,741,668), but any such protein may be used. For example, GFP from Aequorea Victoria contains 238 amino acids, absorbs blue light and emits green light; it has been cloned and its sequence characterized; and various mutants are also well known. Nematode optimized codons may be selected.

As used herein, a reporter gene construct is a nucleic acid molecule that includes a reporter gene operatively linked to transcriptional control sequences. Typically the construct will also include all or a portion of a the gene of interest, which herein is lov-1 and/or pkd-2, and the reporter gene will be under the control of the lov-1 or pkd-2 promoter and other regulatory regions. By operatively linked is meant linked whereby an in-frame fusion protein is produced upon expression of the construct and whereby the reporter gene product is active (i.e. produces a detectable signal or is active). The reporter gene may be linked to the 3' or 5' end or in any other orientation whereby it is expressed and operates as a reporter.

As used herein, isolated, substantially pure DNA refers to DNA molecules or fragments purified according to standard techniques employed by those skilled in the art, such as those described in Sambrook et al. (1989) *Molecular Cloning: A Laboratory Manual,* Cold Spring Harbor Laboratory Press, Cold Spring Harbor, N.Y.).

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, cloning vehicle or vector, which are used interchangeably, refers to a plasmid or phage DNA or other DNA molecules that replicate autonomously in a host cell, and that include one or a small number of endonuclease recognition sites at which such DNA may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, include but are not limited to, tetracycline resistance and ampicillin resistance.

Appropriate expression vectors are well known to those of skill in the art and include those that are replicable in eukaryotic cells and/or prokaryotic cells. Such expression vectors may remain episomal or may integrate into the host cell genome. Expression vectors suitable for introducing heterologous DNA into plants and into host cells in culture, such as mammalian cells and methylotrophic yeast host cells, are known to those of skill in the art. It should be noted that, because the functions of plasmids, vectors and expression vectors overlap, those of skill in the art use these terms, plasmid, vector, and expression vector, interchangeably. Those of skill in the art, however, recognize what is intended from the purpose for which the vector, plasmid or expression vector is used.

As used herein, integrated into the genome means integrated into a chromosome or chromosomes.

As used herein, a "fragment" of a protein refers to any portion of a protein that contains less than the complete amino acid sequence of the protein but that retains a biological or chemical function of interest.

As used herein, expression vector or expression vehicle refers to such vehicle or vector that is capable, after transformation into a host, of expressing a gene cloned therein. The cloned gene is usually placed under the control of (i.e., operably linked to) certain control sequences such as promoter sequences. Expression control sequences will vary depending on whether the vector is designed to express the operably linked gene in a procaryotic or eukaryotic host and may additionally contain transcriptional elements such as enhancer elements, termination sequences, tissue-specificity elements, and/or translational initiation and termination sites.

As used herein, a variant of a protein refers to a protein substantially similar in structure and biological activity to either the entire protein or a fragment thereof. Thus, provided that two proteins possess a similar activity, they are considered variants as that term is used herein even if the composition or secondary, tertiary, or quaternary structure of one of the molecules is not identical to that found in the other, or if the sequence of amino acid residues is not identical.

It is also understood that any of the proteins or portions disclosed herein may be modified by making conservative amino acid substitutions and the resulting modified subunits are contemplated herein. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, eq., Watson et al. *Molecular Biology of the Gene,* 4th Edition, 1987, The Benjamin/Cummings Pub. Co., p.224). Such substitutions are preferably, although not exclusively, made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Comparable mutations may be made at the nucleotide sequence level.

Other substitutions are also permissible and may be determined empirically or in accord with known conservative substitutions. Any such modification of the polypeptide may be effected by any means known to those of skill in this art. Mutation may be effected by any method known to those of skill in the art, such as by chemicals or radiation, and also including site-specific or site-directed mutagenesis of DNA encoding the protein and the use of DNA amplification methods using primers to introduce and amplify alterations in the DNA template.

As understood by those skilled in the art, assay methods for identifying compounds, such as antagonists and agonists, that modulate functioning of a protein or protein or pathway, generally require comparison to a control. One type of a "control" system is one that is treated substantially the same as the system, such as a worm, exposed to the test compound except that the control is not exposed to the test compound. Another type of a control may be one that is identical to the test system, except that it does not express the gene or protein of interest. In this situation, the response of a test system is compared to the response (or lack of response) of the control to the test compound, when each cell is exposed to substantially the same reaction conditions in the presence of the compound being assayed.

As used herein, treatment means any manner in which the symptoms of a condition, disorder or disease are ameliorated or otherwise beneficially altered.

As used herein, amelioration of the symptoms of a particular disorder by administration of a particular pharmaceutical composition refers to any lessening, whether permanent or temporary, lasting or transient that can be attributed to or associated with administration of the composition.

As used herein, a composition refers to any mixture of two or more components. It may be solution, suspension, or any other mixture.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

Nematodes as Disease Models

Nematodes serve as model organisms for the study of gene expression. *Caenorhabditis elegans* is representative of nematodes. It is a small, freeliving bacteriovorous soil nematode that is a member of the Rhabditidae, a large and diverse group of nematodes found in terrestrial habitats. Some rhabditids are pathogenic to or parasitic on animals. In common with other nematodes, *C. elegans* develops through four larval stages (also called juveniles) that are separated by moults. The lifecycle takes about 3 days at 20° C.

*C. elegans* is only 1 mm long and can be handled in a manner similar to microorganisms, including growth on petri plates seeded with bacteria. In the laboratory, *C. elegans* is fed on *E. coli*. It has a transparent body and all somatic cells (959 female; 1031 male) are visible with a microscope.

Although it is a primitive organism, it shares many of the essential biological characteristics, including embryogenesis, morphogenesis, development and aging that are central problems of human biology. The worm is conceived as a single cell that undergoes a complex process of development, starting with embryonic cleavage, proceeding through morphogenesis and growth to the adult. It has a nervous system with a 'brain' (the circumpharyngeal nerve ring), It exhibits definable behaviors and is capable of rudimentary learning. It produces sperm and eggs, mates and reproduces. After reproduction it gradually ages, loses vigor and dies. Its average life span is 2–3 weeks.

Adult *C. elegans* are usually self-fertilizing protandrous hermaphrodites. As a result homozygous mutant stocks can be readily generated. The hermaphrodite gonad first produces germ cells that differentiate as sperm (about 250 sperm are produced) and then produces eggs. The fecundity is determined by the sperm supply.

Nematodes, particularly *C. elegans,* is one of the most thoroughly understood of all multicellular organisms. The biology of its nervous system, which contains 302 neurons, is well-documented. Many *C. elegans* genes used have counterparts in mammals, including humans. At least half of the *C. elegans* genes and proteins that have been characterized have structures and functions similar to mammalian genes. These include genes that encode enzymes, proteins necessary for cell structure, cell surface receptors and genetic regulatory molecules.

Animals from man to worm have most of their protein families in common, and humans frequently have four to five close analogs of a protein family member, where worms have only one. Essentially all genes and pathways shown to be important in cell-, developmental- and disease-biology have been found to be conserved between worm and human. This conservation applies to the number and type of protein families, gene structure, the hierarchy of genes in genetic pathways and even gene regulation.

A consequence of this conservation is that human genes can be inserted into the worm genome, to functionally replace the worm genes even in complex cell biological and signal transduction pathways. Conversely, key worm genes identified using genetics can be used to trigger specific biochemical processes in human cells and to serve as models for the human genes.

Genetics Nomenclature

*C. elegans* is diploid and has five pairs of autosomal chromosomes (designated I, II, III, IV and V) and a pair of sex chromosomes (X) that determine gender. XX is a hermaphrodite and XO is male. Males are found rarely (about 0.05% of normal lab populations). The commonest lab strain, and the designated "wild-type" strain, is called N2.

For historical reasons *C. elegans* nomenclature is different from other species. Loci have a 3-letter dash one number designation. The letters are an acronym for the phenotype, and the number is consecutive. Alleles have a single or double letter followed by a number. The letter identifies the isolating laboratory. Strains have a letter(s) number designation. The letters identify the isolating laboratory (i.e. AB100 abc-1 (xy1000) Strain AB100 which carries the xy1000 allele of abc-1 . The chromosomal location can be added: AB100 abc-1(xy1000) I. Multiple mutant alleles carried in one strain are organized by chromosome, and chromosomes separated by semicolons. Heterozygous nematodes are designated by a abc-1/+notation. Hence abc-1(+) indicates the wild-type (N2 strain) copy of the gene. Proteins are capitalized and not italicized. ABC is the protein product of abc-1.

Rearrangements, duplications and deficiencies have a letter prefix (indicating the isolating lab) a Dp (pronounced dupe, for duplication) or Df (pronounced dif for deficiency) and a number (i.e., xyDp1 is duplication number 1 from xy and xyDf1 is deficiency number 1 from xy lab). Transgenic strains carrying the transgene as a free extrachromosomal array are designated as follows: xyEx1[abc-1(+)] is a transgenic strain carrying the wt copy of abc-1.

The *C. elegans* Genome

The *C. elegans* genome, which is 97 Mb, contains six approximately equally sized chromosomes (5 autosomes, one X) and it has been sequenced (see,(1998) *Science* 282:2012–2018) and is publicly available. The 97 Mb encodes a predicted 19,099 protein-encoding genes; although as shown herein, there remain ambiguities. Over 60,000 cDNA fragments have been tag sequenced and 101000 ESTs deposited. These "expressed sequence tags" or ESTs offer a set of snapshots of gene expression in the nematode, and have identified around half of the organism's genes. The cDNA data are used in the prediction of genes from the genome sequence along with database searches for similarities between *C. elegans* genes and those of other organisms such as humans. This estimate is based on the correspondence between genomic DNA sequence and cDNA sequences, and on the prediction of coding genes from genomic sequence. The genome data (and much else besides) is collated into an available database ACeDB, written for the *C. elegans* project. A physical map of the genome, which is publicly available in the *C. elegans* genome database ACeDB, has been constructed. The map is based on 17,000 cosmid clones of genomic DNA (insert size 35–40 kb). These clones were "fingerprinted" using restriction enzymes, and the fingerprints used to order the clones in overlapping contiguous sets, or contigs. These cosmid contigs have been supplemented by a set of 3,000 yeast artificial chromosome clones (insert sizes 100 kb and above). Because the yeast host tolerates sequences that E. coli does not, the YAC clones can "bridge" gaps between contigs of cosmids. With these two resources, contigs covering >95% of all the chromosomes have been assembled. The clones are freely available for researchers, and the 3,000 YAC clones are available as an array on a filtermat, arranged in approximate chromosomal order, for screening purposes.

The genomes of other nematodes are in the same size range. Brugia malayi, a filarial parasite of humans, has a genome of 100 Mb; Ascaris suum, the pig roundworm, has a larger germ line genome which undergoes somatic diminution.

Identification of the Genes Associated with the Location of Vulva and Response Behaviors The Behaviors The six sub-steps of the stereotyped copulatory sequence has been correlated with the function of individual neurons, and behavioral mutants have been isolated (Liu et al. Neuron 14:79–89). C. elegans male mating behavior includes a series of steps: response to contact with the hermaphrodite, backing along the body of the hermaphrodite, turning around her head or tail, location of the vulva, insertion of the two copulatory spicules into the vulva and sperm transfer. Sensory structures and neurons that participate in each of these steps have been identified: the sensory rays mediate response to contact and turning; the hook, the postcloacal sensilla and the spicules mediate vulva location; and the spicules also mediate spicule insertion and regulate sperm transfer.

Figure 1:
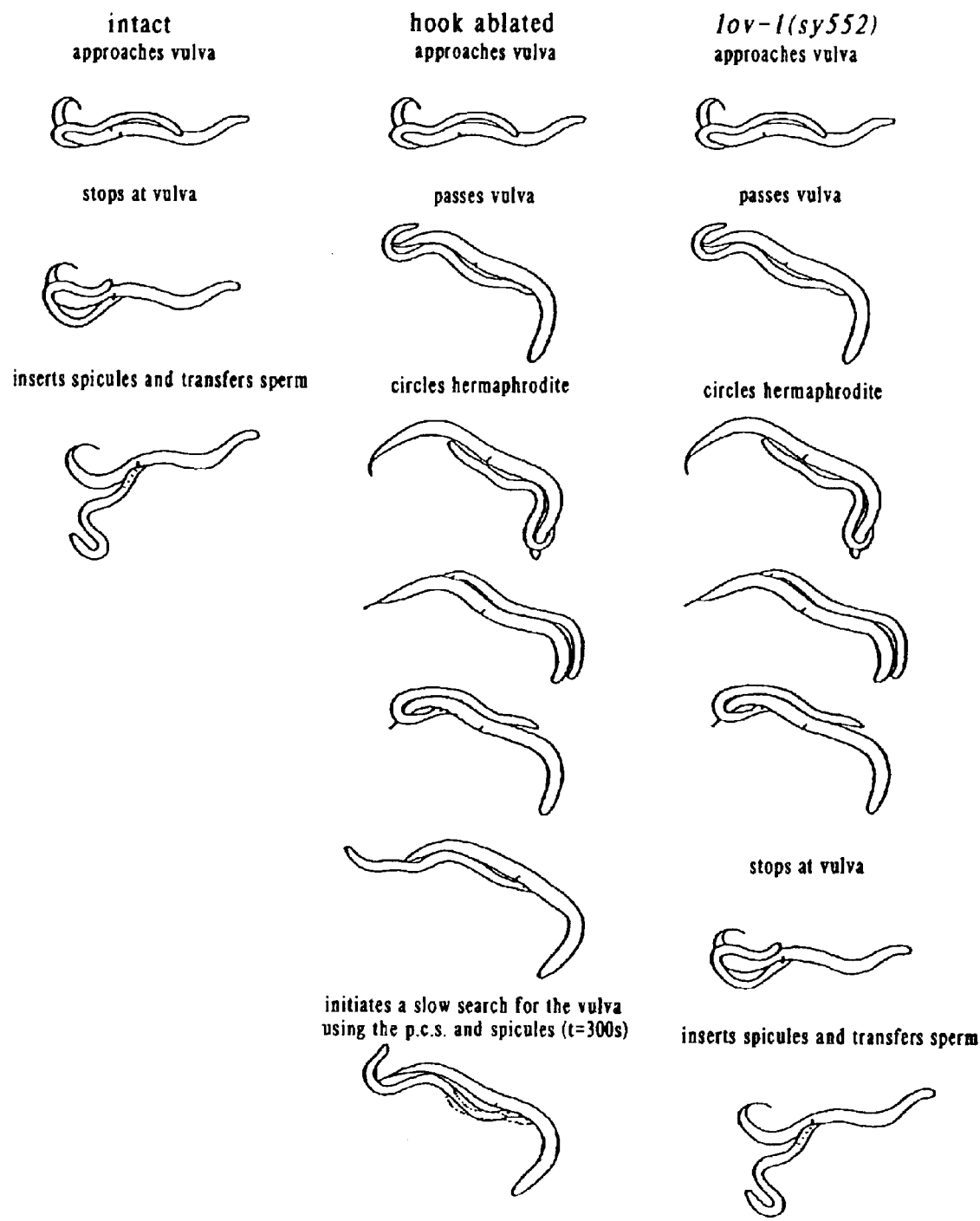
FIG. 1 depicts male mating behavior of *C. elegans*. The hermaphrodite is larger than the male, and her vulva is depicted as a slit on the ventral, posterior third of her body. The male tail is place flush on the hermaphrodite, ventral side down. His spicules are depicted by a line in the tail. The hook is anterior to the spicules; the post cloacal sensilla is posterior. Sequence 1 illustrates wild-type male Lov. Sequence 2 represents hook ablated aberrant Lov behavior (passing and slow search). Sequence 3 portrays lov-1(sy552) mutant behavior (passing and eventually stopping).

Thus, the stereotyped mating behavior of the Caenorhabditis elegans male comprises several substeps: response backing, turning, vulva location, spicule insertion, and sperm transfer (FIG. 1). The complexity of male mating behavior is reflected in the sexually dimorphic anatomy and nervous systems of the male and hermaphrodite (Hodgkin, J. (1988) in The Nematode C. elegans (ed. Wood, B.) pp. 243–279 (Cold Spring Harbor Laboratory Press, New York). Behavioral functions have been assigned to most male-specific sensory neurons via cell ablations (Liu et al. Neuron 14:79–89). Although the hermaphrodite is behaviorally passive, her vulva provides sensory cues to the male.

Vulva location behavior is complex. The male stops and precisely positions his tail over the vulva, coordinates his movement to the hermaphrodite's, and ultimately insert his spicules into the vulva slit and transfers sperm into the uterus. The hook sensory neurons, HOA and HOB, are specifically required for location of vulva (Lov) behavior. Ablation of either HOA or HOB results in a Lov defect whereby the ablated male circles the hermaphrodite without stopping at the vulva (FIG. 1). Eventually, the ablated male begins an alternative search by backing slowly and prodding randomly with his spicules until the vulva is located. The postcloacal sensilla are required for slow search behavior. Vulva location behavior is executed by a minimum of eight sensory neurons with overlapping and redundant functions (Liu et al. Neuron 14:79–89).

A genetic analysis of vulva location behavior to investigate how genes specify sensory behavior, beginning with sensory reception, was performed. The mating behavior of existing mutants defective in sensory behaviors including chemotaxis to soluble and volatile odorants, mechanosensation, and osmotic avoidance was first examined. From this survey, it was found that only males with severe defects in all sensory neuron cilia (osm-4, osm-5, osm-6, and che-3) were Lov defective (Table 2). For example, osm-6(p811) males locate the vulva with an efficiency of 32% versus 96% of wild-type (Table 2). These males are also response defective, but not so severely as to prevent observation of the Lov phenotype. The only ciliated cells in C. elegans are chemosensory and mechanosensory neurons (White et al. (1986) Philos. Trans. R. Soc. Lond. B Biol. Sci. 314:1–67). The male tail possesses thirty predicted ciliated sensory neurons (Sulston et al. 1980) Dev. Biol 78:542–576), consistent with the observation that ciliated neurons modulate response and Lov. osm-6::gfp is expressed exclusively in ciliated neurons, with male-specific expression in four CEM head neurons and neurons of the rays and copulatory spicules (Collet et al. (1998) Genetics 148:187–200). More detailed examination revealed that osm-6::gfp expression begins at the L4 stage in neuronal cell bodies and extends to dendrites as neuronal outgrowth proceeds (data not shown). The RnA and RnB neurons of each ray (ray 1 through ray 9), the HOA and HOB hook neurons, the spicule neurons SPV and SPD, and the PCB postcloacal sensilla neurons accumulate GFP. The osm-6 expression pattern and mutant phenotypes indicate that OSM-6 might be required for the structure and function of ciliated neurons in the adult male tail. In the hermaphrodite, osm-6 function is required for nose touch (Kaplan et al. (1993) Proc. Natl. Acad. Sci. U.S.A. 90:2227–2231), osmotic avoidance, chemotaxis, dye-filling of sensory neurons, thermotaxis, dauer formation, and proper assembly of ciliated sensory endings (Perkins et al. (1986) Dev. Biol. 117:456–487). Hence, ciliated endings are important for all known sensory behaviors, including Lov.

TABLE 2

Vulva location behavior of wild-type and mutant males

| Genotype | vulva location efficiency % | Significantly different from wild-type (p value) | †n |
|---|---|---|---|
| him-5 (wild-type) | 96 | — | — | 101 |
| osm-1(e1803) | 65 | No | (0.0738) | |
| osm-4(p821) | 48 | Yes | (0.0004) | |
| osm-5(p813); him-5 | 26 | Yes | (0.0002) | |
| osm-6(p811) | 32 | Yes | (0.0003) | |
| che-3(e1124) | 69 | Yes | (0.02666) | |
| lov-1(sy582Δ) | 11 | Yes | (<0.0001) | |
| lov-1(sy582); him-5 | 30 | Yes | (<0.0001) | |

Table 2. lov-1(sy522); him-5(e1490), lov-1(sy582Δ), and all cilia defective mutant were also response defective. Males that eventually responded were scored for Lov behavior.
†n represents the number of males observed; each for a minimum of 10 vulva encounters per male. Mann-Whitney tests determined p vales. The following non-cilia-defective osmotic avoidance (osm), mechanosensory defective (mec), chemosensory defective (che), odorant response abnormal (odr) and dauer formation defective (daf) mutants were also examined and found to be normal for response and Lov behavior: osm-3(e1806); him-5 (e1490), osm-7(n1515), osm-8(n1518), osm-10(n1604),osm-11(n1604), osm-12(n1606), mec-3(e1338) him-8(e1489), mec-4(e 1611), mec-5 (e1340), mec-7(n434), mec-7(e1343), mec-8(e398), mec-9(e1494), che-112, odr-1(n1936), odr-2(n2145), odr-3(n2150), odr-4(n2144ts), odr-5, odr-6(kyl), odr-7(ky4, odr-10(ky32) and daf-11 (m47ts).

Provided herein are mutants that are defective in location of the vulva (Lov). Lov mutant males are unable to execute this step. In addition, these males are also defective in the first sub-step, 'response'. Response and vulva location depend on two types of male sensory structure: the first is a set of nine pairs of rays, which project out of the tail on each side; and the second is a hardened cuticular structure called the hook, which contains two sensory neurons. These mutants were used to identify the genes involved in these behaviors.

Identification and Cloning of the Lov-1 Gene

To elucidate the molecular basis of behavior and sensory the mutants are studied and genes associated with the behaviors are identified. A gene designated lov-1 that is required for two male sensory behaviors, response and location of vulva (Lov), is described herein. It is also associated with other sensory behaviors controlled by the CEM neurons.

This gene, lov-7, encodes a putative membrane protein with a mucin-like, serine-threonine rich amino terminus (Carraway et al. (1995) *Trends Glycoscience Glycotechnology* 7:31–44) followed by two blocks of homology to human polycystins encoded by the autosomal dominant polycystic kidney disease (ADPKD) genes (Torres et al. (1998) *Current Opinion in Nephrology and Hypertension* 7:159–169). LOV-1 and human PKD1 are 26% identical in block 1. Block 2 also shows 20% identity between LOV-1, all identified polycystins (PKD1, PKD2, and PKDL), and the family of voltage-activated channels (Torres et al. (1998) *Current Opinion in Nephrology and Hypertension* 7:159–169). Overall, LOV-1 is the closest *C. elegans* homolog of PKD1. The polycystin/channel domain (block 2) of LOV-1 is required for function. Lov-1 is specially expressed in adult male sensory neurons of the rays, hook, and head, mediating response, Lov, and potentially chemotaxis to hermaphrodites, respectively (Liu et al. *Neuron* 74:79–89, Ward et al. (1975) *J. Comp. Neurol.* 160:313–337). Localization of lov-1 to neuronal cell bodies and ciliated sensory endings is consistent with a role in either chemo- and/or mechanosensory reception and signaling. Human PKD proteins might similarly be involved in sensory reception during osmoregulation, organogenesis and/or organ maintenance.

Cloned Genes and Encoded Proteins

To identify genes specifically required for male sensory behaviors, mutants defective in Lov were screened. Lov-1 (sy552) males have specific response and Lov defects. Upon encountering a hermaphrodite, a lov-1(+) male ceases forward motion, places his tail flush on the hermaphrodite, commences backing along her body, and turns at her ends until he encounters her vulva and stops. Mutant males defective in lov-1 frequently do not respond to contact with the hermaphrodite and continue blindly moving forward. When response is initiated, lov-1 mutants back and turn normally but pass the vulva at a high frequency. The response and vulva location ability of lov-1(sy552) is 30% that of lov-1(+) males (Table 2). Spicule insertion and sperm transfer behaviors are unaffected. lov-1(sy552) males exhibit high mating efficiency with severely paralyzed unc-52 hermaphrodites but sire few progeny with actively moving dpy-17 hermaphrodites. Differences between mating efficiencies is partner-dependent. A paralyzed partner is an easier target for the lov-1 mutant male who is defective in response and Lov but unimpaired in the behaviors of backing, turning, spicule insertion, and sperm transfer. The behavioral defects of sy552 are limited to male mating. Lov-1(sy552) mutants appear normal for other sensory behaviors including egg laying, nose touch, tap, mechanosensation, and osmotic avoidance.

Figure 2A:
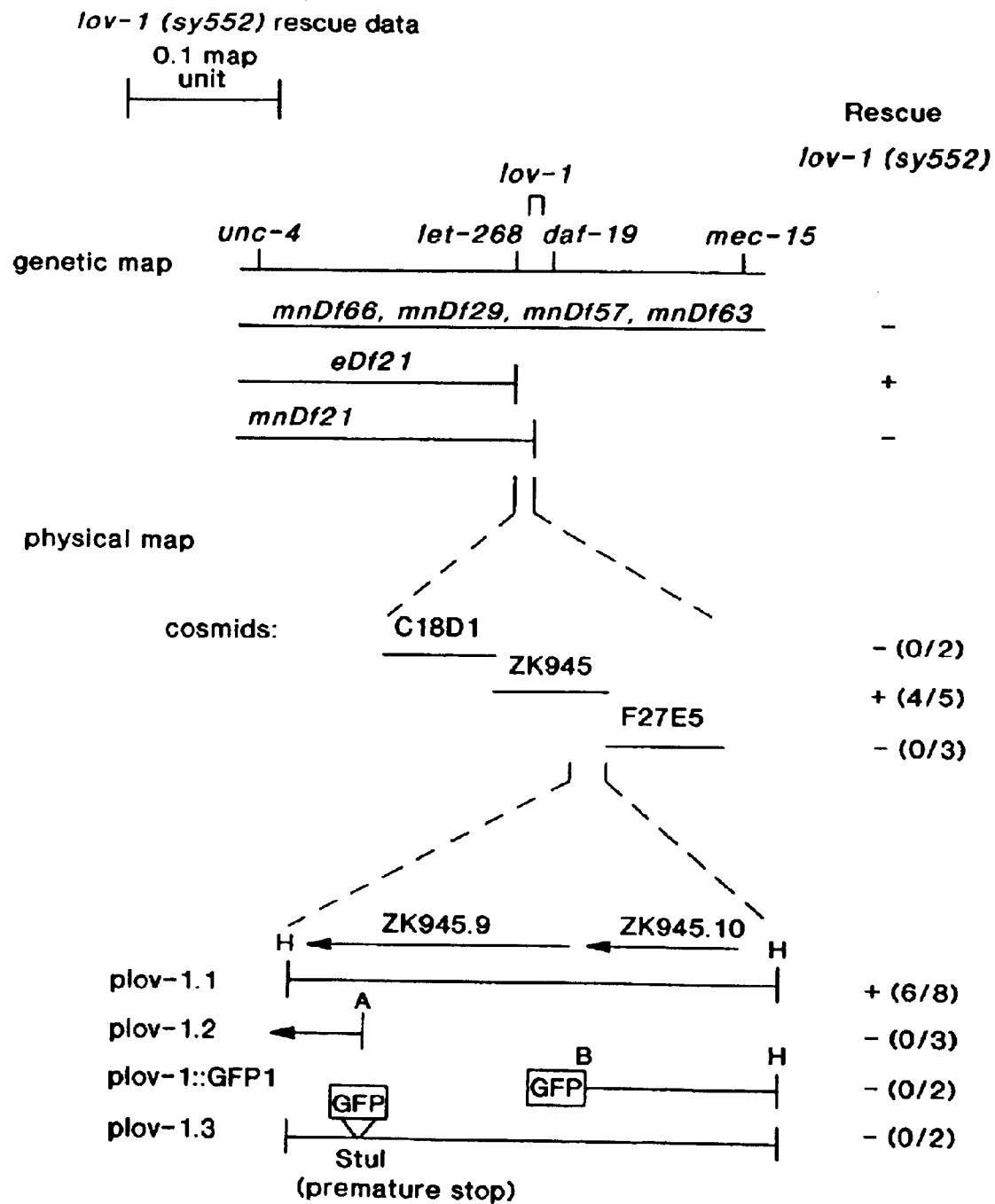
FIG. 2 depicts the molecular nature of lov-1. a, Genetic and physical maps of the lov-1 region on chromosome 2. Genetic markers are shown. Boundaries of a lov-1 deletion (mnDf21) and non-deletion (eDf21) are indicated. +designates; rescue of lov-1(sy552) mutant males. Numbers in parentheses indicate the ratio of rescuing stable lines to total stable lines examined. b, lov-1 gene structure. Exons are boxed. Genefinder predicts two ORFs, ZK945.10 (9 exons) and ZK945.9 (19 exons). RT-PCR reveals lov-1 corresponds to the combination of ZK945.10 and ZK945.9. The arrow indicates the 1059 bp deletion in lov-1 (sy582Δ) c, lov-1::GFP (green fluorescent protein) expression constructs, patterns, and phenotypes in wild-type background. d, lov-1 encodes a membrane associated protein with homology to the polycystin and voltage-activated channel families. A schematic representation of LOV-1 is shown to demonstrate domains of the protein. These include the amino terminus that is serine/threonine rich with multiple potential glycosylation sites, an ATP/GTP binding domain (indicated by the asterisks), followed by two polycystin blocks of homology. Block 1 is exclusively homologous to PKD1, while Block 2 shows homology with all polycystins and also the family of voltage activated $CA^{2+}$ channels. Block 1 is a conserved domain of unknown function, that also occurs at the N-terminus of most 5-lipoxygenases.

The lov-1 gene was cloned by genetic mapping and transformation rescue of the sy552 behavioral defects (FIG. 2a). mnDf2I/sy552, mnDf83/sy552 and sy552/sy552 males are phenotypically indistinguishable; therefore, sy522 is reduction or loss of function mutation in lov-1. This conclusion is supported by the observed recessive nature of sy552. A 16.9 kb HindIII subclone (plov-1.1) of the cosmid ZK945 rescued response and Lov defects of sy552 (FIG. 2a). Both a 6.7 kb HindIII-BamHI fragment from plov-1.1 (plov-1::GFP1) and a 14.1 kb HindIII-StuI frameshift in plov-1.1 (plov-1.3) fail to rescue sy552 defects (FIG. 2b) yet act in a dominant negative (DN) manner in wild-type males with respect to Lov behavior (FIG. 2c). Wild-type males expressing either plov-1::GFP or plov-1.3 are Lov defective. These transgenic males exhibit a wild-type response to hermaphrodite contact. Without being bound by a theory, the differences in sy552 and transgenic DN pheno-types might be attributed to dosage or mosaicism.

Figure 2B:
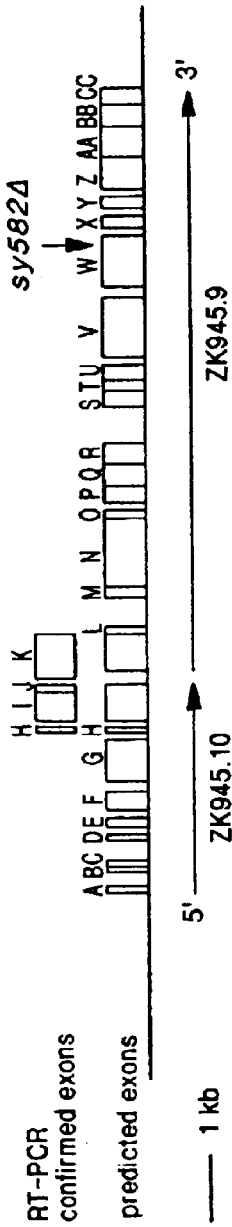
Figure 2C:
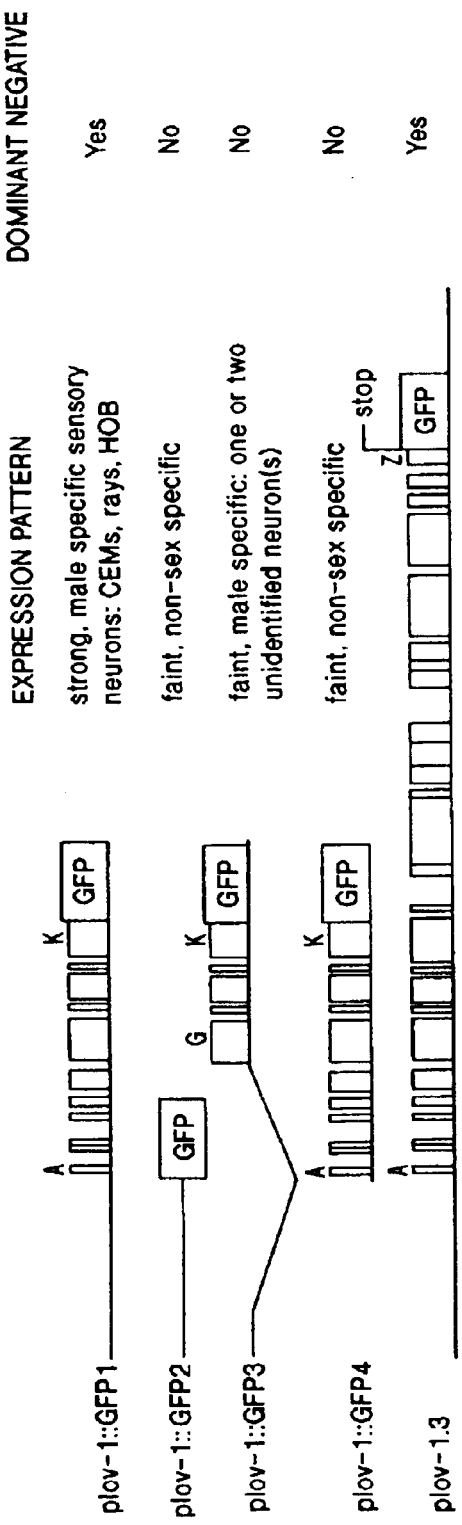
Figure 2D:
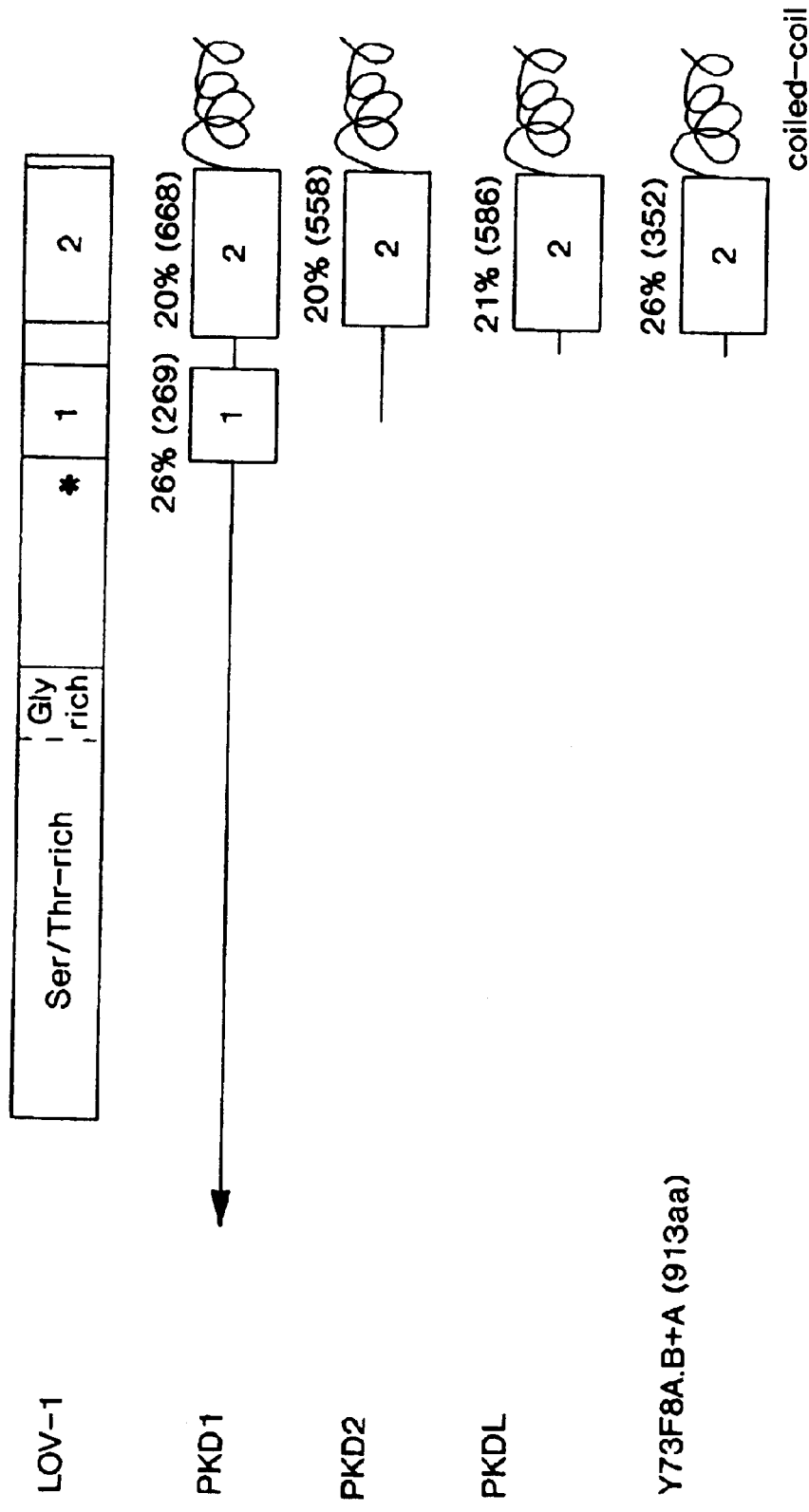

FIG. 2b illustrates the intron-exon boundaries of the lov-1 gene. Using RT-PCR with lov-1 specific primers and him-5 mRNA, it was found that lov-1 encodes one transcript corresponding to Genefinder-predicted ORFs, ZK945.10 and ZK945.9 (FIG. 2b), which had been thought to be two genes. Lov-1 encodes a predicted 3178 amino acid membrane-bound protein (see SEQ ID Nos. 3 and 4) with a serine-threonine rich extracellular domain homologous to mucins (Carraway et al. (1995) *Trends Glycoscience Glycotechnology* 7:31–44), a polycystin homology block 1 (26% identity), and a carboxy terminal polycystin block 2 with 20% identity to polycystin proteins 1, 2, and 2, encoded by the PKD1, PKD2, and PKDL (polycystic kidney disease) genes, respectively (FIG. 2d). A Kyte-Doolittle hydropathy plot predicts multiple transmembrane domains; although no signal peptide is predicted in LOV-1. Mucins are highly glycosylated extracellular proteins thought to serve cell adhesion and/or protective functions (Carraway et al. (1995) *Trends Glycoscience Glycotechnology* 7:31–44).

Similarity between exons W (for PKD1 only), X, Y, Z, AA, BB, and CC of lov-1 and PKD1, PKD2, and the family of voltage-activated calcium and potassium channels in the six transmembrane spanning region has been observed (Mochizuki et al. (1996) *Science* 272:1339–1342). This extends to PKDL (Nomura et al. (1998) *J. Biol. Chem*, 273:25967–25973). LOV-1 lacks the $Ca^{2+}$ binding EF-hand of polycystin 2 and L, and a coiled-coil domain of all three polycystins (FIG. 2d), which has been shown to mediate hetero- and homotypic interactions between polycystin 1 and polycystin 2 (Qian (1997) *Nature Genetics* 16:179–183; Tsiokas et al. (1997) *Proc. Natl. Acad. Sci. USA* 94:6965–6970). Block 2 also shows limited homology with the trp (transient receptor potential) family of channels (Montell et al. (1989) *Neuron* 2:131 3–1323). The critical difference between voltage-gated and trp channels is the presence of a positively charged S4 transmembrane domain that acts as a voltage sensor (Montell et al. (1989) *Neuron* 2:1313–1323). LOV-1 more closely resembles voltage-gated channels in this respect. A frameshift disruption in lov-1 (plov-1.3) one residue away from a corresponding nonsense mutation in human PKD2 (Mochizuki et al. (1996) *Science* 272:1339–1342) destroys the ability to rescue lov-1(sy552), as mentioned above. The construct plov-1.3 encodes a truncated protein lacking the polycystin block 2/channel domain. These results demonstrate that the polycystin block 2/channel domain is essential for LOV-1 function, and indicate that functional as well as structural similarities might exist between LOV-1 and PKD-2. LOV-1 also possesses a nucleotide-binding domain (FIG. 2d) that is not present in the human polycystins. The structure of LOV-1 is also indicative of a role in signal transduction.

The lov-1 gene product appears to be a membrane spanning protein that includes an extracellular domain with a serine/threonine-rich mucin-like domain, an ATP-binding domain, and small cytoplasmic tails that mediate interaction with other members of the pathway, including a pkd-2 gene product that is also a membrane spanning protein, with six membrane domains, and a cytoplasmic EF-hand. Interaction of these proteins lead to the observed phenotypic response. In *C. elegans* this response can be detected as a clearly identifiable phenotype. Hence, *C. elegans* and mutants thereof can serve as a test system for identifying compounds that alter this pathway and also for identifying other gene products involved in the pathway.

Lov-1 Gene

In an exemplary embodiment, the complement of the nucleic acid sequence of the lov-1 gene from *C. elegans* is provided. Corresponding genes from other nematodes may be identified, such as by using the nucleic acid provided herein and screening an appropriate library, genomic or cDNA library, using standard procedures. Alternatively, databases of sequences may be searched, and the genes from other nematodes homologous to those provided herein identified, again using standard searching and alignment programs.

SEQ ID NO. 3 is the complement of the genomic sequence of the lov-1 gene. It includes open reading frames (ORFs) between nucleotides 15760 to 27880 of cosmid ZK945 (nucleotides 1 to 12121 of SEQ ID NO.3) and nucleotides 1–564 of cosmid F27E5 (nucleotides 12122 to 12685 of SEQ ID NO.3). It was found herein, however, that ZK945 and F27E5 overlap from nucleotides 27881 to 27981 and nucleotides 1 to 101, respectively (the overlap region includes nucleotides 12122 to 12222 in SEQ ID NO.3), thereby providing a single, rather than two, ORFs.

It been thought that the open reading frame in cosmid ZK945 (the "ZK945.9" gene; nucleotides 1 to 9164 of SEQ ID NO.3), and the open reading from in cosmid F27E5 (the "ZK945.10" gene; nucleotides 9415 to 12685 of SEQ ID NO.3) encoded two genes. DNA sequence analysis of RT-PCR generated cDNA clones from him-5(e1490) RNA revealed three exons (exons I, J and K in FIG. 2B) in the junction between ZK945.10 and ZK945.9: one from nucleotides 25195 to 25742 of the ZK945 cosmid (nucleotides 9436 to 9983 of SEQ ID NO. 3); a second from nucleotides 25071 to 25151 of the ZK945 cosmid (nucleotides 9312 to 9392 of SEQ ID NO. 3); and a third initiating at position 25021 in the ZK945 cosmid (nucleotide 9262 of SEQ ID NO. 3). This demonstrated that the lov-1 gene encodes one large transcript corresponding to ORFs in ZK945.10 and ZK945.9, spanning what had previously been thought to encode two proteins.

As noted above, FIG. 2B depicts the lov-1 genomic structure (exons shown as boxes, introns as lines). With reference to FIG. 2B, the coding sequence in the gene set forth in SEQ ID No. 3 (noting that SEQ ID 3 sets forth the non-coding strand) is as follows:

Complement (Join (12500 . . . 12685)—Exon A; (12266 . . . 12451)—Exon B; (12085 . . . 12217)—Exon C; (11683 . . . 11823)—Exon D; (11498 . . . 11637)—Exon E; (11128 . . . 11452)—Exon F; (10268 . . . 10899)—Exon G; (10138 . . . 10216)—Exon H; (9436 . . . 9983)—Exon I; (9312 . . . 9392)—Exon J; (8685 . . . 9262)—Exon K; (8557 . . . 8635)—Exon L; (7830 . . . 7997)—Exon M; (6774 . . . 7786)—Exon N; (6648.. .6728)—Exon O; (6305 . . . 6598)—Exon P; (6006 . . . 6255)—Exon Q; (5732 . . . 5958)—Exon R; (4849 . . . 5076)—Exon S; (4698 . . . 4799)—Exon T; (4383 . . . 4651)—Exon U; (3336 . . . 4328)—Exon V; (2229 . . . 3094)—Exon W; (1976 . . . 2181)—Exon X; (1635 . . . 1930)—Exon Y; (1043 . . . 1591) Exon Z; (625 . . . 999)—Exon AA; (329 . . . 572)—Exon BB; (1 . . . 270)—Exon CC).

The LOV-1 amino acid sequence is set forth in SEQ ID NO. 4 The following table summarizes the above.

TABLE 3

Comparison of Sequence ID No. 3 with source Cosmids[†]

| EXON | SEQ ID 3 | ZK945 | F27E5 |
|---|---|---|---|
| A | 12500 . . . 12685 | | 379 . . . 564 |
| B | 12266 . . . 12451 | | 145 . . . 330 |
| C | 12085 . . . 12217 | 27844 . . . 27976 | |
| D | 11683 . . . 11823 | 27442 . . . 27582 | |
| E | 11498 . . . 11637 | 27257 . . . 27396 | |
| F | 11128 . . . 11452 | 26887 . . . 27211 | |
| G | 10268 . . . 10899 | 26027 . . . 26658 | |
| H | 10138 . . . 10216 | 25897 . . . 25975 | |
| *I | 9436 . . . 9983 | 25195 . . . 25742 | |
| *J | 9312 . . . 9392 | 25151 . . . 25071 | |
| *K | 8685 . . . 9262 | 24444 . . . 25021 | |
| L | 8557 . . . 8635 | 24316 . . . 24394 | |
| M | 7830 . . . 7997 | 23589 . . . 23756 | |
| N | 6774 . . . 7786 | 22533 . . . 23545 | |
| O | 6648 . . . 6728 | 22407 . . . 22487 | |
| P | 6305 . . . 6598 | 22064 . . . 22357 | |
| Q | 6006 . . . 6255 | 21765 . . . 22014 | |
| R | 5732 . . . 5958 | 21491 . . . 21717 | |
| S | 4849 . . . 5076 | 20608 . . . 20835 | |
| T | 4698 . . . 4799 | 20457 . . . 20558 | |
| U | 4383 . . . 4651 | 20142 . . . 20410 | |
| V | 3336 . . . 4328 | 19095 . . . 20087 | |
| **W | 2229 . . . 3094 | 17988 . . . 18853 | |
| X | 1976 . . . 2181 | 17735 . . . 17940 | |
| Y | 1635 . . . 1930 | 17394 . . . 17689 | |
| Z | 1043 . . . 1591 | 16802 . . . 17350 | |
| AA | 625 . . . 999 | 16384 . . . 16758 | |
| BB | 329 . . . 572 | 16088 . . . 16331 | |
| CC | 1 . . . 270 | 15760 . . . 16029 | |

*exons I, J, K at the junction of ZK945.10 and ZK945.9 (as determined by RT-PCR analysis, and not predicted by the GeneFinder program)
**the sy582 lov-1 mutant has a 1059 bp deletion beginning in exon W at position 2267 of SEQ ID NO. 3 (18026 of the ZK945 cosmid) and ending at position 1209 of SEQ ID NO. 3 (16968 of the ZK945 cosmid).
[†]The GenBank accession numbers for ZK945 and F27E5 are (GenBank Accession No. Z48544) and (GenBank Accession No. Z48582), respectively.

Exemplary Knockout Mutant Sy582

A genomic deletion of lov-1 in a PCR screen of EMS mutagenized worms was isolated. lov-1(sy582Δ) encodes a truncated protein lacking the polycystin/cation channel homology domain (FIG. 2d). Like sy552, lov-7(sy582Δ) males exhibit defects in response and Lov behaviors (Table 2), as well as low mating efficiency with dpy-17 but not unc-52 partners. sy582Δ is recessive and fails to complement sy552. The truncated protein produced by lov-1 (sy582Δ) does not act as a dominant negative in contrast to the truncated protein produced by plov-1.3 (see below). This difference might be due to a dosage effect of the plov-1.3 transgene. These results confirm that the polycystin block 2/cation channel domain is essential for LOV-1 activity and indicate that lov-1(sy582Δ) is completely defective in LOV-1 function.

The lov-1 (sy582) mutant is a 1059 bp deletion of nucleotides 18026 to 16968 of ZK945 (nucleotides 2267 to 1209 of SEQ ID NO. 3). The deletion, which begins in exon W, removes the majority of the PKD homology block 2 (a total of 308 amino acids, beginning at amino acid 2520 and ending at amino acid 2827 of the sequence set forth in SEQ ID NO. 4) and continues to read in-frame to the end of the sequence set forth in SEQ ID NO. 4. This results in a protein of 2870 amino acids with the amino acid sequence set forth in SEQ ID NO. 15.

Other mutants may be prepared by any method known to those of skill in the art, including directed mutagenesis of the gene in a selected nematode or random mutagenesis and selection for the altered male mating behavior in the lov and/or response, preferably both behaviors. Preferred regions for deletion include the exon A. Precise size of the deletion and or locations to delet can be determined empirically using standard routine methods based upon the disclosure herein, which identifies the gene and the resulting phenotype. Other mutations including insertions and point mutations that alter these behaviors are also contemplated and can be readily prepared.

Expression Patterns of Lov-1

To elucidate the cells in which lov-1 acts to affect male mating behaviors, the expression pattern of lov-1-::GFP reporter genes was examined (see Example 2 and FIG. 4). These experiments reveal regulatory regions in the lov-1 gene. A partial translational fusion containing 2.8 kb of upstream sequence and 3.9 kb of lov-1 (plov-1::GFP1) directs male-specific expression in male-specific sensory neurons (FIG. 2c and FIG. 4). Conversely, shorter versions of plov-1::GFP1 are not expressed in the same set of male-specific neurons nor exclusively in male-specific sensory neurons and do not act as DNs (FIG. 2c). Similar results were observed with pkd-2 mutants (see Example 2 and FIG. 4).

Nematode Pkd-2

A search for a homolog of LOV-1 was performed to ascertain whether nematodes possess a PKD2 ortholog. A BLAST search of the Sanger Center C. elegans genome database revealed a possible LOV-1 homologi: Y73F8A.B. This cosmid encodes a protein with 27% identity to PKD2 and possesses the coiled-coil domain of all polycystins. It is shown herein that Y73F8A.B and Y73F8A.A encode one transcript that is the C. elegans ortholog of human PKD2 (FIG. 2d and FIG. 3). The resulting nematode gene, designated pkd-2, cDNA and encoded protein are provided herein.

Figure 3B:
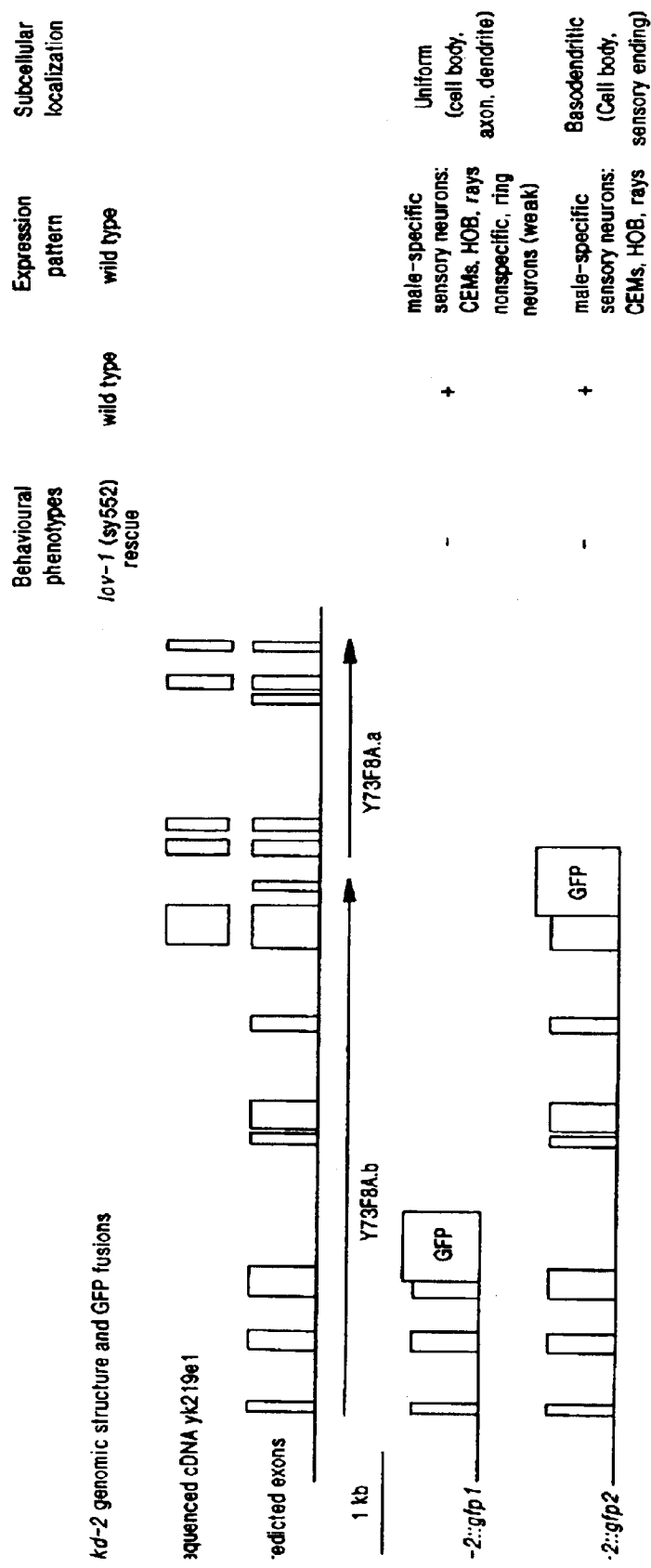
Figure 4A:
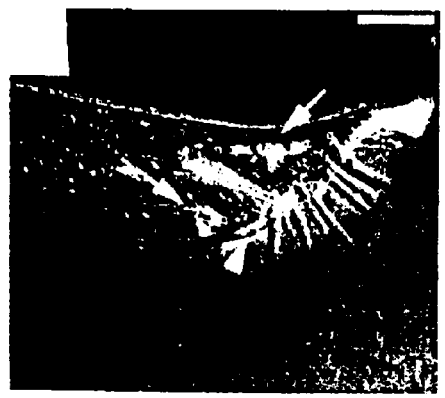
Figure 4B:
Figure 4C:
Figure 4D:
Figure 4E:
Figure 4F:
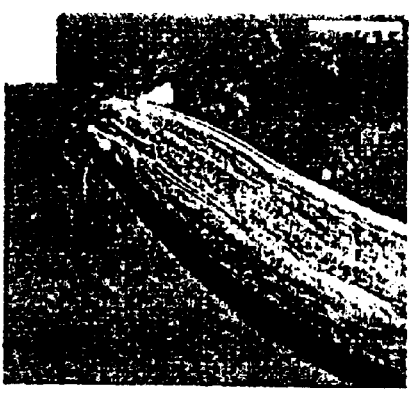

The C. elegans gene is exemplified herein. SEQ ID No. 5, which sets forth the complement of the coding strand, is provided. It contains nucleotides 1605 to 9677 of C. elegans cosmid Y73F8A (GenBank Accession No. AL132862), which correspond to nucleotides 1 to 8073 of SEQ ID No. 5. The sequence of the encoded protein is set forth in SEQ ID No. 6. FIG. 3B shows pkd-2 genomic structure (exons shown as boxes, introns as lines). The cDNA yk219e1 was sequenced and corresponds to the 3' end of pkd-2.

FIG. 3B shows the pkd-2 genomic structure (exons shown as boxes, introns as lines). The coding sequence in the gene set forth in SEQ ID No. 5 is produced as follows:

Complement (Join (7980 . . . 8073)—Exon 1; (7396 . . . 7585)—Exon 2; (6765 . . . 7045)—Exon 3; (5153 . . . 5283)—Exon 4; (4863 . . . 5104)—Exon 5; (3931 . . . 4158)—Exon 6; (2875 . . . 3424)—Exon 7; (1957 . . . 2208)—Exon 8; (1542 . . . 1795)—Exon 9; (367 . . . 505)—Exon 10; (1 . . . 87)—Exon 11.

As discussed above, the architecture of LOV-1, including a large extracellular amino terminus, Block 1, and Block 2, is similar to that of human PKD1; the architecture and sequence of PKD-2 is similar to PKD2. Taken together, LOV-1 and PKD-2 appear to be part of a multi-component complex and pathway. Further genetic analysis of Lov behavior confirms this.

Knockout Mutation of Pkd-2

A knockout mutation can be prepared by any method known to those of skill in the art. A deletion mutant, designated sy606 was produced (see, Examples for primers used). A 2397 bp deletion from nucleotides 8338 to 5942, starting in intron 3 and ending in intron 5, removing exons 4 and 5 (including the partial transmembrane spanning domain S1 and the polycystin motif) with the new splice in a different reading frame resulting in a stop codon (TGA) at 5736, produced a knockout mutation. The resulting phenotype was the same as that resulting from a knockout of lov1, thereby demonstrating that the two proteins are part of the same pathway that results in the observed phenotype.

The pkd-2 (sy606) mutant contains a 2397 bp deletion of nucleotides 8338 to 5942 of Y73F8A (nucleotides 6734 to 4338 of SEQ ID NO. 5), starting in intron 3 and ending in intron 5, removing exons 4 and 5 (including the partial transmembrane spanning domain S1 and the polycystin motif) with the new splice in a different reading frame. This results in a stop codon (TGA) at nucleotide 5728 (nucleotide 4124 in SEQ ID NO. 5). The sequence of the protein encoded by the pkd-2 deletion mutant (sy606) is set forth in SEQ ID NO. 16.

TABLE 4

Comparison of Sequence ID No. 5 with source Cosmid

| EXON | SEQ ID 5 | Y73F8A |
|---|---|---|
| 1 | 7980 . . . 8073 | 9584 . . . 9677 |
| 2 | 7396 . . . 7585 | 9000 . . . 9189 |
| 3 | 6765 . . . 7045 | 8369 . . . 8649 |
| 4 | 5153 . . . 5283 | 6757 . . . 6887 |
| 5 | 4863 . . . 5104 | 6467 . . . 6708 |
| 6 | 3931 . . . 4158 | 5535 . . . 5762 |
| 7 | 2875 . . . 3424 | 4479 . . . 5028 |
| 8 | 1957 . . . 2208 | 3561 . . . 3812 |
| 9 | 1542 . . . 1795 | 3146 . . . 3399 |
| 10 | 367 . . . 505 | 1971 . . . 2109 |
| 11 | 1 . . . 87 | 1605 . . . 1691 |

*the sy606 pkd-2 mutant has a 2397 bp deletion of nucleotides 8338 to 5942 of Y73F8A (GenBank Accession No. AL132862; nucleotides 6734 to 4338 of SEQ ID NO. 5), starting in intron 3 and ending in intron 5, removing exons 4 and 5, with the new splice being in a different reading frame and resulting in a stop codon (TGA) at nucleotide 5728 (4124 in SEQ ID NO. 5).

Other such deletions may be similarly produced by deleting any portion that eliminates at least one of the observed phenotypic behaviors associated with the lov-1 and pkd-2 pathway. Preferable targets for these deletions are those that destroy reading frames resulting in non-functional truncated proteins, deletions that eliminate transcriptional or translational control regions, deletions in the first exon or exon such that the deletion (or insertion or point mutation) eliminates or substantially attenuates activity of the encoded protein as evidenced by altered phenotype.

The Lov-1 and Pkd-2 Genes Encode Homologs of the Polycystins

It is shown herein that the lov-1 and pkd-2 genes and gene products are homologs of mammalian polycystins, particularly PKD1 and PKD2, respectively. As such nematodes that express these genes, and/or mutants of the genes can serve as models to study the expression of the genes, the function of these genes, to identify additional genes in the pathway, and for screening for compounds that will serve as lead compounds for treatment of PKD in mammals, particularly humans.

Neither the precise functions of the polycystins nor the molecular basis of kidney cystogenesis is known. The results provided herein show that the homologs of the polycysins act together in a pathway, that appears to be a signal transduction pathway, in sensory neurons. It has been postulated that human polycystin 1 and polycystin 2 function as an ion channel (Torres et al. (1998) Current Opinion in Nephrology and *Hypertension* 7:159–169). Further supporting this conclusion are the results of others that have indicated that human PKD2 is associated with the activity of a cation channel. These results were obtained using cell-expression and electrophysiological approaches to examine the potential channel function of a protein called PCL (polycystin-like) that had been identified in the human expressed sequence-tag database by its sequence similarity with PKD2 (Chen et al. (1999) *Nature* 401:383–386). PCL was expressed in *Xenopus oöcytes* by microinjecting synthetic mRNA, and the channel properties were studied using the two micro-electrrode voltage clamp and patch-clamp techniques. It was found that PCL is a non-selective cation channel that is permable to sodium, potassium and calcium. It is more permeable to calcium. Thus, PCL and PKD2 may be cation-channel subunits.

Hence, as shown herein, PKD1-related proteins act as receptors that regulate the activity PKD2-related proteins. The two proteins are part of a conserved pathway that appears to be a signalling mechanism in which the translocation of ions acts as a second messenger.

Exemplary Strains

Strains that exhibit one or more of the behaviors are provided. The strains may be prepared by mutagenizing wild-type or other strains with other desirable characteristics and selecting for those with the behavioral phenotype.

Strain PS3152 is an N2 strain with a deletion in lov-1 lov-1(sy582)).

Strain PS2816 has the lov-1(sy552) deletion in a background with a him-5 (high incidence of males) and plg-1, which is a mutation that causes the male to use a gelatinous mating plug (which can be used to visualize mating).

Strain PS2817 is a paralyzed (unc-52) version of PS2816.

Strain PS3150 has the same deletion in a background with a him-5 (high incidence of males) and ts lethal marker (pha-1). A strain with a ts marker is a good recipient for transformation. strain recipient for transformation-pha-1 marker -, any marker can be used.

PS3151 is the same as PS2815 without the plg-1.

PS3149 has a pha-1 marker, in a him-5 background and transformed with an extrachromosomal element containing a lov-1::GFP1 construct and pha-1(+) DNA.

Anbother strain is a him-5 strain with the lov-1(sy582) deletion.

PS3400 has a deletion mutation in pkd-2; it is pkd-2 (sy606).

PS3401 is a him-5 strain with the lov-1(sy582) deletion.

PS3377 is pkd-2(sy606) in a him-5 background.

These and other strains may be used in the assay methods described herein or in any assay that assesses the pathways and sensory functions which lov-1 and/or pkd-2 are involved or that can be used for identifying compounds that affect this pathway(s).

Assays for Screening Compounds and for Identifying Mutants with Observable Lov and/or Response Defective Behavior Assays for identifying additional genes in the pathway, to assess the activities of proteins in the pathway, to identify regulators of gene expressions and factors involved in gene expression of genes in this pathway, and for screening for compounds that affect polycystin function are provided. Compounds that affect polycystin function in a nematode are candidates for further investigation and serve as leads for compounds that may be therapeutically useful for treating mammalian PKDs.

Identification of components of the PKD pathway will aid in understanding the etiology of the disease and permit identification of disease markers and defective genes, thereby permitting development of reagents for diagnostic tests and identification of therapeutic targets and therapeutic agents.

The assays may be adapted for high throughput methods, particularly by using multiwell plates, such as 24, 96, 384 wells or higher densities, and automating many of the steps. By using multiple wells, for example, many compounds can be screened. The results can be automated by using video or other recording means to record the behavior in each well. Viewing using such means is facilitated by visually labeling the animals, such as by introduction of reporter gene constructs that will be expressed in areas of interest, such as the vulval and tail region of the hermaphrodite, to render the animal visible to a camera. If a GFP is used, for example, the camera will be equipped with an appropriate filter to screen out all but the green glow. Other ways of making the animals visible, include, for example, use of plg-1 animals, which leave a visible gelatinous trail as they move through the agar.

Precise protocols for culturing and nematodes, producing mutants and transgenics, and for observing behaviors are well known to those of skill in the art.

Assays Using Wild-type Males

Behavioral Screens

In these assays males will be identified that exhibit abnormal behavior, particularly abnormal Lov and/or response behaviors, thereby detecting components of PKD function, signaling or regulators, or identifying compounds that are candidates for affecting PKD function, signaling or regulation. A behavioral assay is depicted in FIG. 1 and described herein.

The tests are performed by placing male nematodes on an agar surface, such as a petri dish or microtiter plate with an agar surface, that is seeded with anything, including bacteria or chemoattractants, such as NaCl, that will keep the males in a field of view. One or more mating partners, such as a hermaphrodite, is placed on the plate and the behavior is recorded, such as by direct observation, review of a video tape, or any method whereby the behavior can be recorded.

For example, observations of the behaviors can be observed using young adult hermaphrodites, such as unc-31(e169) hermaphrodites, on a lawn of bacteria, such as *E. coli*. The use of unc-31 hermaphrodites, which are sluggish, makes it easier for males to keep pace with them.

For drug screening assays, the effects of a test compound are examined. The males are treated with a compound, such as by culturing them in the presence of the compound., or including the compound in the mating dish, or pretreating the males with the compound. For analysis of mutants, males from parents or grandparents that had been mutagenized with chemical and/or radiation are tested.

In either embodiment, the behavior of the males is observed by looking for one or both, preferably both, of the Lov and 'response' behaviors compared to controls, untreated males for the drug screening assays or wild-type for the mutant assays. If behavior of the treated males differs from controls, then the compound has some activity and is selected for further analysis.

For the assays of mutants, if the behavior of the males differs from the controls, the mutation(s) are identified, such as by mapping. The mutant gene is then identified, genetically analyzed and its role in the pathway elucidated.

These methods as well as the others provided herein can be adapted for high throughput analysis, including automation, such by videotaping and image processing. For image processing the animals can be visually labeled, such as by expressing, a reporter gene, like GFP, to produce stable transgenic strain of some construct of GFP with any promoter that would direct expression with sufficient intensity or in a sufficient number of cells to visualize the behavior. For example, a glowing vulva and tail would permit visualization of the Lov and response behaviors. Suitable genes for linkage to a reporter are any that are expressed in the animal to permit such visualization. Such markers include, but are not limited to, autofluorescence of the male spicule, egl-5-gfp, and of the hermaphrodite vulval region lin-11-gfp.

Measurements can be performed by any method known to those of skill in the art (see, e.g., Liu et al. (1995) Neuron 14:79–89). Briefly, measurements can be obtained as follows: time is kept with a stopwatch or key stroke recorder on a computer to record an 'ethogram', and distances estimated by eye and confirmed from micrographs taken of the behavior. Mating behavior is sensitive to a number of variables, including the moisture level of the plates, which are not used if they are more than a week old, and hermaphrodite age. Hence controls and test animals are carefully matched. At least three hermaphrodites are used per male to control for hermaphrodite specific behaviors.

Mating Efficiency Assays

As noted above, deletion of lov-1 compromises but does not abolish the ability to mate. The mutant male can mate with paralyzed or moving impaired partners. To perform these assays, wild-type males are treated with a test compound or mutagenized, and males that sire fewer cross-progeny compared to wild-type or cannot sire cross-progeny with moving partners are identified.

To detect whether the progeny are those of the males rather than the hermaphrodites, sperm defective hermaphrodites can be used. Preferably the hermaphrodites are temperature-sensitive (ts) sperm defective. Alternatively, the mating can be detected by using a visual marker, such as using short and fat (Dpy;Dumpy) hermaphrodites, or males that express a visually or otherwise detectable transgene, such as fluorescent proteins (FPs), including, but not limited to blue fluorescent proteins and green fluorescent proteins (GFPs), and looking for the transgene in progeny could have a transgene transferred into the progeny by the mating and detectable. If a FP is used as a marker, glowing offspring are detected.

Progeny can also be detected by measuring the density of the resulting culture and a ts sperm defective hermaphrodite. If there are lot of progeny, it can be inferred that the males have mated, since the hermaphrodite is sperm defective.

Assays Using Mutant Males

Suppressor and enhancer genetics can be used to assign functions to genes, to assign genes to pathways, to identify the key switches in these pathways and to provide a sensitive assay to identify new genes in a pathway and lead compounds that modulate the activity of genes and/or gene products in the pathway.

Suppressor screen In these assays, the process starts with a lov-1 mutant and restoration of one or both behaviors is assessed, thereby identifying compounds or mutations that restore the defect. Restoration can occur, for example, by by-passing the defective gene, such as constitutive expression of a gene further down the pathway that had previously required lov-1 or pkd-2 activity. Alternatively, a mutation could knock-out the activity of another gene that suppresses the activity of lov-1 or pkd-2, thereby restoring the pathway. These assays will identify other genes in the pathway. These assays can also identify a compound that corrects defects in the pathway, thereby providing a promising therapeutic lead for treatment of APKD.

Enhancer screen In these assays, the defect is exacerbated by looking for mutations or compounds that increase the penetrance of the phenotype caused by the lov-1 or pkd-2 mutations for either or both of the 'response' and Lov defect. This is achieved by screening for males that cannot sire cross progeny with paralyzed hermaphrodite mating partners or by observing the behavior directly. The genes with mutations responsible for the increased penetrance that differ are identified, and those that are not lov-1 or pkd-2 are selected. Mammalian, particularly human, homologs of the selected genes are identified, and tested to assess their role in PKD diseases, such as, for example, by screening PKD patients for alterations in the homologous (or orthologous) gene, analysis of mouse model knockout mutations, or other methods known to those of skill in the art.

Assays for Identifying the Role of PKD Proteins in Sensory Function

As shown herein, lov-1 and pkd-2 are expressed in CEM neurons, indicating that they have activity in other sensory functions, such as finding a mating partner at a distance, i.e. sexual chemotaxis or kinesis, where the male randomly finds a hermaphrodite and then stays nearby. Hence sexual or chemoattraction assays can be used to study PKD function. To perform this assay, for example, put males that are mutagenized or treated with a test compound on a surface containing at particular locations hermaphrodites and a control (i.e, males, or other hermaphrodites, or buffer), The proportion of fraction of males that choose the hermaphrodites compared to the control is scored. If the male is defective in this sensory function, it will not distinguish between males and hermaphrodites.

Other sensory functions can be assessed to identify the role, if any, of PKD genes in the functions.

Assays that Use Dominant Negative Forms of PKD in Nematodes or in Other Cells to Identify Mutations and/or Compounds that Inhibit or Otherwise Alter PKD Function Transgenic nematodes that express a version of the LOV-1 or PK2D protein that inhibits the activity of LOV-1 and/or PKD-2 as assessed by manifestation of the altered LOV and/or response phenotypic behavior(s) are used in these assays.

As described above, a dominant negative mutation is a mutation that encodes a polypeptide that when expressed disrupts that activity of the protein encoded by the wild-type gene (see, Herskowitz (1987) Nature 329:219–222). A cloned gene is altered so that it encodes a mutant product that upon expression in an organism or cell containing the wild-type gene, expression of the wild-type product is inhibited or eliminated. As a result, the cell or organism is deficient in the product. The mutation is "dominant" because its phenotype is manifested in the presence of the wild-type gene, and it is "negative" in the sense that it inactivates the wild-type gene function. It is possible to do this because proteins have multiple functional sites. Hence an assay that identifies a dominant negative mutation can identify functional activities of a protein.

In this instance, the assays use transgenic nematodes that contain such a dominant negative lov-1 or pkd-2 transgene. In certain assays, the transgenic mutants are mutagenized, and mutants that lose a remaining activity are selected. The mutations and genes responsible for the loss are identified. Corresponding mammalian, particularly human, genes, such as by searching databases for homologs or by probing libraries with the nematode genes, are identified.

In the compounds screening assays that employ these transgenic nematodes, compounds that interfere with a remaining activity of the lov-1 or pkd-2 gene are identified. For example, as shown herein, plov-1.3 (plov-1.3 encodes a truncated protein lacking the polycystin block 2/channel domain) has a dominant negative effect in transgenic nematodes affecting only the Lov behavior, not Response. Compounds that rescue this dominant negative effect include those that interfere with the synthesis, binding or function of the amino-terminal region of the LOV-1 protein.

Since the dominant negative effect only affects the Lov response, a stable transgenic nematode strain that expresses a dominant negative of lov-1, can be used to screen for compounds and mutations that further affect Response well.

Assays Based on Localization and Trafficking of LOV-1 and/or PKD-2 Within a Cell or Cells To identify regulators and factors necessary for synthesis and transport of LOV-1 and/or PKD-2 proteins, strains in which LOV-1 and PKD-2 are expressed linked to a detectable label, such as a fluorescent protein, can be and have been produced. It has been shown that these proteins are expressed in the ciliated endings and in the baso-dendritic compartment of HOB, ray neurons or CEM neurons.

These strains, such as PS3149, described above, can be used to study the trafficking patterns of LOV-1 and PKD-2 and cellular location(s) of the proteins in the animal by looking for mutants thereof that have altered trafficking and/or altered localization of one or both of these proteins. The mutations can be mapped, genetically analyzed and the genes identified. Such genes could serve as therapeutic or diagnostic targets.

Assays for Identification of Transcriptional Regulators of Expression of Lov-1 and/or Pkd-2

To identify transcriptional regulators of lov-1 or pkd-2, a screen for loss or alteration of expression of either gene is provided. Transgenic nematodes with a reporter gene, such as a gene encoding a FP or lacZ or other detectable product, linked to the nucleic acid encoding lov-1 or pkd-2 is used. The animal is mutagenized or treated with a test compound and loss of expression or reduction in expression of either gene is assessed by detecting, such as by observing under a dissecting or compound microscope or other means, including whole animal sorting, the number of cells that express the detectable marker, such as a FP.

As a control, to avoid detection or identification of non-specific effects, an unrelated gene, such as lin-3, linked to a reporter, is expressed in other cells in these animals. Only mutants that exhibit changes in expression of lov-1 or pkd-2, but not expression of the other gene, are selected for identification and mapping of the mutation. If expression of the other gene is affected also, then mutation is likely affecting a general process and would not be of interest.

These assays will identify regulators of and factors that affect lov-1 and pkd-2 expression, which regulators and factors could serve as therapeutic or diagnostic targets, or which regulators and factors can aid in developing an understanding of the development and progression of PKD in mammals.

Visual Screen Based on Clumping Behavior

Wild type adult males isolated from hermaphrodites will clump together on a plate with a lawn of bacteria. In contrast, lov-1 and pkd-2 mutant males do not exhibit this clumping behavior. Rather, lov-1 and pkd-2 mutant males are randomly dispersed in the bacterial lawn. This assay may be used for a variety of purposes, including, but not limited to, he identification of compounds that inhibit wild type male clumping behavior, compounds that restore clumping behavior to lov-1 or pkd-2 mutants, and the identification of genetic supressors of lov-1 or pkd-2 mutants.

Kits and Diagnostic Systems for Performing the Assays

Kits for use in screening for use in any of the assays are provided.

The kits include transgenic or wild-type nematodes or both that express either wild-type or a mutant or a transgenic form of lov-1 and/or pkd-2. The nematodes may be on plates, in wells or in any form suitable for the assays. Kits containing nucleic acid encoding either of the two genes, portions thereof or vectors or plasmids containing the nucleic acids or probes based upon these sequences or reporter gene constructs containing all or portions of either or both genes and a reporter molecule are also provided. The nucleic acids may be in solution, in lyophilized or other concentrated form, or may be bound to a suitable substrate. The kits can include additional reagents for performing the assays, such reagents include any for performing any of the steps of the methods. The kits include instructions for performing the assays.

The kits may also include suitable ancillary reagents, such as the appropriate buffers and reagents. The kits may also include suitable ancillary supplies, such as microtiter plates, vials, calibrator solutions, controls, wash solutions and solid-phase supports.

The kits are typically provided in packages customarily utilized in diagnostic assays. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

The following examples are included for illustrative purposes only and are not intended to limit the scope of the invention.

EXAMPLE 1

Identification of C. elegans Orthologs of Human Polycystins

Mating behavior and mating efficiency assays. Males were generated by the use of him-5(e1490) (high incidence of male) strains or by heatshock of L4 hermaphrodites (Brenner (1974) Genetics 77:71–94). Mating efficiency (ME) tests were performed by pairing six tester L4 males with six paralyzed unc-52 or four actively moving dpy-17 or N2 L4 hermaphrodites. ME is the percentage of cross progeny to total progeny (Hodgkin: (1983) Genetics 103:43–64). Behavioral observations were done on a 0.5 cm diameter lawn of OP50 (Liu et al. Neuron 14:79–89). Hermaphrodites (N2 or unc-31(e169)) were placed on a lawn with the tester male. Behavioral phenotypes were determined by keeping time with a stopwatch and manually recording the behavioral series. In one trial, a male is observed for a minimum of 10 vulva encounters or for 10 minutes, whichever comes first. A male who does not respond to hermaphrodite contact within 10 minutes is considered response defective. Response ability reflects the percentage of males successfully responding to hermaphrodite contact. An individual male's vulva location ability was calculated as: Number of positive vulva locations/Total number of vulva encounters. Ability can vary from 100% (always locate) to 0% (never locate). Vulva location efficiency indicates the average behavior of a genotypic population. Pairwise comparisons were made using Mann-Whitney nonparametric and two-sided t tests (Instat for Macintosh).

Genetic screen for location of vulva (Lov mutants). PS1395 hermaphrodites of genotype plg-1 (e2001d); him-5 (e1490) were mutagenized with EMS (Brenner (1974) *Genetics* 77:71–94). plg-1(e2001d); him-5(e1490) males deposit a gelatinous plug over the hermaphrodite vulva post coitum. A decrease in plugging efficiency might reflect a decrease in mating ability. An F1 clonal screen was performed by picking individual F1 progeny of mutagenized hermaphrodites to individual plates and directly observing F2 males for behavioral defects.

An F2 clonal screen was performed such that 10 F1 progeny per P0 hermaphrodite were picked to the same plate, 10 F2 hermaphrodites per F1 pool were picked to individual plates, and F3 males were observed for decreased plugging efficiency and/or location of vulva (Lov) defects. lov-1(sy552); plg-1(e2001d); him-5 is a recessive mutation isolated in the F2 clonal screen. lov-1(sy552) males are response and Lov defective and also have a very low ME with dpy-17 hermaphrodites (ME-Dpy).

Genetic mapping of lov-1. Chromosomal linkage of lov-1(sy552) was determined by scoring the loss of genetic markers relative to response, Lov, and ME-Dpy phenotypes, which revealed linkage between dpy-10 and sy552. Further mapping was achieved via three factor crosses. From sy552/unc-4(e120) let-25(mn25) heterozygotes, Unc non-Let (Unc for uncoordinated, Let for lethal) recombinants were picked. As Unc males cannot mate, a test cross with sy552 males and Unc hermaphrodites was performed to generate non-Unc sy552/(sy552Δ)unc-25(mn25) males. Males were scored for response, Lov, and ME-Dpy defects. 2/12 Unc non-Let recombinants segregate the lov-1 mutant phenotype. These data placed lov-1 between unc-4 and let-25, closer to unc-4. Deficiency mapping indicated that mnDf21 uncovers sy552 whereas eDf21 does not.

Transformation rescue of lov-1(sy552) mutants. Cosmids and plasmids (15–100 ng/μl) in the region from the right breakpoint of eDf21 to the right breakpoint of mnDf21 and PHA-1 (pBX, 100 ng/μl were injected into lov-1(sy552); pha-1(e2123ts); htm-5(e1490). Stable lines were selected at either 19° or 25° C. (Schnabel et al. (1990) *Science* 250:686–688). Cosmid ZK945 rescued sy552 response and vulva location defects in four of five stable lines. A 16.9 kb HindIII fragment of ZK945 cloned into pBS(SK+) (plov1.1) containing ORFs ZK945.10 and ZK945.9 rescued sy552 behavioral defects in 4 of 6 stable lines. A 6.7 kb HindIII-BamHI fragment of ZK945 (plov-1::GFP1) containing ORF ZK945.10 did not rescue sy552 defects. plov-1.3 creates a frameshift at nucleotide 1.7724 in ZK945 inserting a BssHII GFP fragment from plasmid pPD95.02 out of frame into the StuI site of plov-1.1 plov-1,3 fails to rescue sy552.

PCR screen for genomic deletion of lov-1. Approximately 315,000 haploid genomes were screened using primers designed to delete the PKD/channel domain. Primer set 1 (SEQ ID Nos. 7 and 8, respectively), the outside primers were:
JC32 5'-CTCTATTTGTGGTTCGTTGGCG-3' and
JC36 5'-GGGAGTTTCCGTTTTCATGGGG-3'; and
internal nested primer set (SEQ ID Nos. 9 and 10, respectively) were:
JC33 5'-CTAGGACCGATGCAACAGCGAG-3' and
JC35 5'-AACGCTGATTGGTTCAAGTGTG-3')
and are approximately 2.5 and 2.4 kb apart, respectively. One deletion allele, lov-1(sy582Δ) was isolated. DNA sequence analysis indicated a deletion of nucleotides 16972 to 18027 of ZK945.

DNA-sequence analysis. RT-PCR from him-5(e1490) RNA using a combination of lov-1 primers generated overlapping cDNA clones bridging the junction between ZK945.10 and ZK945.9. Genefinder had predicted boundaries of the last exon of ZK945.10 (from position 25742 to 25174 of ZK945) and first exon of ZK945.9 (24923 to 24444). DNA sequence analysis of RT-PCR generated cDNA clones revealed three exons in the junction: one from 25742 to 25195, a second from 25151 to 25071, and a third initiating a position 25021, corresponding to exons I, J, and K, in FIG. 2b, respectively.

PCR Screen for Genomic Deletion of Pkd-2
For pkd-2 the used primers (SEQ ID Nos. 11–14, respectively) were as follows:
Outside Primers
LOV2.9 (Y73F8A nt 8546–8569) 5' CCCCTCGTTTGAC-CATTCTATGG 3'
LOV2.10 (Y73F8A nt 8438–8457) 5' ACGTGATCCTCT-GTCGATCCAG 3'
Nested Primers
LOV2.9A(Y73F8A nt 5599–5615) 5' AGATCAAGCT-GACTGCCCGTTC 3'
LOV2.10A(Y73F8A nt 5609–5631) 5' GATCCAGCGATT-AGCCTTTAA CG3'
One deletion allele, pkd-2(sy606) was isolated, which has a 2397 bp deletion from nucleotides 8338 to 5942 of Y73F8A (GenBank Accession No. AL 132862; corresponding to nucleotides 6734 to 4338 of SEQ ID NO. 5). The deletion starts in intron 3 and ends in intron 5, removing exons 4 and 5 (including the partial transmembrane spanning domain S1 and the polycystin motif) with the new splice in a different reading frame resulting in a stop codon (TGA) at 5736, and produced a knockout mutation. The resulting phenotype was the same as that resulting from a knockout of lov-1, thereby demonstrating that the two proteins are part of the same pathway that results in the observed phenotype.

EXAMPLE 2
Expression Analyses of LOV-1 and PKD-2
Methods
GFP (see, Chalfie et al. (1994) *Science* 263:802–805) expression was used as a marker for lov-1 and pkd-2 gene expression (see FIGS. 3a and 4A). plov-1::GFP1 was constructed by cloning a 6.7 kb HindIII-BamHI fragment of plov-1.1 into the vector pPD95.81, plov-1::GFP2 by cloning a HindIII-HpaI fragment. plov-1::GFP3 and plov-1::GFP4 are SacI and HindIII-HpaI (Klenow filled-in and religated) deletions of plov-1::GFP1, respectively. plov-1::GFP5 was constructed by cloning a 15.4 kb HindIII-AfeI fragment of plov-1.1 into the HindIII-SmaI site of pPD95.79. ppkd-2.1, ppkd-2::gfp1 and ppkd-2::gfp2 were constructed by cloning PCR-amplified 8.9 kb, 2.0 kb and 5.9 kb fragments into the vectors pPD95.97, pPD95.75 and pPD95.77, respectively. Transgenic animals were observed by fluorescence microscopy. Cells were identified by comparing Nomarski and fluorescent or confocal images of the same animals to determine cell-body position (Sulston et al. (1980) *Dev. Biol.* 78:542–576). HOB assignment was confirmed by laser ablation of precursor cells.

lov-1 Expression
lov-1::GFP1 is specifically expressed in male-sensory neurons, including four putative chemosensory CEM cephalic neurons, the hook neuron HOB (FIG. 4a), and the sensory ray neurons (FIG. 4b). lov-1 ::GFP1 expression was first observed in a few cells during late L4 lethargus (data not shown) while strong expression peaks in the adult male. In neuronal cell bodies, GFP expression is cytoplasmic (non-nuclear) and punctate (FIG. 4a and FIG. 4b). lov-1 ::GFP1 is localized at high levels in the cell body and ciliated endings of CEM (FIG. 4c), HOB, and ray neurons (FIG. 4b) but is not observed in axons. Localization of lov-1::GFP1 to sensory endings is consistent with plasma membrane localization and strengthens the argument that lov-1 mediates sensory perception required for mating behaviors. The temporal and spatial regulation of lov-1 is concordant with its role in adult male mating behavior. Rays mediate response to contact with a hermaphrodite (Liu et al. *Neuron* 14:79–89), the hook mediates vulva location (Liu et al. *Neuron* 14:79–89), and the CEMs are postulated to play a role in chemosensation (Ward et al. (1975) *J. Comp. Neurol.* 160:31 3–337).

lov-1::GFP1 expression was unaltered in lov-1(sy552) mutants. Expression of this fusion gene did not rescue lov-1(sy552) defects (FIG. 2a) and is therefore not functional. Sensory neurons and structures are normal in lov-1 (sy552) mutants as determined by osm-6::gfp expression, dye filling of sensory neurons, Nomarski observation, and SEM imaging (data not shown). The defects of lov-1(sy552) mutants therefore cannot be attributed to abnormal development or differentiation of the response and vulva location neurons. This indicates that lov-7(sy552) defects are due to defects in the function of the cells required for response and vulva location.

The Lov defect of mutations in lov-1 is not identical to ablation of HOB, the chemosensory neuron in which lov-1 expressed. The lov-1 mutant and HOB-ablated males pass the vulva (FIG. 1). The lov-1 males, however, are capable of precisely locating the vulva, whereas HOB-ablated males resort to slow search. Therefore, the HOB neuron of lov-1 functions, albeit in an attenuated capacity. If lov-1(sy552) and lov-1(sy582Δ) are loss of function alleles as the data suggests, then additional components are involved in Lov sensation.

Chemosensation and mechanosensation are likely involved in Lov *C. elegans* sensory neurons can be polymodal: for example, by ultrastructural assignment, the ASH neuron appears to be chemosensory yet functions in both mechanosensory (nose touch) and chemosensory (osmotic avoidance) modalities (Kaplan et al. (1993) *Proc. Natl. Acad. Sci. U.S.A.* 90:2227–2231). HOB might similarly be a polymodal sensory neuron. Ablation of either HOA or HOB produces identical phenotypes (Liu et al. *Neuron* 14:79–89) and HOA and HOB form multiple chemical synapses and electrical junctions (Sulston et al. (1980) *Dev. Biol.* 78:542–576), indicating extensive cross talk between the two hook sensory neurons. Since LOV-1 has an extensive extracellular mucin-like domain that could be involved in cell-cell or cell-matrix interaction, binding of vulva cell ligand(s) might potentially gate the LOV-1 polycystin-related channel. Another possibility is that LOV-1 could physically link the HOB sensory endings to the scherotized hook structure and couple hook deflection by the hermaphrodite vulva to intracellular voltage-activated signaling similar to hair cell mechanosensation (Hudspeth (1989) *Nature* 341:397–404) or touch response in *C. elegans* (Driscoll et al. in *C. elegans* II (ed. Riddle, D. I., Blumenthal, T., Meyer, B. J., and Priess, J. R.) 645–677 (Cold Spring Harbor Laboratory Press, New York, 1997).

pkd-2 Expression

As shown herein, *C. elegans* genome contains a human PKD-2 homolog PKD-2 possesses six membrane-spanning domains, a positively charged fourth membrane-spanning segment, a pore region, and the coiled coil domain of all polycistins. PKD-2 is localized to the same male-specific sensory neurons as LOV-1 (see, FIG. 3 and FIG. 4).

Since modifications will be apparent to those of skill in this art, it is intended that this invention be limited only by the scope of the appended claims.

SEQUENCE LISTING SUMMARY

SEQ ID No. 1 cDNA encoding human PKD1
SEQ ID No. 2 encoded human PKD1 protein
SEQ ID No. 3 sequence of a gene encoding nematode LOV-1 protein
SEQ ID No. 4 encoded nematode LOV-1 protein
SEQ ID No. 5 sequence of a gene encoding a nematode PKD-2 protein
SEQ ID No. 6 encoded nematode PKD-2 protein
SEQ ID No. 7 primer for lov-1 deletion mutant construction
SEQ ID No 8 primer for lov-1 deletion mutant construction
SEQ ID No. 9 internal primer for lov-1 deletion mutant construction
SEQ ID No. 10 internal primer for lov-1 deletion mutant construction
SEQ ID No. 11 primer for pk2-1 deletion mutant construction
SEQ ID No. 12 primer for pk2-1 deletion mutant construction
SEQ ID No. 13 internal primer for pk2-1 deletion mutant construction
SEQ ID No. 14 internal primer for pk2-1 deletion mutant construction
SEQ ID No. 15 sets forth the a LOV-1 mutant protein from sy582
SEQ ID No. 16 sets a PKD-2 mutant protein from sy606

What is claimed is:

1. An isolated polypeptide encoded by a nucleic acid molecule comprising one or more exons that are the complement of the sequence of nucleotides set forth in SEQ ID NO:5.

2. The polypeptide of claim 1 that comprises the sequence of amino acids set forth in SEQ ID NO:6.

3. An isolated polypeptide comprising the sequence of amino acids set forth in SEQ ID NO: 16.

4. The isolated polypeptide of claim 3, further comprising a transmembrane spanning domain and a polycystin motif.

5. An isolated polypeptide encoded by a nucleic acid molecule that is present in the genome of a nematode and that hybridizes along its full length to the full length of at least one region of SEQ ID NO:5 that is complementary to one or more exons, under conditions of high stringency, wherein the isolated polypeptide comprises a transmembrane spanning domain and a polycystin motif.

6. The isolated polypeptide of claim 5, wherein a *Caenorhabditis elegans* expressing the polypeptide rescues a sy660 mutant by exhibiting normal location of vulva and normal response male nematode sensory behaviors.

* * * * *